US011439697B2

(12) United States Patent
Soon-Shiong et al.

(10) Patent No.: US 11,439,697 B2
(45) Date of Patent: *Sep. 13, 2022

(54) NANT CANCER VACCINE

(71) Applicants: NantCell, Inc., Culver City, CA (US); Nant Holdings IP, LLC, Culver City, CA (US)

(72) Inventors: Patrick Soon-Shiong, Culver City, CA (US); Kayvan Niazi, Culver City, CA (US); Shahrooz Rabizadeh, Agoura Hills, CA (US); Hans G. Klingemann, Culver City, CA (US); Laurent H. Boissel, Culver City, CA (US); Barry J. Simon, Culver City, CA (US)

(73) Assignees: NantCell, Inc., Culver City, CA (US); Nant Holdings IP LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/391,694

(22) Filed: Aug. 2, 2021

(65) Prior Publication Data

US 2021/0353730 A1 Nov. 18, 2021

Related U.S. Application Data

(63) Continuation of application No. 16/312,246, filed as application No. PCT/US2017/040297 on Jun. 30, 2017, now Pat. No. 11,207,392.

(60) Provisional application No. 62/474,034, filed on Mar. 20, 2017, provisional application No. 62/473,207, filed on Mar. 17, 2017, provisional application No. 62/463,037, filed on Feb. 24, 2017, provisional application No. 62/404,753, filed on Oct. 5, 2016, provisional application No. 62/393,528, filed on Sep. 12, 2016, provisional application No. 62/371,665, filed on Aug. 5, 2016, provisional application No. 62/357,324, filed on Jun. 30, 2016.

(51) Int. Cl.
| | | |
|---|---|---|
| *A61K 35/17* | (2015.01) | |
| *A61K 39/00* | (2006.01) | |
| *A61K 38/20* | (2006.01) | |
| *C07K 16/28* | (2006.01) | |

(52) U.S. Cl.
CPC .. *A61K 39/001106* (2018.08); *A61K 38/2013* (2013.01); *A61K 38/2046* (2013.01); *A61K 38/2086* (2013.01); *A61K 39/00117* (2018.08); *A61K 39/001152* (2018.08); *A61K 39/001164* (2018.08); *A61K 39/001182* (2018.08); *C07K 16/2827* (2013.01); *A61K 2039/507* (2013.01); *A61K 2039/523* (2013.01); *C07K 2317/76* (2013.01)

(58) Field of Classification Search
CPC combination set(s) only.
See application file for complete search history.

(56) References Cited

U.S. PATENT DOCUMENTS

| | | | |
|---|---|---|---|
| 7,758,891 B2 | 7/2010 | Desai et al. | |
| 7,771,751 B2 | 8/2010 | Desai et al. | |
| 7,780,984 B2 | 8/2010 | Desai et al. | |
| 7,981,445 B2 | 7/2011 | De et al. | |
| 8,034,375 B2 | 10/2011 | Desai et al. | |
| 9,492,499 B2 | 11/2016 | Jaynes et al. | |
| 9,683,048 B2 | 6/2017 | Freeman et al. | |
| 10,813,952 B2 * | 10/2020 | Childs .................. | A61K 45/06 |
| 2012/0059670 A1 | 3/2012 | Sanborn et al. | |
| 2012/0066001 A1 | 3/2012 | Sanborn et al. | |
| 2014/0012843 A1 | 1/2014 | Soon-Shiong | |
| 2014/0114675 A1 | 4/2014 | Soon-Shiong | |
| 2015/0032468 A1 | 1/2015 | Soon-Shiong | |
| 2015/0125463 A1 | 5/2015 | Cogswell et al. | |
| 2015/0231241 A1 | 8/2015 | Chang et al. | |
| 2016/0095942 A1 | 4/2016 | Markovic et al. | |
| 2018/0222982 A1 * | 8/2018 | Dranoff ............ | A61K 39/39541 |
| 2019/0134174 A1 * | 5/2019 | Jones ............. | A61K 39/001106 |
| 2019/0381156 A1 | 12/2019 | Soon-Shiong | |
| 2020/0171137 A1 | 6/2020 | Soon-Shiong | |

FOREIGN PATENT DOCUMENTS

| | | |
|---|---|---|
| CA | 3 027 911 A1 | 1/2018 |
| CN | 104861067 A | 8/2015 |
| CN | 109789190 A | 5/2019 |
| JP | 2011-225538 A | 11/2011 |
| JP | 2019-524692 A | 9/2019 |
| KR | 10-2019-0031492 A | 3/2019 |
| MX | 2018015796 A | 5/2019 |
| TW | 201803598 A | 2/2018 |
| WO | 2011/139345 A2 | 11/2011 |
| WO | 2013/062505 A1 | 5/2013 |
| WO | 2013/192339 A1 | 12/2013 |
| WO | 2014/059036 A1 | 4/2014 |
| WO | 2014/163684 A1 | 10/2014 |
| WO | 2014/193982 A1 | 12/2014 |
| WO | 2014/210611 A1 | 12/2014 |
| WO | 2015/095811 A2 | 6/2015 |
| WO | 2015/184439 A1 | 12/2015 |
| WO | 2016/057554 A1 | 4/2016 |
| WO | 2016/061142 A1 | 4/2016 |

(Continued)

OTHER PUBLICATIONS

Klingemann et al (Frontiers in Immunology, Mar. 14, 2016, vol. 7, p. 1-7).*
Tonn et al (Cytotherapy, 2013, 15:1563-1570).*
Sun et al (International Journal of Nanomedicine, 2014, 9:1443-1452).*
Adkins et al (Journal of Clinical Oncology, 2011, 29, No. 15_suppl, abstract 5560).*

(Continued)

*Primary Examiner* — Laura B Goddard
(74) *Attorney, Agent, or Firm* — Martin Fessenmaier; Umberg Zipser LLP

(57) ABSTRACT

Cancer is treated using coordinated treatment regimens that uses various compounds and compositions that drive a tumor from the escape phase of cancer immunoediting to the elimination and equilibrium phase of cancer immunoediting.

20 Claims, 28 Drawing Sheets

(56) References Cited

FOREIGN PATENT DOCUMENTS

| WO | 2016/118527 A1 | 7/2016 |
| WO | 2016/164833 A1 | 10/2016 |
| WO | 2016/172722 A1 | 10/2016 |
| WO | 2017/035392 A1 | 3/2017 |
| WO | 2017/066256 A2 | 4/2017 |
| WO | 2017/100338 A1 | 6/2017 |
| WO | 2017/139725 A1 | 8/2017 |
| WO | 2017/161360 A2 | 9/2017 |
| WO | 2017/205810 A1 | 11/2017 |
| WO | 2017/210579 A1 | 12/2017 |
| WO | 2018/005973 A1 | 1/2018 |

OTHER PUBLICATIONS

Verschaegen et al (Journal of Clinical Oncology, May 20, 2016, 34, No. 15_suppl, abstract 9036).*
Milleretal (Blood, 2015, 126:abstract 1957).*
Acoba et al (Journal of Clinical Oncology, 35: (4_suppl):TPS510-TPS510, published online Mar. 21, 2017).*
Rx Times (Apr. 11, 2016) (http://rxtimes.com/altor-bioscience-corporation-partners-with-the-national-cancer-institute-to-further-develop-altors-alt-803-and-alt-801-cancer-immunotherapeutics/).*
Isacoff et al (Journal of Clinical Oncology, 2012, 30, No. 15_suppl, abstract e14582).*
Hamilton et al (Clinical Breast Cancer, 2013, 13:416-420).*
Masci et al (Anticancer Research, 2013, 33:4603-4610).*
Soliman (OncoTargets and Therapy, 2017, 10:101-112, published online Dec. 21, 2016).*
Final Office Action received for U.S. Appl. No. 16/312,246 dated Aug. 23, 2021 18 pages.
Notice of Final Rejection received for Korean Patent Application Serial No. 1020217002163 dated Sep. 29, 2021, 9 pages (Including English Translation).
Office Action received for Taiwanese Patent Application Serial No. 106122120 dated Sep. 17, 2021, 12 pages (Including English Translation).
Sow et al., "Combining low-dose or metronomic chemotherapy with anticancer vaccines—A therapeutic opportunity for lymphomas", Oncolmmunology, vol. 2, No. 12, 2013, 9 pages.
Mittal et al., "New insights into cancer immunoediting and its three component phases—elimination, equilibrium and escape", Current Opinion in Immunology, 2014, vol. 27, 18 pages.
Examination Report No. 1 received for Australian Patent Application Serial No. 2017290803 dated Oct. 2, 2019, 8 pages.
Schreiber et al., "Cancer Immunoediting: Integrating Immunity's Roles in Cancer Suppression and Promotion", Science, 2011, vol. 331, pp. 1565-1570.
Muenst et al., "The immune system and cancer evasion strategies: therapeutic concepts", Journal of Internal Medicine, 2016, vol. 279, pp. 541-562.
Zhu et al., "Novel Human Interleukin-15 Agonists", Journal of Immunology, 2009, vol. 183, pp. 3598-3607.
Kaufman et al., "Avelumab in patients with chemotherapy-refractory metastatic Merkel cell carcinoma: a multicentre, single-group, open-label, phase 2 trial", Lancet Oncol., 2016, vol. 17, No. 10, 28 pages.
Balint et al., "Extended evaluation of a Phase 1/2 trial on dosing, safety, immunogenicity, and overall survival after immunizations with an advanced generation Ad5 [E1-, E2b-]-CEA{6D) vaccine in late stage colorectal cancer", Cancer Immunology Immunotherapy, 2015, vol. 64, No. 8, pp. 1-20.
Morse et al., "Novel Adenoviral Vector Induces T Cell Responses Despite Anti-Adenoviral Neutralizing Antibodies in Colorectal Cancer Patients", Cancer Immunology Immunotherapy, 2013, vol. 62, No. 8, pp. 1-16.
Gabitzsch et al., "An Ad5[E1-, E2b-]-HER2/neu vector induces immune responses and inhibits HER2/neu expressing tumor progression in Ad5 immune mice", Cancer gene therapy, 2011, vol. 18, pp. 326-335.

Gabitzsch et al., "The generation and analyses of a novel combination of recombinant adenovirus vaccines targeting three tumor antigens as an immunotherapeutic", Oncotarget, 2015, vol. 6, No. 31, pp. 31344-31359.
Heery et al., "Phase 1 trial of a yeast-based therapeutic cancer vaccine (GI-6301) targeting the transcription factor brachyury", Cancer Immunology Research, 2015, vol. 3, No. 11, pp. 1-22.
Communication pursuant to Rule 164(1) EPC received for European Patent Application Serial No. 17821361.7 dated Jan. 31, 2020, 24 pages.
Hodson Jen, "NantBioScience and NantKwest Partner with the National Cancer Institute to Further Develop Recombinant NK Cells and Monoclonal Antibodies as Monotherapies and Combination Cancer Immunotherapies", NantKwest, 2016, p. 1-5.
Rhode et al., "Comparison of the super agonist complex, ALT-803, to IL-15 as cancer immunotherapeutics in animal models", Cancer Immunology Research, Jan. 2016, vol. 4, No. 1, pp. 1-25.
Hartley et al., "Pancreatic cancer, treatment options, and GI-4000", Human Vaccines & Immunotherapeutics, 2015, vol. 10, No. 11, pp. 3347-3353.
Epstein et al., "Identification of a Protein Fragment of Interleukin 2 Responsible for Vasopermeability", Journal of the National Cancer Institute, 2003, vol. 95, No. 10, pp. 741-749.
Atzpodien et al., "IL-2 in combination with IFN-α and 5-FU versus tamoxifen in metastatic renal cell carcinoma: long-term resultsofa controlled randomized clinical trial", British Journal of Cancer, 2001, vol. 85, No. 8, pp. 1130-1136.
First Office Action received for Taiwan Patent Application Serial No. 106122120 dated Feb. 7, 2020, 12 pages (Including English Translation).
Notice of Allowance received for U.S. Appl. No. 16/312,246 dated Sep. 15, 2021, 12 pages.
Bristol Myers Squibb Press Release (Aug. 20, 2014) (https://news.bms.com/press-release/rd-news/bristol-myers-squibb-and-celgene-enter-clinical-collaboration-agreement-evalua).
Final Office Action received for U.S. Appl. No. 16/783,734 dated Oct. 8, 2020, 30 pages.
Notice of Reasons for Refusal received for Japanese Patent Application Serial No. 2018569023 dated Jan. 5, 2021, 4 pages (Including English Translation).
Notice of Final Rejection received for Korean Patent Application Serial No. 1020197003046 dated Dec. 21, 2020, 8 pages (Including English Translation).
Non Final Office Action received for U.S. Appl. No. 16/783,734 dated Feb. 5, 2021 41 pages.
Mancheril et al "Nab-Paclitaxel and Carboplatin (Nab-PC) Regimen for Advanced Non-Small-Cell Lung Cancer", Hosp. Pharm., 2014, vol. 49, No. 9, pp. 804-808.
Antonia et al., "Nivolumab (Anti-PD-1; BMS-936558, ONO-4538) in Combination With Platinum-Based Doublet Chemotherapy (PT-DC) in Advanced Non-Small Cell Lung Cancer (NSCLC)", International Journal of Radiation Oncology, 2014, vol. 90, No. 5, 1 page.
Morishima et al., "CITN11-02 interim trial results: subcutaneous administration of recombinant human IL-15 (rhil-15) is associated with robust expansion of peripheral blood CD56+ NK cells", Journal for ImmunoTherapy of Cancer, 2014, vol. 2, No. 3, p. 80, pp. 1-2.
Klingemann et al., "Natural Killer Cells for Immunotherapy—Advantages of the NK-92 Cell Line over Blood NK Cells", Frontiers in Immunology, Mar. 14, 2016, vol. 7, No. 91, pp. 1-7.
Tonn et al., "Treatment of patients with advanced cancer with the natural killer cellline NK-92", Cytotherapy, 2013, vol. 15, pp. 1563-1570.
Notice of Grounds for Rejection received for Korean Patent Application Serial No. 20217002163 dated Mar. 5, 2021, 12 pages (Including English Translation).
Final Office Action received for U.S. Appl. No. 16/312,246 dated Feb. 22, 2021 40 pages.
Yu et al., "Simultaneous blockade of multiple immune system inhibitory checkpoints enhances antitumor activity mediated by interleukin-15 in a murine metastatic colon carcinoma model", Clinical Cancer Research, 2010, vol. 16, pp. 6019-6028.

(56) References Cited

OTHER PUBLICATIONS

Soliman Hatem H, "nab-Paclitaxel as a potential partner with checkpoint inhibitors in solid tumors", OncoTargets and Therapy, 2017, vol. 10, pp. 101-112.
Acoba et al., "Phase Ib/II study of ALT-803 in combination with gemcitabine and nab-paclitaxel in patients with advanced pancreatic cancer", Journal of Clinical Oncology, 2017, vol. 35, No. 4, pp. 1-4.
Non Final Office Action received for U.S. Appl. No. 16/312,246 dated May 14, 2021, 24 pages.
Notice of Allowance received for U.S. Appl. No. 16/783,734 dated May 19, 2021, 24 pages.
Notice of Allowance received for U.S. Appl. No. 16/783,734 dated Jun. 18, 2021, 6 pages.
International Preliminary Report on Patentability received for PCT Application Serial No. PCT/US2017/040297 dated Oct. 10, 2018, 07 pages.
International Search Report and Written Opinion received for PCT Application Serial No. PCT/US2017/040297 dated Oct. 18, 2017, 15 pages.
Communication pursuant to Rules 161 (2) and 162 EPC received for European Patent Application Serial No. 17821361.7 dated Feb. 6, 2019, 03 page.
Office Action Received for Canadian Patent Application Serial No. 3027911 dated Sep. 27, 2019, 6 pages.
Stubbs et al., "Whole recombinant yeast vaccine activates dendritic cells and elicits protective cell-mediated Immunity", National Medicine, 2001, vol. 7, 5 pages.
Zhang et al., "Machine learning competition in immunology—Prediction of HLA class I binding peptides", Journal of Immunology Methods, 2011, vol. 374, p. 1-4.
Gong et al., "Characterization of a human cell line (NK-92) with phenotypical and functional characteristics of activated natural killer cells", Leukemia, 1994, vol. 8, No. 4, pp. 652-658.
Maki et al., "Factors regulating the cytotoxic activity of the human natural killer cell line, NK-92", Journal of Hematotherapy Stem Cell Research, 2001, vol. 10, pp. 369-383.
Klingemann et al., "A cytotoxic NK-cell line (NK-92) for ex vivo purging of leukemia from blood", Biology of Blood and Marrow Transplantation, 1996, vol. 2, No. 2, 2 pages.
Examination report No. 2 received for Australian Patent Application Serial No. 2017290803 dated May 1, 2020, 4 pages.
Floros et al., "Anticancer Cytokines: Biology and Clinical Effects of IFN-α2, IL-2, IL-15, IL-21, and IL-12", Semin Oncology, 2015, vol. 42, No. 4, pp. 1-17.
International Search Report and Written Opinion received for Singaporean Patent Application Serial No. 11201811074R dated Mar. 6, 2020, 10 pages.
Non Final Office Action received for U.S. Appl. No. 16/783,734, dated Jul. 17, 2020, 133 pages.
MUSC launches first clinical trial involving two powerful drugs for lung cancer, Eureka Alert! Public Release, URL: https://www.eurekalert.org/pub_releases/2016-01/muos-mlf011416.php, Jan. 14, 2016, 2 pages.
"Bristol-Myers Squibb and Celgene Enter Clinical Collaboration Agreement to Evaluate Immunotherapy and Chemotherapy Combination Regimen", Bristol Myers Squibb Press Release, URL: https://news.bms.com/press-release/rd-news/bristol-myers-squibb-and-celgene-enter-clinical-collaboration-agreement-evalua. Aug. 20, 2014, pp. 1-6.

Klingemann et al, "Natural Killer Cells for Immunotherapy—Advantages of theNK-92 Cell Line over Blood NK Cells", Frontiers in Immunology, 2016, vol. 7, No. 91, pp. 1-7.
"Altor Bioscience Corporation Partners with the National Cancer Institute to Further Develop Altar's ALT-803 and ALT-801 CancerImmunothera peutics", Rx Times, URL: http://rxtimes.com/altor-bioscience-corporation-partners-with-the-national-cancer-institute-to-further-develop-altors-alt-803-and-alt-801-cancer-immunotherapeutics/, Apr. 11, 2016, 2 pages.
Extended European search report received for EP Patent Application Serial No. 17821361.7 dated Jun. 26, 2020, 24 pages.
Notice of Reasons for Refusal received for Japanese Patent Application Serial No. 2018-569023, dated Jun. 9, 2020 8 pages (Including English Translation).
Office Action received for Korean Patent Application Serial No. 10-2019-7003046, dated Jun. 26, 2020, 11 pages (Including English Translation).
Requirement for Restriction received for U.S. Appl. No. 16/312,246 dated Aug. 25, 2020, 11 pages.
Mkrtichyan et al., "Anti-PD-1 synergizes with cyclophosphamide to induce potent anti-tumor vaccine effects through novel mechanisms", Eur. Journal of Immunology, 2011, vol. 41, pp. 2977-2986.
Examination report No. 3 received for Australian Patent Application Serial No. 2017290803 dated Aug. 14, 2020, 5 pages.
Examination report No. 4 received for Australian Patent Application Serial No. 2017290803 dated Sep. 24, 2020, 3 pages.
Examination report No. 5 received for Australian Patent Application Serial No. 2017290803 dated Sep. 28, 2020, 4 pages.
Office Action received for Canadian Patent Application Serial No. 3027911 dated Sep. 24, 2020, 4 pages.
Office Action received in Taiwanese Patent Application Serial No. 106122120 dated Sep. 16, 2020, 16 pages (Including English Translation).
Non Final Office Action received for U.S. Appl. No. 16/312,246 dated Nov. 10, 2020, 158 pages.
Daly et al., "Clinical Trials Integrating Immunotherapy and Radiation for Non-Small-Cell Lung Cancer", Journal of Thoracic Oncology, 2015, vol. 10, No. 12, pp. 1685-1693.
Alvarez et al., "Advances in immunotherapy for treatment of lung cancer", Cancer Biology and Medicine, 2015, vol. 12, pp. 209-222.
Eureka Alert! Public Release (Jan. 14, 2016) (https://www.eurekalert.org/pub_releases/2016-01/muos-mlf011416.php).
Office Action received for Mexican Patent Application Serial No. MX/a/2018/015796 dated Oct. 28, 2021, 18 pages. (Including English Translation).
Notice of Final Rejection received for Korean Patent Application Serial No. 1020217002163 dated Dec. 7, 2021, 9 pages. (Including English Translation).
Office Action received for Canadian Patent Application Serial No. 3,027,911 dated Jan. 6, 2022, 6 pages.
Notice of Allowance received for U.S. Appl. No. 16/312,246 dated Oct. 27, 2021, 6 pages.
First Office Action received for Chinese Patent Application Serial No. 201780041456.4 dated Nov. 30, 2021, 14 pages. (Including English Translation).
Office Action received for Taiwanese Patent Application Serial No. 106122120 dated Jan. 5, 2022, 4 pages. (Including English Translation).
Notice of Allowance received for U.S. Appl. No. 16/312,246 dated Nov. 9, 2021, 6 pages.

\* cited by examiner

Prior Art Figure 1

NANT CANCER VACCINE

This application is a continuation of currently US application with the Ser. No. 16/312,246, which was filed Dec. 20, 2018, which is a 371 application of PCT/US2017/040297, which was filed Jun. 30, 2017, and which claims the benefit of priority to U.S. provisional applications having Ser. No. 62/357,324, filed on 30 June 16, 62/371,665, filed on 5 Aug. 16, 62/393,528, filed on 12 Sep. 16, 62/404,753, filed on 5 Oct. 16, 62/463,037, filed on 24 Feb. 17, 62/474,034, filed on 20 Mar. 17, and 62/473,207, filed on 17 Mar. 17.

FIELD OF THE INVENTION

The field of the invention is compositions and methods of cancer therapy, especially as it relates to cancer therapy in human.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

More recently, the immune system was described as playing a dual role in cancer as it can protect against cancer development by detecting and eliminating tumor cells, and as it can also promote cancer progression by selecting for tumor cells that can escape immune destruction. This paradoxical role of the immune system in cancer is also referred to as cancer immunoediting (Cancer immunoediting: integrating immunity's roles in cancer suppression and promotion. *Science.* 2011; 331:1565-70). Immunoediting is thought to include 3 phases, (1) elimination, in which tumor cells are detected and eliminated by the immune system; (2) equilibrium, in which cancer cell killing is balanced by tumor growth; and (3) escape, in which tumor cell variants evade immune defenses and grow rapidly.

Cancer cells harness various mechanisms to evade recognition and destruction by immune cells (see e.g., The immune system and cancer evasion strategies: therapeutic concepts. *J Intern Med.* 2016; 279:541-62). Cancer cells modulate in many cases the tumor microenvironment (TME) through recruitment of regulatory T cells (Tregs), myeloid-derived suppressor cells (MDSCs), and immunosuppressive macrophages (M2 macrophages). Cancer cells also evade the immune system by down-regulating expression of certain MHC (major histocompatibility complex) molecules, which are typically essential for T cells to recognize tumor-associated antigens (TAAs).

Traditional, molecularly uninformed treatment regimens of maximum tolerated dose (MTD) based chemotherapy, targeted therapy based on cancer marker signatures, and even monoclonal antibody therapy with high dose radiation impair the immune system, thereby generating tolerogenic cell death. Unfortunately, tolerogenic tumor cell death will enable the evasion of cancer immunosurveillance and facilitate the selection and escape of often multiple resistant, heterogenic clones with resultant metastasis and poor long term outcomes in multiple tumor types. Thus, and contrary to their intent, the traditional regimens and current standards of care may inadvertently exacerbate and perpetuate the escape phase of cancer immunoediting, and support the immunosuppressive tumor microenvironment, with poor long term outcomes in patients with cancer. Prior Art FIG. 1 exemplarily illustrates the three phases of cancer immunoediting, depicting a path from healthy tissue to transformed cells, and the above noted three phases together with typically encountered factors and signaling molecules.

Indeed, it has now been realized that the long held assumption that cancer cells grow in a linear fashion from a single clonally dominant mutant cell is largely incorrect, which has significant outcome implications both for the practice of high dose chemotherapy, as well as for the administration of single agent targeted therapy. It is now generally accepted that the vast majority of cancers arise and progress due to numerous mutations in cancer cells, and that cancer is a multi-clonal disease. Moreover, and for the most part, each patient's cancer is unique in terms of the nature and number of mutations. Consequently, a paradoxical situation exists as it relates to the current standard of care—that traditional MTD-based treatment regimens may be eliciting a short-term response but at the same time driving the patient's equilibrium phase into the escape phase by tilting the balance of the tumor microenvironment into an immunosuppressive state. Indeed, the traditional regimens and current standards of care may inadvertently exacerbate and perpetuate the escape phase of tumor immunoediting, by supporting the immunosuppressive tumor microenvironment resulting in poor long-term outcomes in patients with cancer. This insight into the potential cause for limited long-term remissions in most solid tumors following standard of care, requires a paradigm shift in the delivery of MTD-based chemotherapy and single-agent targeted therapy.

The notion that formation of transformed ("cancer") cells occur routinely as part of the physiological process of regeneration, and that clinical evidence of cancer is kept at bay during this dormancy phase (equilibrium) by the intact innate immune system of natural killer cells (elimination phase), as a normal physiological daily phenomenon in man, is intriguing. In this perspective, when the normal physiological state is overwhelmed by mutations or by the immunosuppressive state of the tumor microenvironment, the escape phase ensues, with the resultant clinical evidence of cancer.

However, to this date no treatment regimen exists that attempts to revert tumor cells or tissue from the escape phase back to the equilibrium or even elimination phase. Therefore, while numerous treatment compositions for cancer are known in the art, their use is typically limited to targeting specific defects in a tumor cell or to reduce checkpoint inhibition in a more general manner. Viewed from a different perspective, heretofore known cancer therapy is typically focused on selected parameters of a tumor cell, in which recurrence is nearly a fait accompli where tumor heterogeneity is present.

Consequently, there is still a need to provide treatment compositions and methods that address cancer immunoediting and that attempt to revert tumor cells or tissue from the escape phase back to the equilibrium or even elimination phase in a patient-specific manner.

SUMMARY OF THE INVENTION

The inventive subject matter is drawn to various uses of compositions and methods of cancer therapy in which various pharmaceutical compositions are administered to the patient to so revert tumor cells or tissue from the escape phase back to the equilibrium or even elimination phase. Moreover, at least some of the pharmaceutical compositions are specific to a patient and tumor in the patient, and will achieve in a coordinated fashion modulation of the tumor microenvironment to reduce immune suppression and increase stress and damage signals in the tumor, induction and enhancement of innate and adaptive immune responses, and generation of immune memory.

In one aspect of the inventive subject matter, the inventors contemplate a method of treating a tumor that includes a step of reverting an escape phase of the tumor by administering at least a first pharmaceutical composition that reduces immune suppression in a tumor microenvironment. In another step, the elimination phase is induced by administering at least a second pharmaceutical composition that enhances an adaptive immune response and/or an innate immune response, and in a further step the equilibrium phase of the tumor is maintained by administering at least a third pharmaceutical composition that biases the adaptive immune response towards a $T_H1$ response.

In preferred aspects, the first pharmaceutical composition comprises a drug that is bound to albumin (e.g., nanoparticulate albumin). Where desirable, the albumin may further be coupled to an antibody or fragment thereof to so further improve target specificity. Suitable drugs include Bendamustine, Bortezomib, Cabazitaxel, Chlorambucil, Cisplatin, Cyclophosphamide, Dasatinib, Docetaxel, Doxorubicin, Epirubicin, Erlotinib, Etoposide, Everolimus, Gefitinib, Idarubicin, Hydroxyurea, Imatinib, Lapatinib, Melphalan, Mitoxantrone, Nilotinib, Oxiplatin, Paclitaxel, Pazopanib, Pemetrexed, Rapamycin, Romidepsin, Sorafenib, Vemurafenib, Sunitinib, Teniposide, Vinblastine, Vinorelbine, and Vincristine, while suitable antibodies or fragments thereof include Reopro, Kadcyla, Campath, Simulect, Avastin, Benlysta, Adcetris, Cimzia, Rbitux, Prolia, Zevalin, Tysabri, Gazyva, Arzerra, Xolair, Vectibix, Perjeta, Cyramza, Lucentis, Rituxan, Bexar, Yondelis, and Herceptin. Alternatively, the antibody or fragment thereof may also bind specifically to a component of a necrotic cell (e.g., nucleolin, DNA, etc.).

In still further contemplated aspects, suitable first pharmaceutical compositions may also comprise a drug that inhibits a T-reg cell, a myeloid derived suppressor cell, and/or a M2 macrophage. Thus, suitable drugs include cisplatin, gemcitabine, 5-fluorouracil, cyclophosphamide, doxorubicin, temozolomide, docetaxel, paclitaxel, trabectedin, and RP-182 (see e.g., U.S. Pat. No. 9,492,499). Additionally, or alternatively, the first pharmaceutical composition may comprise a vascular permeability enhancer (e.g., a portion of IL2).

With respect to suitable second pharmaceutical compositions it is contemplated that such compositions may include a recombinant bacterial vaccine, a recombinant viral vaccine, or a recombinant yeast vaccine. Most typically, such vaccine is genetically engineered to express at least one of a tumor associated antigen (e.g., MUC1, CEA, HER2, Brachyury, an oncogenic Ras mutant protein, etc.) and a patient and tumor specific neoepitope. Moreover, the second pharmaceutical composition may also include a natural killer cell (e.g., an aNK cell, a haNK cell, or a taNK cell), and/or an immune stimulatory cytokine (e.g., IL-2, IL-15, IL-17, IL-21, IL-15 superagonist).

Contemplated third pharmaceutical compositions may comprise at least one of a checkpoint inhibitor (e.g., PD-1 inhibitor or a CTLA4 inhibitor), an immune stimulatory cytokine (e.g., IL-2, IL-7, IL-15, IL-17, IL-21, IL-15, and superagonist versions thereof), a recombinant bacterial vaccine, a recombinant viral vaccine, and a recombinant yeast vaccine.

Additionally, contemplated methods may further include a step of administering low dose radiation to the tumor.

In another aspect of the inventive subject matter, the inventors contemplate a method of treating a tumor. Such method will typically include a step of using omics information of a tumor and pathway analysis of the tumor to determine a chemotherapeutic treatment regimen, and a further step of administering the chemotherapeutic treatment regimen at a low-dose metronomic schedule. In still another step, a second treatment regimen is administered using at least one pharmaceutical agent that selectively delivers a drug to a tumor microenvironment, and a third treatment regimen is administered using at least one vaccine composition that is based on the omics information. Moreover, a fourth treatment regimen is administered that includes at least one of a checkpoint inhibitor and an immune stimulatory cytokine.

Preferably the omics information comprises at least one of whole genome sequence information, exome sequence information, transcriptome sequence information, and proteomics information, and/or the pathway analysis is a PARADIGM analysis. Notably, it should be appreciated that the chemotherapeutic treatment regimen is independent of an anatomical location of the tumor.

In further aspects of such methods, the at least one pharmaceutical agent may comprise a drug that is bound to an albumin, wherein the albumin is optionally a nanoparticulate albumin. Suitable drugs include Bendamustine, Bortezomib, Cabazitaxel, Chlorambucil, Cisplatin, Cyclophosphamide, Dasatinib, Docetaxel, Doxorubicin, Epirubicin, Erlotinib, Etoposide, Everolimus, Gefitinib, Idarubicin, Hydroxyurea, Imatinib, Lapatinib, Melphalan, Mitoxantrone, Nilotinib, Oxiplatin, Paclitaxel, Pazopanib, Pemetrexed, Rapamycin, Romidepsin, Sorafenib, Vemurafenib, Sunitinib, Teniposide, Vinblastine, Vinorelbine, and Vincristine. Where desired, the agent may further comprise an antibody or fragment thereof bound to the albumin, and preferred antibodies and fragment thereof include Reopro, Kadcyla, Campath, Simulect, Avastin, Benlysta, Adcetris, Cimzia, Rbitux, Prolia, Zevalin, Tysabri, Gazyva, Arzerra, Xolair, Vectibix, Perjeta, Cyramza, Lucentis, Rituxan, Bexar, Yondelis, and Herceptin.

Alternatively, or additionally, the at least one pharmaceutical agent may also comprise a drug that inhibits at least one of a T-reg cell, a myeloid derived suppressor cell, and a M2 macrophage, and especially preferred drugs include cisplatin, gemcitabine, 5-fluorouracil, cyclophosphamide, doxorubicin, temozolomide, docetaxel, paclitaxel, trabectedin, and RP-182.

Most preferably, suitable vaccine compositions comprise a recombinant bacterial vaccine, a recombinant viral vaccine, or a recombinant yeast vaccine, which may be genetically engineered to express at least one patient and tumor specific neoepitope.

With respect to checkpoint inhibitor it is preferred that the inhibitor is a PD-1 inhibitor or a CTLA4 inhibitor, and the immune stimulatory cytokine may be IL-2, IL-15, IL-17, IL-21, and/or an IL-15 superagonist. Additionally, contemplated methods may further comprise at least one of administration of a natural killer cell and low dose radiation.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
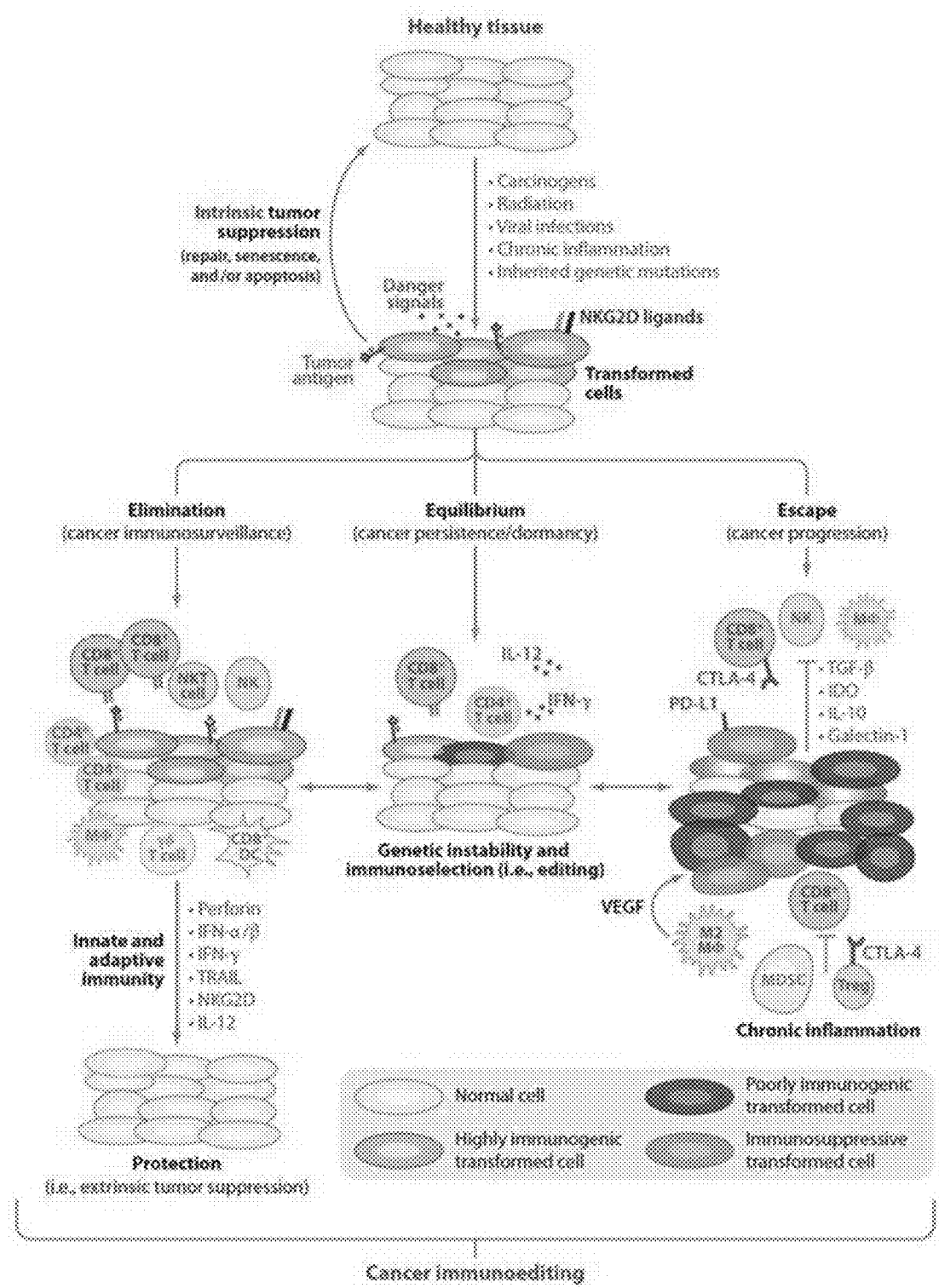
FIG. 1 is an exemplary schematic prior art illustration of the three phases of cancer immunoediting.

Traditional molecularly uninformed treatment regimens using chemotherapy at the maximum tolerated dose (MTD), targeted therapy using kinase inhibitors, agents that interfere with cell division, and antibody therapy with high dose radiation typically impair the immune system and so generate tolerogenic cell death, which in turn enables the selection and evasion of cancer immunosurveillance, and the escape of resistant, heterogenic clones with resultant metastasis and poor long term outcomes. Thus, traditional regimens and current standards of care may inadvertently perpetuate the escape phase of tumor immunoediting and support an immunosuppressive TME (tumor microenvironment).

A paradigm change in cancer care is required in which the treatment is based on the biology of the tumor that is largely independent of the anatomy, the mechanism of cancer evolution, and that is specifically tailored to the genomic changes of the patient's tumor. The treatment methods and compositions presented herein represent such an approach.

According to the inventive subject matter, the inventors now discovered that cancer therapy can be targeted to maximize immunogenic cell death (ICD) while maintaining and augmenting the patients' antitumor adaptive and innate responses to cancers. To that end, the treatment methods and uses of specific compounds and compositions presented herein take advantage of lower, metronomic doses of both cytotoxic chemotherapy and radiation therapy to so induce damage associated molecular patterns (DAMP) signals and tumor cell death while minimizing suppression of the immune system. In addition, contemplated methods also include use of various immunomodulatory agents, vaccines, checkpoint inhibitors, cell-based compositions, and fusion proteins to augment and stimulate the patient's adaptive and innate immune responses. Notably, by overcoming the immunosuppressed TME, the elimination phase of cancer can be reinstated through effector cells (e.g., mature dendritic cells, NK cells, cytotoxic T-cells, memory T-NK cells), that are preferably activated by combination therapy using fusion proteins, adenovirus and yeast vector vaccines, and natural killer cells. It should further be appreciated that such combinations will be targeted to the mutational patterns specific to the patients. Thus, off-target stimulation of an immune response is significantly reduced.

Most preferably, contemplated compounds and compositions are administered in a temporal spatial orchestration of a combination of immunotherapeutic products to immunomodulate the tumor microenvironment, activate the innate adaptive immune system and to induce immunogenic cell death (ICD). More specifically, the inventors contemplate that such approach will result in coordinated effects, and especially in:

(1) Breaking the escape phase of cancer immune editing, preferably by overcoming the tumor immunosuppressed state. Such treatment is preferably informed by tissue and/or liquid biopsies, executed with low-dose metronomic chemotherapeutic agents capable of inhibiting T-Reg, MDSC's, and M2 Macrophages, and/or by inhibition of cytokines (e.g., TGF β) which enhance immunosuppressive immune system;

(2) Inducing the elimination phase of cancer immune editing, preferably done by up-regulating and/or induction of damaged associated molecular patterns (DAMP) signals, up-regulating of tumor associated MHC restricted antigens and stress receptors (NKG2D), up-regulating tumor specific receptors such as PD-L1 and/or via low-dose radiation, administration of immunomodulatory drugs (IMiDs) and histone deacetylase (HDAC) agents, and/or activation of dendritic cells, natural killer cells, cytotoxic T-cells, memory T and/or Natural Killer (NK) cells through adenovirus, bacterial, and/or yeast vector vaccines, cytokine fusion protein administration, checkpoint inhibitors, and/or NK cell therapy infusion; and (3) Reinstatement of the equilibrium phase of cancer immune editing, which can be achieved by maintaining $T_H1$ status of the patient's immune system with vaccine boosters, cytokine fusion protein maintenance, and/or regular exogenous NK infusions.

Viewed from another perspective, the inventors contemplate that the temporal spatial manner of contemplated treatments will recapture the natural (pre-cancer) state of a patient's immune system by overcoming the escape phase, reestablishing the elimination phase, and by accomplishing long term maintenance through support of the equilibrium phase.

To that end, and among other contemplated options, preferred treatment components include (a) nanoparticle albumin bound (Nab) chemotherapy combinations to enter the tumor microenvironment (e.g., via transcytosis) to overcome the tumor suppressor environment, (b) antigen producing vaccine entities (e.g., recombinant adenovirus, bacteria, and/or yeast) that directly or indirectly deliver tumor associated antigens and/or patient- and tumor-specific neoantigens to immune competent cells to activate immature dendritic cells in a patient and tumor specific manner to induce and/or enhance an adaptive immune response, (c) natural killer cells, which may be endogenous (e.g., by stimulation with IL-15 or IL-15 superagonist) and/or exogenous (e.g., genetically modified NK cells such as aNK, haNK, taNK cells) to induce and/or enhance an innate immune response, and (d) endogenous activated memory T- and/or NK-cells to sustain long term remission, preferably activated via vaccine, cell therapy, and fusion proteins (e.g., genetically engineered fusion protein cytokine stimulators and/or checkpoint inhibitors).

Therefore, and viewed from a mechanistic perspective, the inventors contemplate that the temporal spatial orchestration of a combination of immunotherapeutic compounds and/or compositions will immunomodulate the tumor microenvironment, induce immunogenic cell death (ICD) and result in long term sustainable remission of multiple tumor types with lower toxicity and higher efficacy than current standards of care by (a) penetrating the tumor microenvironment to overcome the tumor immunosuppressed state, which is preferably informed by tissue and liquid biopsies, with low-dose metronomic chemotherapeutic agents capable of inducing immunogenic cell death (ICD), along with inhibitors of one or more immunosuppressive cytokines; (b) up-regulating induction of damaged associated molecular patterns (DAMP) signals, and up-regulating tumor associated MHC restricted antigens and stress receptors (NKG2D) through low-dose radiation, IMiDs (immunomodulatory drugs) and HDAC (histone deacetylating drugs) agents; (c) activating dendritic cells, natural killer cells, cytotoxic T-cells, memory T and/or NK cells through various cytokine fusion proteins, checkpoint inhibitor administration, and NK cell therapy infusion; and (d) maintaining the equilibrium state through boost vaccines (e.g., antigen adenoviral, bacterial, and/or yeast vectors delivering tumor associated and neoantigens), NK activating agents, and various immune stimulating fusion proteins. Indeed, it should be appreciated that contemplated methods and uses take advantage of the tumor as a source of antigenicity and adjuvanticity.

Notably where a treatment approach according to the inventive subject matter is used, it should be recognized that most of the drugs in such approach are not primarily used in their traditional function (e.g., to block a specific receptor or inhibit a specific enzyme) but that the drug combinations are used in a concerted manner to modulate the immune biology of the tumor and the immune system of the patient, thereby reverting the tumor from the escape phase to the elimination and equilibrium phase. In contrast, currently used combinations have so far failed to make use of, or even appreciate modulation of cancer immunoediting as a strategic approach in cancer therapy.

Figure 2:
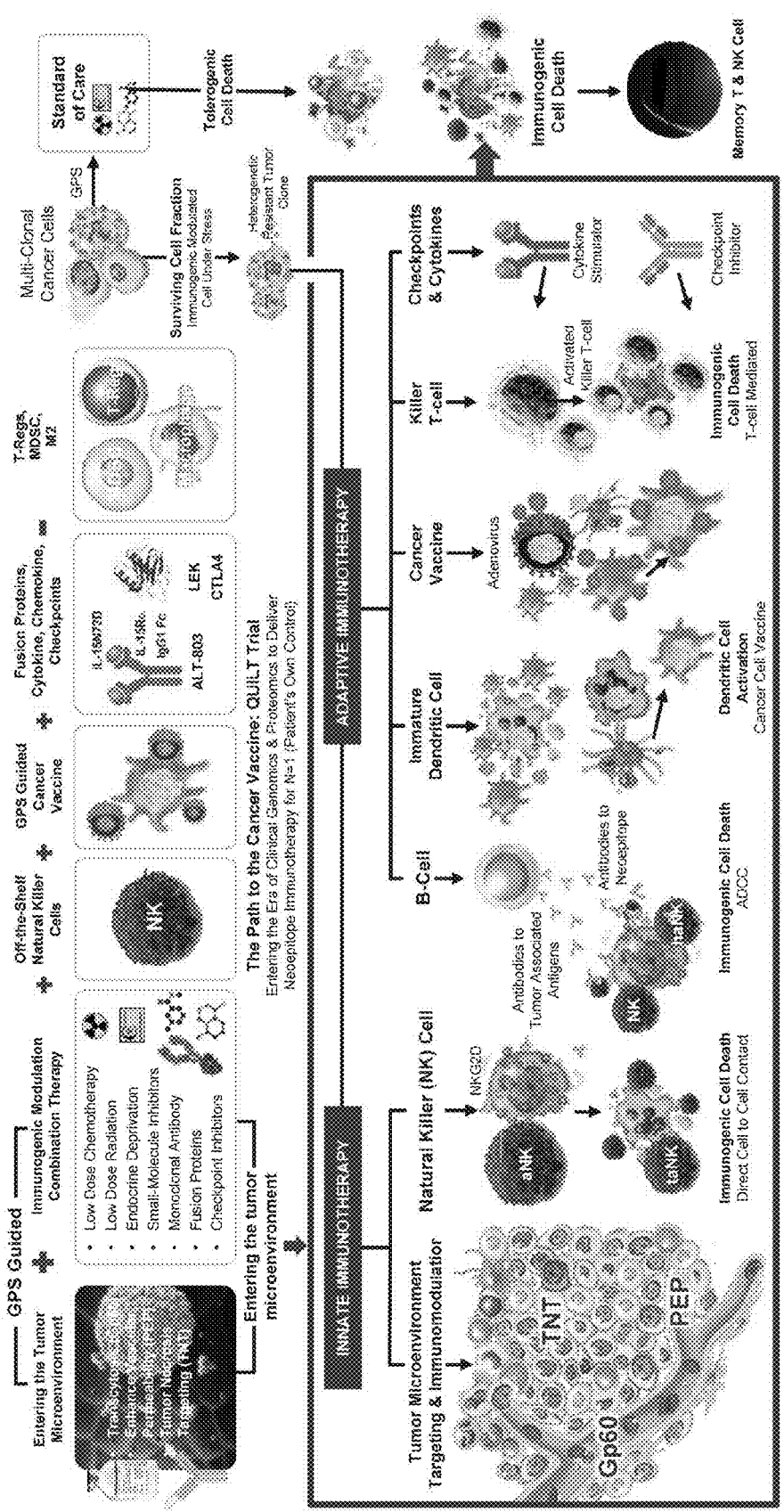
FIG. 2 is an exemplary schematic illustration of a treatment according to the inventive subject matter.

FIG. 2 exemplarily illustrates various aspects of the inventive subject matter. Here, as is schematically shown, while a tumor with multi-clonal cancer cells could be treated using standard of care, which will result in tolerogenic cell death of a proportion of tumor cells, treatment will typically result in a surviving cell fraction that represents cells that are resistant to the standard of care and that have establish tumors and/or metastases with a TME that is now immune suppressive and unresponsive to many treatment strategies. Moreover, it should be noted that tolerogenic cell will generally not result in an immune stimulation as is typically encountered in ICD (immunogenic cell death—death of a cell due to an immune response of a cancer patient against one or more antigens of the tumor, typically via innate and adaptive immune response).

In contrast, contemplated uses and methods are designed to first reduce or even revert immune suppression of the TME by use of compositions and compounds that specifically or preferentially enter the TME as is further described in more detail below. In addition to the reduction or inhibition of immune suppression of the TME, contemplated methods and uses may further preferably comprise a low-dose metronomic chemotherapy. Such low-dose and metronomic chemotherapy advantageously allows the patient's immune system to function to a degree that allows both mounting of an innate and an adaptive immune response in a therapeutically effective manner.

Moreover, it is generally contemplated that such low-dose metronomic chemotherapy is informed by omics analysis and pathway analysis of the tumor of the patient. For example, omics analysis can identify specific mutations associated with a tumor as well as presence and expression of neoepitopes specific to the patient and tumor. Thus, specific mutations can be targeted with drugs know to treat such mutations (e.g., kinase inhibitors for k-ras, etc.). In addition, thusly identified tumor and patient specific mutations can also be used in immune therapy as is further described in more detail below. Preferably, omics analysis is performed using a tumor and matched normal sample from the same patient as is exemplarily described in US20120059670 and US20120066001). Thus, it should be appreciated that omics analysis of a patient's tumor will not only reveal druggable targets but also provide patient and tumor specific neoepitope information that can be employed in immune therapy.

For example, patient- and tumor-specific neoantigens can be identified via analyzing and comparing omics data from diseased tissue and healthy tissue of a patient, (e.g., via whole genome sequencing and/or exome sequencing, etc.). Among identified mutations, it is generally preferred that patient-specific neoantigens are further selected by filtering by at least one of mutation type, transcription strength, translation strength, and a priori known molecular variations. Further details on identification of patient-specific neoantigens and/or cancer-specific, patient-specific neoantigens are described in detail in the international patent application No. PCT/US16/56550.

Moreover, it is especially contemplated that the tumor-related antigen is a high-affinity binder to at least one MHC Class I sub-type or at least one MHC Class II sub-type of an HLA-type of the patient, which may be determined in silico using a de Bruijn graph approach as, for example, described in WO 2017/035392, or using conventional methods (e.g., antibody-based) known in the art. The binding affinity of the human disease-related antigen is tested in silico to the determined HLA-type. The preferred binding affinity can be measured by lowest KD, for example, less than 500 nM, or less than 250 nM, or less than 150 nM, or less than 50 nM, for example, using NetMHC. Most typically, the HLA-type determination includes at least three MHC-I sub-types (e.g., HLA-A, HLA-B, HLA-C, etc.) and at least three MHC-II sub-types (e.g., HLA-DP, HLA-DQ, HLA-DR, etc.), preferably with each subtype being determined to at least 4-digit depth. It should be appreciated that such approach will not only identify specific neoantigens that are genuine to the patient and tumor, but also those neoantigens that are most likely to be presented on a cell and as such most likely to elicit an immune response with therapeutic effect.

Of course, it should be appreciated that matching of the patient's HLA-type to the patient- and cancer-specific neoantigen can be done using systems other than NetMHC, and suitable systems include NetMHC II, NetMHCpan, IEDB Analysis Resource (URL immuneepitope.org), Rank-Pep, PREDEP, SVMHC, Epipredict, HLABinding, and others (see e.g., *J Immunol Methods* 2011; 374:1-4). In calculating the highest affinity, it should be noted that the collection of neoantigen sequences in which the position of the altered amino acid is moved (supra) can be used. Alternatively, or additionally, modifications to the neoantigens may be implemented by adding N- and/or C-terminal modifications to further increase binding of the expressed neoantigen to the patient's HLA-type. Thus, neoantigens may be native as identified or further modified to better match a particular HLA-type.

Moreover, where desired, binding of corresponding wild type sequences (i.e., neoantigen sequence without amino acid change) can be calculated to ensure high differential affinities. For example, especially preferred high differential affinities in MHC binding between the neoantigen and its corresponding wild type sequence are at least 2-fold, at least 5-fold, at least 10-fold, at least 100-fold, at least 500-fold, at least 1000-fold, etc.

In addition, the omics information (especially where the omics information comprises whole genome sequencing or exome sequencing, RNA sequence and transcription data, and (preferably quantitative) proteomics information) can also be used to determine the status of various cell signaling pathways. Such pathway information, and especially in conjunction with mutational information, may reveal further druggable targets within a cell that are independent from anatomical features of the tumor (e.g., presence of HER2 signaling in a non-breast cancer). Particularly preferred pathway analyses that are based on omics information include those described in WO 2011/139345, WO 2013/062505, WO 2014/193982, WO 2014/059036, WO 2014/210611, WO 2015/184439, and WO 2016/118527. Viewed from a different perspective, omics data in contemplated treatments and uses will be employed to both, inform generation of immune therapeutic compositions as well as inform selection of chemotherapeutic drugs based on pathway information rather than tumor type and location. Therefore, suitable omics data include whole genome sequencing data, exome sequencing data, RNA sequence and transcription data, and proteomics data (e.g., quantitative proteomics data from mass spectroscopic analyses).

Use of genomics, transcriptomics, and proteomics data, especially in conjunction with pathway analysis of the obtained data allows for identification of key altered cell signaling pathways, and with that an avenue to treatment that is agnostic to the anatomical type of tumor but sensitive to the functional alteration in signal transduction and associated cellular events. This will not only allow for the identification of drugs suitable for the treatment of the tumor that would otherwise not be considered, but also allow for modulation of immune parameters of the tumor. DNA, RNA, and protein signatures and associated changes in signaling pathways can be identified, even before treatment begins. Indeed, non-assumptive stochastic analysis enables treatment decisions that are unbiased to the traditional tissue-by-tissue assignment of therapeutics or an a priori assumption that a few hundred DNA would be the drivers of the cancer.

With further respect to reduction or inhibition of immune suppression of the TME it is contemplated that the TME can be directly targeted with drugs that preferentially accumulate in the TME. For example, direct targeting includes use inhibitors or T-regs (regulatory T cells), MDSC (myeloid derived suppressor cells), and/or M2 macrophages, use of albumin drug conjugates as further described below, and/or use of drugs coupled to antibodies or fragments thereof that bind to necrotic cells (e.g., nucleolin, histones, DNA, etc.) Indirect targeting will typically employ permeability enhancing drugs that permeabilize the neovasculature of the TME (e.g., IL-2 or PEP fragment thereof) to so allow facile access of drugs to the TME.

In still further contemplated aspects of reduction or inhibition of immune suppression of the TME, it is contemplated that the TME may also be subjected to stress conditions that induce the expression and display of various stress signals, and especially NKG2D to so attract NK and other immune competent cells. For example, stress responses may be induced using low dose radiation therapy (e.g., below 8Gy), hormone deprivation, small molecule inhibitors, etc. Notably, where one or more of the above approaches are taken, it is believed that at least some of the tumor cells will be subjected to exposure to various immune competent cells, and especially natural killer cells (which may be the patient's own, or exogenous NK cells as described further below). Thus, addressing the TME may result in a first innate immune response. Advantageously, such innate immune response (e.g., via NK cells) will trigger an immune cascade and stimulate adaptive immune response to components of cells killed by the innate immune response. Therefore, it should be appreciated that the treatments and uses certain compounds and compositions can be employed to reduce or eliminate immune suppression in the TME and as such can be used to block or revert the escape phase of cancer immunoediting.

Upon reduction or reversal of immune suppression in the TME, or concurrently with the reduction or reversal of immune suppression in the TME, the inventors contemplate that the elimination phase of the tumor can be induced, preferably via one or more pharmaceutical compounds or compositions that enhance at least one of an adaptive immune response and an innate immune response. With respect to preferred induction of adaptive immune response it is generally preferred that such response is generated by one or more vaccine compositions. For example, especially preferred vaccine compositions are formulated to generate an immune response against tumor associated antigens (e.g., MUC-1, brachyury, CEA, HER2, etc.) and/or (preferably patient and tumor specific) tumor neoepitopes. In that context, it should be appreciated that the tumor neoepitopes used in the generation of the adaptive immune response will be selected on the basis of the omics information as noted above. Advantageously, omics information for a specific patient is therefore used for at least identification of a chemotherapeutic drug (preferably via pathway analysis using the omics data) and for identification of suitable neoepitopes to generate an immune therapeutic composition.

Among other suitable options, it is typically preferred that the immune therapeutic composition is a cancer vaccine that is based on at least one of a bacterial vaccine, a yeast vaccine, and an (adeno)viral vaccine as described in more detail below. It should be appreciated that the cancer vaccines are preferably recombinant entities that have expressed in the intracellular space one or more tumor associated antigens and/or tumor neoepitopes, or that the recombinant entity is a recombinant viral expression vector that encodes. In further preferred aspects, it should also be noted that the vaccine compositions may be administered sequentially (e.g., first bacterial, then yeast, then viral), or that only one or two vaccine compositions are used (e.g., only adenoviral or bacterial vaccine). Of course, it should be appreciated that the recombinant protein(s) or nucleic acid(s) encoding the protein(s) may be the same in all vaccine compositions, overlapping, or different.

With respect to the enhancement of the innate immune response in the elimination phase it is generally preferred that the innate immune response may be from the patient's own immune system or via exogenous immune competent cells. For example, where the patient's innate immune response is enhanced, proliferation and activity of natural killer cells and activated T-cells may be boosted using one or more immune stimulatory cytokines as discussed in more detail below. Alternatively, or additionally, the patient may also receive allogenic NK cells, and most preferably activated NK cells (such as aNK cells, haNK cells, or taNK cells) and/or recombinant T-cells with a chimeric T cell receptor. NK transfusion, and especially aNK and haNK transfusion advantageously amplify prior stress signals present on the tumor cells in the TME (typically induced by metronomic low dose chemo therapy, low dose radiation, and/or endocrine deprivation). Additionally, haNK cells may be coupled via the high affinity CD16 receptor to one or more antibodies that bind tumor associated antigens or neoepitopes. As such, the innate immune response may be specifically directed to a tumor cell. The elimination phase may be further enhanced or supported by administration of one or more cytokines, fusion proteins, and/or chemokines as is further discussed in more detail below.

Therefore, it should be appreciated that compounds and compositions administered to induce or enhance the elimination phase will be particularly effective as the TME and the tumor were previously conditioned to have reduced or abrogated immune suppression and to have additional stress signals. Viewed from a different perspective, all or almost all of the previously known treatments typically failed to exhibit therapeutic effect as such treatments were delivered or administered to a TME that had maintained immune suppression. In contrast, the presently contemplated methods and uses advantageously precondition the tumor and the TME to so render treatments that induce the elimination phase more effective. Where desired, the elimination phase may be further supported by administration of one or more drugs that inhibit T-regs, MDSCs, and/or M2 macrophages.

Upon induction of the elimination phase for a predetermined time or predetermined treatment response, contemplated methods and uses will then be directed to maintain the equilibrium phase. At this point, residual tumors, metastases, and tumor cells will have been largely eliminated in a process that also stimulated an immune cascade (i.e., a process in which tumor cells attacked by immune competent cells (e.g., NK cells, cytotoxic T cells) release immunogenic proteins of the tumor, leading to epitope spread and further immune response), leading to immunogenic cells death and immune memory (e.g., memory T-cells, memory B-cells, memory NK cells). To maintain the immune status of the patient and to further boost memory against the antigens that were present on the tumor cells, the patient may receive checkpoint inhibitors, immune stimulatory cytokines, and/or further vaccine doses as described above. Such treatment and use of the above compounds and compositions will be effective to bias the adaptive immune response and/or equilibrium phase towards a $T_H1$ response (typically characterized by production of Interferon-gamma, tumor necrosis factor alpha, and IL-2; in contrast, a $T_H2$ response is typically characterized by production of IL-4, IL-5, IL-6, IL-10, and IL-13). Maintenance using contemplated compounds and compositions will maintain the equilibrium phase, support innate and adaptive immune response, and help generate memory NK, T- and B-cells.

Viewed form a different perspective, providing a treatment regimen that reverts the escape phase of the tumor, that concurrently or more preferably subsequently induces the elimination phase, and that maintains the equilibrium phase of the tumor can overcome immune suppression and evasion of previously developed or established tumors. Thus, while contemplated methods and uses employ some of the same compounds and compositions as traditional treatments, the coordinated treatment to achieve reversal of the escape phase to the elimination phase and maintenance phase has neither been recognized nor appreciated.

Figure 3:
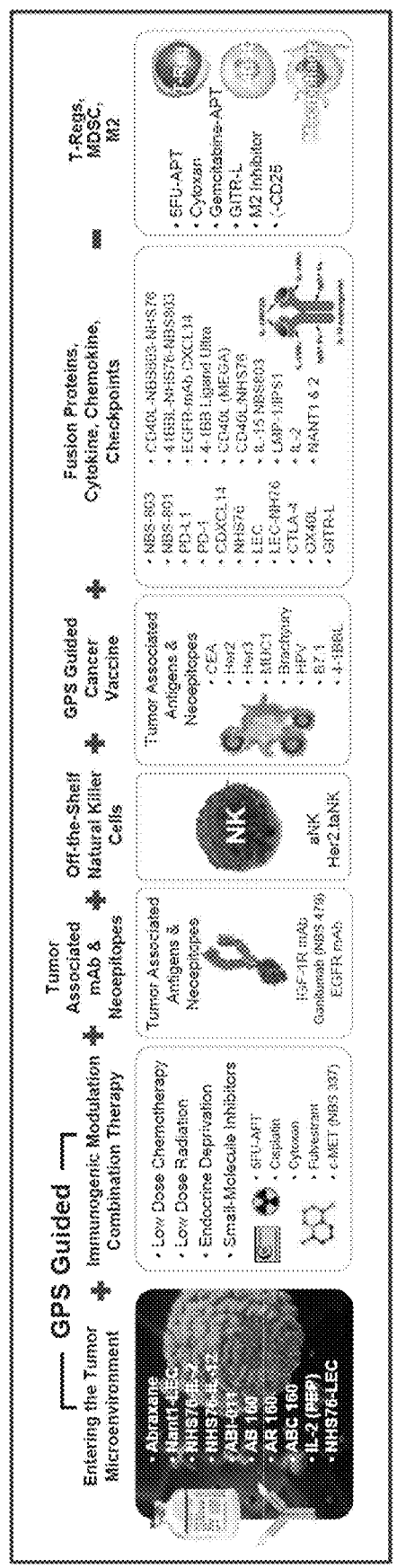
FIG. 3 is an schematic illustration with exemplary compounds used in selected steps of a treatment according to the inventive subject matter.

FIG. 3 depicts schematically some of the compounds, compositions and uses that are contemplated. For example, the TME may be addressed using abraxane (paclitaxel coupled to nanoparticulate albumin), various antibody-drug conjugates that have an antibody portion that binds specifically to a component of a necrotic cell. For example, albumin drug conjugates may be used to exploit the gp60-mediated transcytosis mechanism for albumin in the endothelium of the tumor microvasculature. Thus, various drug conjugates with albumin are contemplated in which a drug is non-covalently coupled to albumin (or nanoparticulate refolded albumin), and contemplated drugs include various cytotoxic drugs, antimetabolic drugs, alkylating agents, microtubulin affecting drugs, topoisomerase inhibitors, drugs that interferes with DNA repair, etc. Therefore, suitable drugs inclue Bendamustine, Bortezomib, Cabazitaxel, Chlorambucil, Cisplatin, Cyclophosphamide, Dasatinib, Docetaxel, Doxorubicin, Epirubicin, Erlotinib, Etoposide, Everolimus, Gefitinib, Idarubicin, Hydroxyurea, Imatinib, Lapatinib, Melphalan, Mitoxantrone, Nilotinib, Oxiplatin, Paclitaxel, Pazopanib, Pemetrexed, Rapamycin, Romidepsin, Sorafenib, Vemurafenib, Sunitinib, Teniposide, Vinblastine, Vinorelbine, and Vincristine. Such conjugates will advantageously be administered in a low dose and metronomic fashion. Further contemplated drugs for conjugation (or use without conjugation) to albumin include drugs that inhibit suppressor cells in the TME, and especially T-reg cells, myeloid derived suppressor cells, and/or M2 macrophages. For example such drugs include cisplatin, gemcitabine, 5-fluorouracil, cyclophosphamide, doxorubicin, temozolomide, docetaxel, paclitaxel, trabectedin, and RP-182 (see e.g., U.S. Pat. No. 9,492,499).

Likewise, where entry of a drug conjugate into the TME is mediated by the FcRn receptor of the endothelium of the tumor microvasculature, various conjugates and chimeric proteins with the Fc portion of an immunoglobulin are contemplated. Thus, particularly contemplated conjugates and chimeric proteins will include immune stimulatory cytokines (e.g., IL-2, IL15, etc.) and chemokines (e.g., CXCL14 CD40L, etc.). Alternatively, the TME may also be targeted in a more non-specific manner by breaching the tumor microvasculature, typically using a permeability enhancing peptide portion of IL-2 (PEP). Such permeability enhancers are preferably provided together with or prior to administration of drugs that bind to necrotic tumor cells and/or drugs that inhibit suppressor cells.

As is also schematically depicted in FIG. 3, immunogenicity of the tumor cells in the TME may be increased using one or more chemotherapeutic drugs that are preferably selected on the omics and pathway analysis as noted above. Such treatment is preferably performed at low dose and in a metronomic fashion to trigger overexpression or transcription of stress signals. For example, it is generally preferred that such treatment will be effective to affect at least one of protein expression, cell division, and cell cycle, preferably to induce apoptosis or at least to induce or increase the expression of stress-related genes (and especially NKG2D ligands, DAMPsignals). It should be noted that chemotherapeutic agents may advantageously stimulate both the innate and adaptive arms of the immune system by inducing an immunogenic type of cell death in tumor cells resulting in the induction of specific damage associated molecular pattern (DAMP) signals. These signals trigger phagocytosis of cell debris, promoting maturing of dendritic cells, activation of T- and NK cells, ultimately promoting anti-tumor responses.

Thus, in contemplated aspects, treatment to increase immunogenicity and/or decrease immune suppression will include low dose treatment using one or more of chemotherapeutic agents that target the TME. Most typically, the low-dose treatments will be at dosages that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Viewed from a different perspective, low dose administration will be at dosages that are between 5-10%, or between 10-20%, or between 20-30%, or between 30-50%, or between 50-70% of a normally recommended dosage as indicated in the prescribing information for the drug. Additionally, and where desired, such low-dose regimen may be performed in a metronomic manner as described, for example, in U.S. Pat. Nos. 7,758,891, 7,771, 751, 7,780,984, 7,981,445, and 8,034,375.

In addition, contemplated treatments to target the TME to increase immunogenicity and/or decrease immune suppression may be accompanied by radiation therapy, and especially targeted stereotactic radiation therapy at relatively low dosages (e.g., dosages that are between 5-10%, or between 10-20%, or between 20-30%, or between 30-50%, or between 50-70% of a normally recommended dosage for radiation of the tumor). To take advantage of expression and display or secretion of the stress signals, it is generally preferred that low dose chemotherapy and/or low dose radiation is followed within 12-36 by transfusion of NK cells (e.g., aNK cells, haNK cells, or taNK cells) to enhance an innate immune response.

Therefore, it is contemplated that contemplated treatments and uses may also include transfusion of autologous or heterologous NK cells to a patient, and particularly NK cells that are genetically modified to exhibit less inhibition. For example, the genetically modified NK cell may be a NK-92 derivative that is modified to have a reduced or abolished expression of at least one killer cell immunoglobulin-like receptor (KIR), which will render such cells constitutively activated. Of course, it should be noted that one or more KIRs may be deleted or that their expression may be suppressed (e.g., via miRNA, siRNA, etc.), including KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest as aNK cells (activated natural killer cells). Such cells may then be further modified to express the co-stimulatory molecules as further discussed below. In addition, contemplated NK cells suitable for use herein also include those that have abolished or silenced expression of NKG2A, which is an activating signal to Tregs and MDSCs.

Alternatively, the genetically engineered NK cell may also be an NK-92 derivative that is modified to express a high-affinity Fcγ receptor (CD16-158V). Sequences for high-affinity variants of the Fcγ receptor are well known in the art, and all manners of generating and expression are deemed suitable for use herein. Expression of such receptor is believed to allow specific targeting of tumor cells using antibodies produced by the patient in response to the treatment contemplated herein, or supplied as therapeutic antibodies, where those antibodies are specific to a patient's tumor cells (e.g., neoepitopes), a particular tumor type (e.g., her2neu, PSA, PSMA, etc.), or antigens associated with cancer (e.g., CEA-CAM). Advantageously, such cells may be commercially obtained from NantKwest as haNK cells (high-affinity natural killer cells) and may then be further modified (e.g., to express co-stimulatory molecules).

In further aspects, genetically engineered NK cells may also be genetically engineered to express a chimeric T cell receptor. In especially preferred aspects, the chimeric T cell receptor will have an scFv portion or other ectodomain with binding specificity against a tumor associated antigen, a tumor specific antigen, and/or a neoepitope of the patient as determined by the omics analysis. As before, such cells may be commercially obtained from NantKwest as taNK cells ('target-activated natural killer cells') and further modified as desired. Where the cells have a chimeric T cell receptor engineered to have affinity towards a cancer associated antigen or neoepitope, it is contemplated that all known cancer associated antigens and neoepitopes are considered appropriate for use. For example, tumor associated antigens include CEA, MUC-1, CYPB1, PSA, Her-2, PSA, brachyury, etc.

Moreover, it should be noted that the methods and uses contemplated herein also include cell based treatments with cells other than (or in addition to) NK cells. For example, suitable cell based treatments include T cell based treatments. Among other options, it is contemplated that one or more features associated with T cells (e.g., CD4+ T cells, CD8+ T cells, etc.) can be detected. More specifically, contemplated omics analysis can identify specific neoepitopes (e.g., 8-mers to 12-mers for MHC I, 12-mers to 25-mers for MHC II, etc.) that can be used for the identification of neoepitope reactive T cells bearing a specific T cell receptor against the neoepitopes/MHC protein complexes. Thus, the method can include harvesting the neoepitope reactive T cells. The harvested T cells can be grown or expanded (or reactivated where exhausted) ex vivo in preparation for reintroduction to the patient. Alternatively, the T cell receptor genes in the harvested T cells can be isolated and transferred into viruses, or other adoptive cell therapies systems (e.g., CAR-T, CAR-TANK, etc.). Beyond neoepitopes, the omics analyses can also provide one or more tumor associated antigens (TAAs). Therefore, one can also harvest T cells that have receptors that are sensitive to the TAAs identified from these analyses. These cells can be grown or cultured ex vivo and used in a similar therapeutic manner as discussed above. The T cells can be identified by producing synthetic versions of the peptides and bind them with commercially produced WIC or WIC-like proteins, then using these ex vivo complexes to bind to the target T cells. One should appreciated that the harvested T cells can included T cells that have been activated by the patient's immune response to the disease, exhausted T cells, or other T cells that are responsive to the discussed features.

Therefore, it should be noted that the above treatments will not only target the TME to reduce immune suppression and increase immunogenicity of the tumor cells in the TME, but also initiate or support an innate immune response. Advantageously, the innate immune response may be further enhanced using tumor antigen specific antibodies that, when bound to a tumor cell, trigger cytotoxic cell killing of NK cells. Notably, such antibodies can be targeted against known tumor associated antigens (e.g., MUC-1, HER2, brachyury, CEA, etc.) but also against patient and tumor specific neoepitopes that were previously identified using contemplated omics analyses. For example, preparation and use of neoepitope specific antibodies are exemplarily described in WO 2016/172722. Such antibody-mediated cell killing will also enhance epitope spread (i.e., presentation of new tumor cell epitope via cytotoxic cell killing), which will in turn induce or enhance an adaptive immune response.

Still further, and with further respect to antibodies that bind to a tumor cell antigen, it should be appreciated that such antibodies or fragments thereof may also be prepared as fusion proteins where the non-antibody portion is an immune stimulatory cytokine, a chemokine, a co-stimulatory molecule, or a molecule that interferes with checkpoint inhibition.

Viewed from a different perspective, tumor immunogenicity may be generated or enhanced by tumor-specific binding of stimulating or anti-immune suppressive factors. Such treatment will advantageously induce or enhance the elimination phase via at least one of innate and adaptive immune response.

With further reference to FIG. 3, adaptive immune response may also be induced using one or more vaccine compositions that are tailored to the specific patient's tumor via targeting tumor associated antigens and/or tumor neoepitopes. Where neoepitope vaccines are employed, it should be recognized that such neoepitopes advantageously are identified in the omics analyses as described above. There are various tumor vaccine compositions known in the art, and all of them are deemed suitable for use herein. However, especially preferred tumor vaccine compositions include bacterial vaccine compositions in which the bacterium is genetically engineered to express one or more tumor associated antigen and/or neoepitope. Most preferably, the recombinant bacterium is genetically engineered such that it expresses endotoxins at a low level that is insufficient to induce a CD-14 mediated sepsis in the patient. One exemplary bacteria strain with modified lipopolysaccharides includes ClearColi® BL21(DE3) electrocompetent cells. This bacteria strain is BL21 with a genotype F-ompT hsdSB (rB- mB-) gal dcm lon λ(DE3 [lacI lacUV5-T7 gene 1 ind1 sam7 nin5]) msbA148 ΔgutQΔkdsD ΔlpxLΔlpxMΔpagPΔlpxPΔeptA. In this context, it should be appreciated that several specific deletion mutations (ΔgutQ ΔlcdsD ΔlpxL ΔlpxMΔpagΔlpxΔeptA) encode the modification of LPS to Lipid $IV_A$, while one additional compensating mutation (msbA148) enables the cells to maintain viability in the presence of the LPS precursor lipid IVA. These mutations result in the deletion of the oligosaccharide chain from the LPS. Most typically, these bacteria are irradiated before administration. Similarly, numerous yeast expression systems are deemed suitable for use herein. However, especially preferred recombinant yeast systems include those based on S. cerevisiae.

In still further preferred aspects of vaccine compositions, recombinant viruses are deemed suitable, and especially recombinant adenoviral systems (such as Ad5 type) with reduced antigenicity as described in PCT/US16/65412, PCT/US17/17588, PCT/US17/23117, and WO 2016/164833. Such viruses can, for example, be prepared in a method that includes one step of identifying a cancer-related neoepitope of a patient, a further step of determining binding of the neoepitope to an HLA-type of the patient, and determining an expression level of the neoepitope, a still further step of selecting at least one co-stimulatory molecule, and a step of genetically modifying a virus to include a nucleic acid encoding the at least one co-stimulatory molecule and the cancer-related neoepitope. With respect to the virus, it is generally referred that the virus is an adenovirus or a replication deficient virus. Moreover, it is further preferred that the virus is non-immunogenic. Thus, especially preferred viruses include an adenovirus, and especially an Ad5 [E1⁻E2b⁻].

Cancer-related neoepitopes of the patient are preferably identified in silico by location-guided synchronous alignment of omics data of tumor and matched normal samples, and contemplated methods may further comprise a step of predicting the HLA type of the patient in silico. While not limiting to the inventive subject matter, it is preferred that the expression level of the neoepitope is at least 20% compared to a matched normal sample.

It is further contemplated that the recombinant entity (e.g., bacterium, yeast, virus) may also include one or more sequences that encode one or more co-stimulatory molecule, including selected from the group of B7.1 (CD80), B7.2 (CD86), CD30L, CD40, CD40L, CD48, CD70, CD112, CD155, ICOS-L, 4-1BB, GITR-L, LIGHT, TIM3, TIM4, ICAM-1, and LFA3 (CD58). Moreover, the nucleic acid may further include a sequence encoding a cytokine (e.g., IL-2, IL-7, IL-12, IL-15, an IL-15 superagonist (IL-15N72D), and/or an IL-15 superagonist/IL-15RαSushi-Fc fusion complex). Alternatively, or additionally, the nucleic acid further may also include a sequence encoding at least one component of a SMAC (e.g., CD2, CD4, CD8, CD28, Lck, Fyn, LFA-1, CD43, and/or CD45 or their respective binding counterparts). Where desired, the nucleic acid may additionally comprise a sequence encoding an activator of a STING pathway, such as a chimeric protein in which a transmembrane domain of LMP1 of EBV is fused to a signaling domain of IPS-1. Such modifications are thought to even further enhance development of an adaptive immune response by providing additional signals for activation of the adaptive immune response.

Additionally, as also depicted in FIG. 3, the equilibrium phase may be maintained or supported by administration of various cytokines and especially IL-2 and IL-15, or a IL-15 superagonist, all of which may be part of a fusion protein that has a binding portion that binds to a tumor associated antigen, a necrotic cell component (e.g., nucleolin, DNA, a histone protein, etc.), or a patient and tumor specific antigen. Such compositions advantageously activate T-cells and NK cells at the target site of the tumor. Similarly, the equilibrium phase may be maintained or supported by administration of various binders that interfere with checkpoint inhibition (e.g., PD-1 or PD-L1 binder), all of which may once more be part of a fusion protein that has a binding portion that binds to a tumor associated antigen, a necrotic cell component (e.g., nucleolin, DNA, a histone protein, etc.), or a patient and tumor specific antigen. In still further contemplated aspects of enhancing the adaptive and/or innate immune response, administration of hybrid proteins is contemplated in which the hybrid protein has a IL15/IL-15R-alpha component and an Fc component to stabilize the protein and increase serum half-life time. For example, especially preferred hybrid proteins include IL-15-based immunostimulatory protein complexes comprising two protein subunits of a human IL-15 variant associated with high affinity to a dimeric human IL-15 receptor α (IL-15Rα) sushi domain/human IgG1 Fc fusion protein (*J Immunol* (2009) 183: 3598-3607).

Finally, as also illustrated in FIG. 3, contemplated methods and uses will include steps to maintain the equilibrium phase, typically by administration of one or more inhibitors of suppressor cells such as cisplatin, gemcitabine, 5-fluorouracil, cyclophosphamide, doxorubicin, temozolomide, docetaxel, paclitaxel, trabectedin, and RP-182. Additionally, and where desired, checkpoint inhibitors can be administered.

Figure 4:
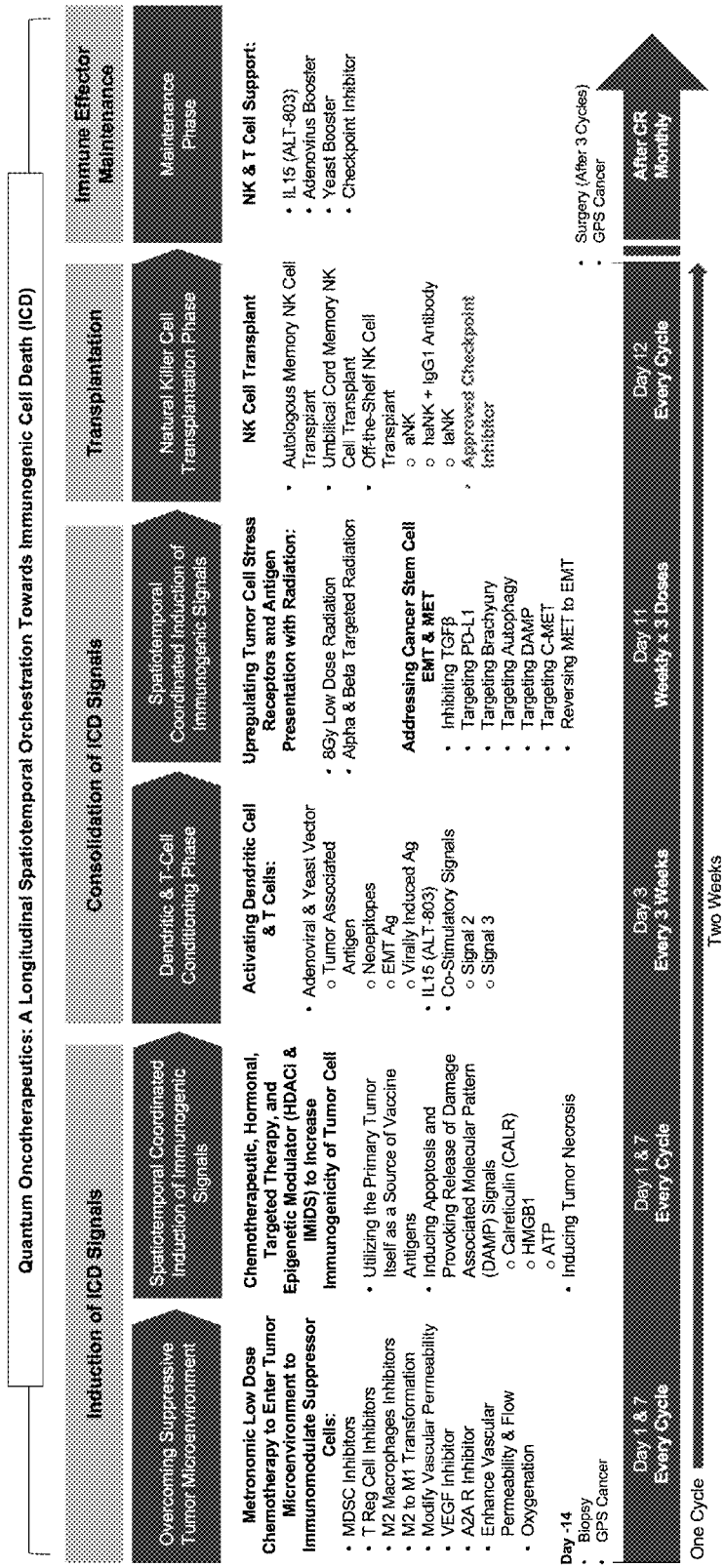
FIG. 4 is an exemplary flow chart of a treatment according to the inventive subject matter.

The spatiotemporal orchestration of treatment towards immunogenic cell death is schematically illustrated in FIG. 4. Here, treatments and uses of contemplated compounds and compositions are shown as four elements from a mechanistic point of view: Induction of ICD signals, consolidation of ICD signals, transplantation, and immune effector maintenance.

As noted above, overcoming an immune suppressive TME will lay a foundation for later or concurrent treatments that are based on innate and adaptive immune responses. To that end, metronomic low dose chemotherapy may be given to a patient to enter the TME and to immunomodulate the suppressor cells in the TME. Such phase can achieved in numerous manners, including the use of MDSC Inhibitors, T-Reg inhibitors, M2 macrophage inhibitors, stimulation of M2 to M1 transformation, modification of vascular permeability, administration of VEGF and/or A2A R inhibitors, and even tissue oxygenation to the typically hypoxic TME. Such treatment can be further augmented as noted above with various compositions to increase the TME's immunogenicity. Induction of immunogenic signals can be achieved by chemotherapeutic, hormonal, and targeted therapy, as well as by epigenetic modulation (e.g., using histone deacetylases and other IMiDS such as DNMT inhibitors, HDAC inhibitors, SirT modulators, including azacitidine, decitabine, and vorinostat, etc.) to so increase the immunogenicity of the tumor cells. Depending on the type of treatment as discussed above, the primary tumor can become a source of vaccine antigens and immune stimulation (e.g., via release of DAMP signals or expression of stress signals). Consolidation of the ICD signals is then performed via dendritic and T-cell conditioning using vaccine compositions as discussed above, typically along with immune stimulatory cytokines and/or co-stimulatory signals. Treatments may also include the upregulation of tumor cell stress, receptor and/or antigen presentation with radiation, typically at relatively low dose (e.g., <8Gy). Where desired or necessary, endothelial-to-mesenchymal transition may be modulated, preferably by binding TGF-beta and and/or IL-10 to appropriate binding molecules. Transplantation preferably comprises administration of NK cells as already discussed above. Finally, immune effector maintenance can be achieved by administration of immunostimulatory cytokines, tumor vaccine boosters, and administration of checkpoint inhibitors.

As will be readily appreciated, the methods and uses contemplated herein will be preferably accompanied by diagnostic tests to monitor treatment efficacy, and suitable diagnostic test include radiology tests, biopsies and attendant biochemical tests, omics analyses, and especially liquid biopsy. Such monitoring will allow adjustment of one or more components, especially in view of newly discovered or recently eliminated neoepitopes, newly discovered druggable targets and pathway activities, etc. In his context it should be noted that while it can take several months for disease progression to show up on an imaging test, a pan-omics approach, based on a patient's unique molecular profile and associated proteomic signaling pathway signature, disease progression can be rapidly identified, allowing a change of the therapy to occur.

Circulating tumor RNA (ctRNA), and especially ctRNA with patient- and tumor-specific mutations, can be employed as a sensitive, selective, and quantitative marker for diagnosis and monitoring of treatment, and even as discovery tool that allows repeated and non-invasive sampling of a patient. In most typical aspects, the ctRNA is isolated from a whole blood sample that is processed under conditions that preserve cellular integrity and stability of ctRNA and/or ctDNA. Notably, where ctRNA is isolated from a patient's biological fluid, miRNA (and other regulatory RNA) can also be detected and/or quantified. Most typically, upon separation of the ctRNA from non-nucleic acid components, circulating nucleic acids may then be quantified, preferably using real time quantitative PCR.

Viewed from a different perspective, it should be appreciated that various nucleic acids may be selected for detection and/or monitoring a particular disease, disease stage, treatment response in a particular patient, even before treatment has started. Advantageously, contemplated compositions and methods are independent of a priori known mutations leading to or associated with a cancer. Still further, contemplated methods also allow for monitoring clonal tumor cell populations as well as for prediction of treatment success with an immunomodulatory therapy (e.g., checkpoint inhibitors or cytokines), and especially with neoepitope-based treatments (e.g., using DNA plasmid vaccines and/or viral or yeast expression systems that express neoepitopes or polytopes).

EXAMPLES

The following description provides exemplary protocols to treat cancer in a patient according to the inventive subject matter. It should be understood that while these protocols list specific compounds and compositions alone or in combination, various alternative compounds and compositions may be provided with the same or similar effect. Moreover, dosage and schedules may change according to patient age, stage of cancer, and overall health condition.

Pharmaceutical agents and compositions: Unless otherwise noted herein, all of the compounds and compositions referred herein are known and commercially available. The compounds that are not commercially available are characterized as listed below.

ALT-803: ALT-803 is an IL-15-based immunostimulatory protein complex comprising two protein subunits of a human IL-15 variant associated with high affinity to a dimeric human IL-15 receptor α (IL-15Rα) sushi domain/human IgG1 Fc fusion protein (*J Immunol* (2009) 183: 3598-3607). The IL-15 variant is a 114 amino acid polypeptide comprising the mature human IL-15 cytokine sequence, with an asparagine to aspartate substitution at position 72 of helix C (N72D). The human IL-15Ra sushi domain/human IgG1 Fc fusion protein comprises the sushi domain of the human IL-15 receptor α subunit (IL-15Rα) (amino acids 1-65 of the mature human IL-15Ra protein) linked to the human IgG1 CH2-CH3 region containing the Fc domain (232 amino acids). Except for the N72D substitution, all of the protein sequences are human.

aNK: The aNK cell line is a human, IL-2-dependent NK cell line that was established from the peripheral blood mononuclear cells (PBMCs) of a 50-year-old male diagnosed with non-Hodgkin lymphoma (*Leukemia* 1994; 8:652-8). aNK cells are characterized by the expression of CD56bright and CD2, in the absence of CD3, CD8, and CD16. A CD56bright/CD16neg/low phenotype is typical for a minor subset of NK cells in peripheral blood, which have immunomodulatory functions as cytokine producers. Unlike normal NK cells, aNK lacks expression of most killer cell immunoglobulin-like receptors (KIR) (*J Hematother Stem Cell Res* 2001; 10:369-83). Only KIR2DL4, a KIR receptor with activating function and inhibitory potential that is expressed by all NK cells, was detected on the surface of aNK. KIR2DL4 is considered to mediate inhibitory effects through binding to the HLA allele G. The predominant pathway of cytotoxic killing of aNK cells is through the perforin/esterase pathway; aNK expresses high levels of perforin and granzyme B (*J Hematother Stem Cell Res* 2001; 10:369-83).

aNK cells have a very broad cytotoxic range and are active against cell lines derived from hematologic malignancies and solid tumors (*Biol Blood Marrow Transplant* 1996; 2:68-75). Safety assessments in severe combined immunodeficiency (SCID) mice showed no aNK treatment-related effects, such as acute toxicity or long-term carcinogenicity. Administration of aNK cells to mice challenged with human leukemia cells or mouse models of human melanoma resulted in improved survival and suppression of tumor growth, including complete remissions in some mouse tumors.

haNK: The haNK cells are NK-92 [CD16.158V, ER IL-2] derivatives (high-affinity activated natural killer cell line, [haNK™ for Infusion]) and cultured as a human, allogeneic, NK cell line that has been engineered to produce endogenous, intracellularly retained IL-2 and to express CD16, the high-affinity (158V) Fc gamma receptor (FcγRIIIa/CD16a). Phenotypically, the haNK cell line is CD56+, CD3−, and CD16+.

The haNK cell line was developed by transfecting the parental aNK cell line with a bicistronic plasmid vector containing IL-2 and the high-affinity variant of the CD16 receptor (URL: https://nantkwest.com/technology/#hank). The plasmid contains an ampicillin resistance cassette, and the promoter used for expression of the transgene is elongation factor 1 alpha (EF-1a) with an SV40 polyadenylation sequence. The plasmid was made under transmissible spongiform encephalopathies (TSE)-free production conditions and contains some human origin sequences for CD16 and IL-2, neither of which have any transforming properties. haNK™ for Infusion has enhanced CD16-targeted ADCC capabilities as a result of the insertion of the high-affinity variant of the CD16 receptor. The haNK003 master cell bank was derived from a monoclonal cell line.

Avelumab: Avelumab is a human monoclonal $IgG_1$ antibody that blocks interaction between PD-L1 and its receptor, PD-1, while leaving intact interactions between PD-L2 and PD-1 (see e.g., *Lancet Oncol.* 2016; 17:1374-1385).

ETBX-011 (Ad5 [E1-, E2b-]-CEA(6D)): ETBX-011 is a Ad5 [E1-, E2b-]-CEA(6D) is an adenovirus vector vaccine in which the E1, E2b and E3 gene regions have been removed and replaced with a gene encoding CEA with the CAP1-6D mutation (*Cancer Immunol Immunother.* 2015; 64:977-87; *Cancer Immunol Immunother.* 2013; 62:1293-301).

ETBX-021: ETBX-021 is a HER2-targeting adenovirus vector vaccine comprising the Ad5 [E1-, E2b-] vector and a modified HER2 gene insert (*Cancer gene therapy* 2011; 18:326-335). The HER2 gene insert encodes a truncated human HER2 protein that comprises the extracellular domain and transmembrane regions. The entire intracellular domain, containing the kinase domain that leads to oncogenic activity, is removed.

ETBX-051 (Ad5 [E1-, E2b-]-Brachyury): ETBX-051 is an Ad5-based adenovirus vector vaccine that has been modified by the removal of the E1, E2b, and E3 gene regions and the insertion of a modified human Brachyury gene. The modified Brachyury gene contains agonist epitopes designed to increase cytotoxic T lymphocyte (CTL) antitumor immune responses (see e.g., *Oncotarget.* 2015; 6:31344-59).

ETBX-061 (Ad5 [E1-, E2b-]-MUC1): ETBX-061 is an Ad5-based adenovirus vector vaccine that has been modified by the removal of the E1, E2b, and E3 gene regions and the insertion of a modified human MUC1 gene. The modified MUC1 gene contains agonist epitopes designed to increase CTL antitumor immune responses (see e.g., *Oncotarget.* 2015; 6:31344-59).

GI-4000 (GI-4014, GI-4015, GI-4016, GI-4020): GI-4000 is 4 separate products from the GI-4000 series, GI-4014, GI-4015, GI-4016, GI-4020. Each of these is a recombinant, heat-inactivated *S. cerevisiae* engineered to express a combination of 2-3 of the 6 mutated Ras oncoproteins. GI-4014, GI-4015, and GI-4016 products each contain two mutations at codon 61 (glutamine to arginine [Q61R], and glutamine to leucine [Q61L], plus one of three different mutations at codon 12 (either glycine to valine [G12V], glycine to cysteine [G12C], or glycine to aspartate [G12D]). GI-4020 product contains two mutations at codon 61 (glutamine to histidine [Q61H] and glutamine to leucine [Q61L]), plus one mutation at codon 12 (glycine to arginine [G12R]).

Thus, GI-4000 is manufactured as four individual products with the subnames GI-4014, GI-4015, GI-4016, and GI-4020 depending on the mutated Ras oncoprotein the product is engineered to express. The biologic product is formulated in phosphate buffered saline (PBS) for injection and vialed separately at a concentration of 20 YU/mL (1 YU=$10^7$ yeast cells). Each single use 2 mL vial contains 1.2 mL of biologic product. Two vials of drug product will be used for each GI-4000 administration visit. The specific GI-4000 product containing the Ras mutation in the subject's tumor will be used for treatment (GI-4014 for G12V, GI-4015 for G12C, GI-4016 for G12D, GI-4020 for G12R or Q61H, and GI-4014, GI-4015, or GI-4016 for Q61L or Q61R). Two syringes of 0.5 mL will be drawn from each vial, and 4 total injections will be administered for a dose of 40 YU at each dosing visit. GI-6207: GI-6207 is a heat-killed, recombinant *Saccharomyces cerevisiae* yeast-based vaccine engineered to express the full length human carcinoembryonic antigen (CEA), with a modified gene coding sequence to code for a single amino acid substitution (asparagine to aspartic acid) at the native protein amino acid position 610, which is designed to enhance immunogenicity. A plasmid vector containing the modified human CEA gene is used to transfect the parental yeast strain (*S. cerevisiae* W303—a haploid strain with known mutations from wild-type yeast) to produce the final recombinant vaccine product (see e.g., *Nat Med.* 2001; 7:625-9).

GI-6301: GI-6301 is a heat-killed, *S. cerevisiae* yeast-based vaccine expressing the human Brachyury (hBrachyury) oncoprotein. The Brachyury antigen is the full-length protein possessing an N-terminal MADEAP (Met-Ala-Asp-Glu-Ala-Pro) motif appended to the hBrachyury sequence to promote antigen accumulation within the vector and a C-terminal hexahistidine epitope tag for analysis by Western blotting (see e.g., Cancer *Immunol Res.* 2015; 3:1248-56). Expression of the hBrachyury protein is controlled by a copper-inducible CUP1 promoter.

Head and Neck Squamous Cell Cancer (HNSCC):

Head and neck cancers collectively encompass a number of malignant tumors that involve the throat, larynx, nose, sinuses, and mouth. An estimated 60,000 patients are diagnosed with head and neck cancer annually in the US and roughly half of all patients diagnosed with HNSCC die of the disease. Despite various treatment options, there remains an urgent need to improve treatment outcome and overall survival.

In general, the overall goals of the HNSCC vaccine treatment presented herein are to maximize ICD and augment and maintain the innate and adaptive immune responses against cancer cells. The rationale for the selection of agents is summarized in Table 1 in which i) denotes that tumor molecular profiling will determine whether ETBX-021 will be administered; ii) denotes that tumor molecular profiling will determine whether GI-4000 will be administered; iii) denotes that Capecitabine is metabolized to 5-FU; iv) denotes that leucovorin potentiates the activity of 5-FU; and v) denotes that either nivolumab or avelumab may be administered.

| Agent | Mitigating Immunosuppression in the TME | Inducing and Coordinating ICD Signals | Conditioning Dendritic and T Cells | Enhancing Innate Immune Responses | Maintaining Immune Responses |
|---|---|---|---|---|---|
| Non-Marketed products | | | | | |
| ALT-803 | | | X | X | |
| ETBX-011 | | | X | | |
| ETBX-021[i)] | | | X | | |
| ETBX-051 | | | X | | |
| ETBX-061 | | | X | | |
| GI-4000[ii)] | | | X | | |
| GI-6207 | | | X | | |
| GI-6301 | | | X | | |
| haNK cells | | | | X | |
| Approved products | | | | | |
| Bevacizumab | X | X | | | |
| Capecitabine[iii)] | X | X | | | |
| Cetuximab | | X | | | |
| Cisplatin | | X | | | |
| Cyclophosphamide | X | X | | | |
| 5-FU/leucovorin[iv)] | X | X | | | |
| Fulvestrant | | X | | | |
| Nab-paclitaxel | X | X | | | |
| Nivolumab/avelumab[v)] | | | | | X |
| Omega-3-acid ethyl esters | | X | | | |
| SBRT | | X | | X | |

Figure 5:
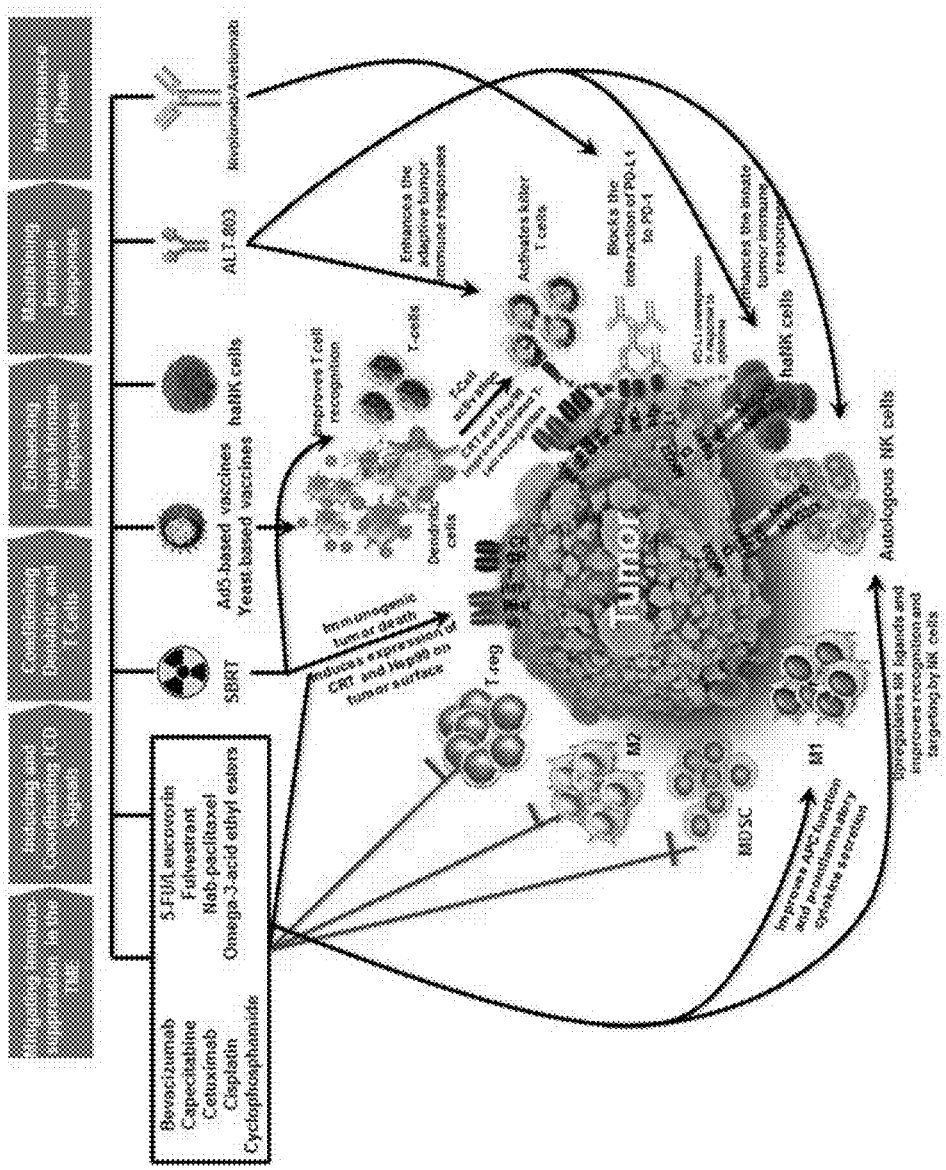
FIG. 5 is a schematic illustration of mechanism(s) by which each agent is thought to impact the immune system, consequently leading to immunogenic cell death of the tumor in the treatment of HNSCC.

FIG. 5 exemplarily and schematically depicts the mechanism(s) by which each agent is thought to impact the immune system, consequently leading to ICD. By combining agents that simultaneously (or sequentially) target distinct but complementary mechanisms that enable tumor growth, the treatment regimen aims to maximize anticancer activity and prolong the duration of response to treatment.

To that end, contemplated HNSCC treatments combine low dose metronomic chemotherapy (LDMC), bevacizumab, cetuximab, cancer vaccine(s), low-dose radiation therapy, an IL-15 superagonist, NK cell therapy, and a checkpoint inhibitor. Such treatment regimen is thought to maximize ICD and augment and maintain the innate and adaptive immune responses against cancer cells. More specifically, the treatment regimen is set up to interrupt the escape phase of immunoediting by (a) Mitigating immunosuppression in the TME. LDMC will be used to reduce the density of Tregs, MDSCs, and M2 macrophages contributing to immunosuppression in the TME. Bevacizumab will be used to cause morphological changes in the TME to promote lymphocyte trafficking; (b) Inducing and coordinating ICD signals. LDMC and low-dose radiation therapy will be used to increase the antigenicity of tumor cells. Bevacizumab will be used to alter the TME, which allows for more efficient antigen-specific T-cell responses and makes tumor cells more susceptible to ICD. Cetuximab and fulvestrant will be used to enhance ADCC and cytotoxic T-cell activity; (c) Conditioning dendritic and T cells. Cancer vaccine(s) and an IL-15 superagonist will be used to enhance tumor-specific cytotoxic T-cell responses; (d) Enhancing innate immune responses. NK cell therapy will be used to augment the innate immune system. An IL-15 superagonist will be used to enhance the activity of endogenous and introduced NK cells. Low-dose radiation therapy will be used to stimulate the activity of NK cells; and (e) Maintaining immune responses. A checkpoint inhibitor will be used to promote long-term anticancer immune responses.

Figure 6:
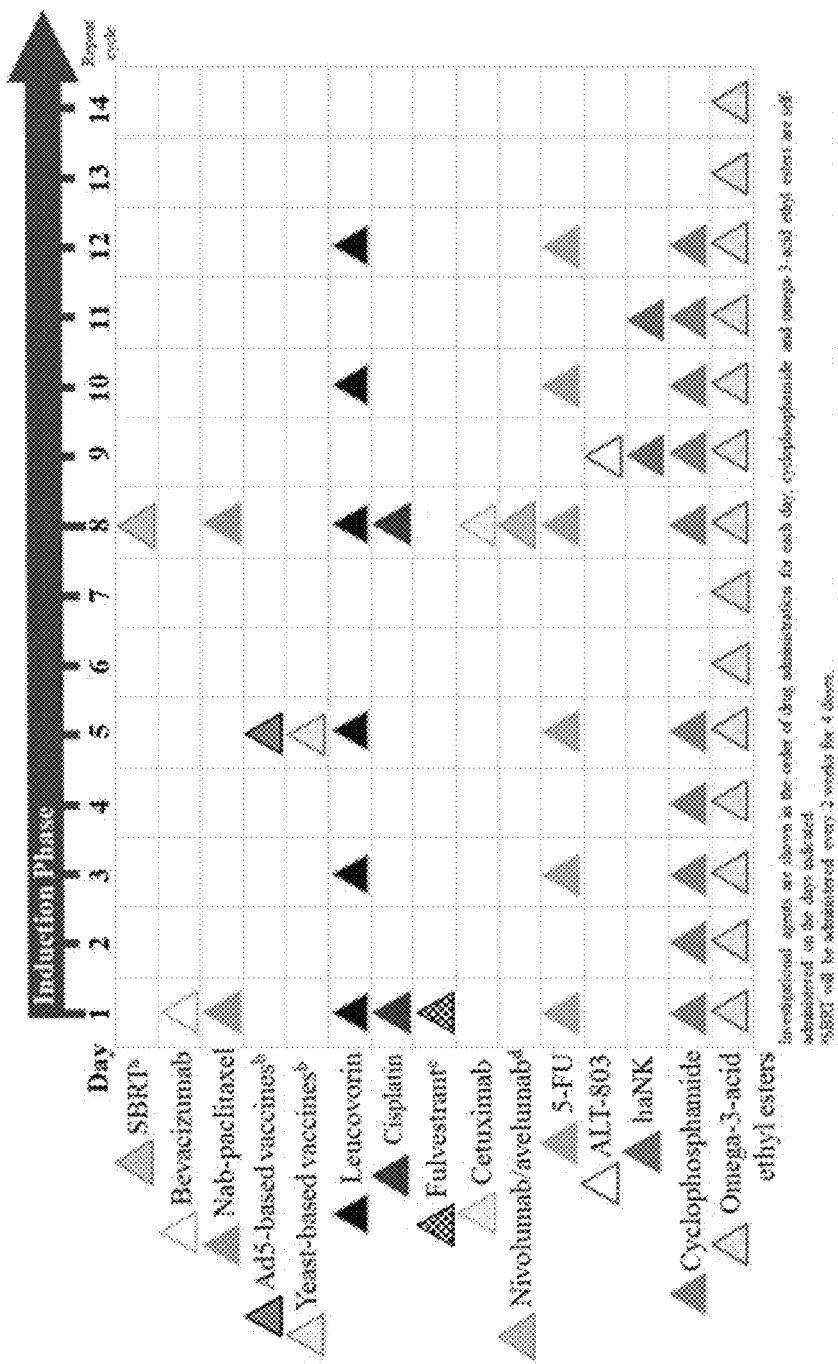
FIG. 6 is a flow chart for administration of various pharmaceutical compositions during the induction phase in the treatment of HNSCC.
Figure 7:
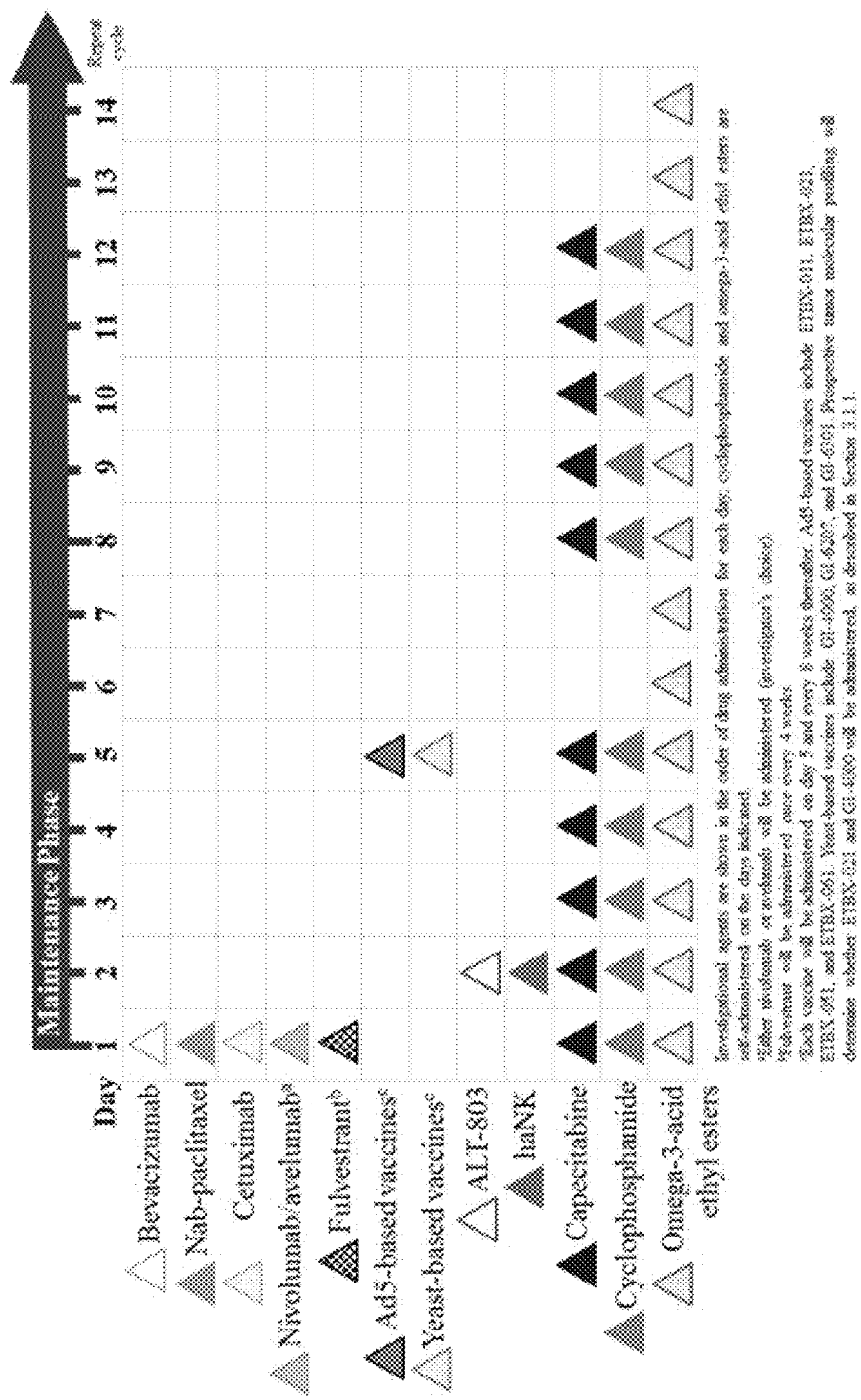
FIG. 7 is a flow chart for administration of various pharmaceutical compositions during the maintenance phase in the treatment of HNSCC.

The HNSCC vaccine treatment will be conducted in 2 phases: an induction phase and a maintenance phase. The purpose of the induction phase is to stimulate immune responses against tumor cells and mitigate immunosuppression in the TME. The purpose of the maintenance phase is to sustain ongoing immune system activity against tumor cells, creating durable treatment responses. Exemplary use and timing of administration of contemplated compounds and compositions for the induction phase and the maintenance phase are shown in FIG. 6 and FIG. 7, respectively. Therefore, the following agents and compositions are preferably used for the induction and maintenance phases:

1. ALT-803, recombinant human super agonist IL-15 complex (also known as IL 15N72D1L-15RαSu/IgG1 Fc complex); 2. ETBX-011 (Ad5 [E1-, E2b-]-CEA); 3. ETBX-021 (Ad5 [E1-, E2b-]-HER2); 4. ETBX-051 (Ad5 [E1-, E2b-]-Brachyury); 5. ETBX-061 (Ad5 [E1-, E2b-]-MUC1); 6. GI-4000 (Ras yeast vaccine); 7. GI-6207 (CEA yeast vaccine); 8. GI-6301 (Brachyury yeast vaccine); 9. haNK™, NK-92 [CD16.158V, ER IL-2], Suspension for IV Infusion (haNK™ for Infusion); 10. Avelumab (BAVENCIO® injection, for IV use); 11. Bevacizumab (AVASTIN® solution for IV infusion); 12. Capecitabine (XELODA® tablets, for oral use); 13. Cetuximab (ERBITUX® injection, for IV infusion); 14. Cisplatin (CISplatin injection); 15. Cyclophosphamide (CYCLOPHOSPHAMIDE Capsules, for oral use); 16. 5-FU (Fluorouracil Injection, for IV use only); 17. Fulvestrant (FASLODEX® for injection); 18. Leucovorin (LEUCOVORIN Calcium for Injection, for IV or IM use); 19. Nab-paclitaxel (ABRAXANE® for Injectable Suspension [paclitaxel protein-bound particles for injectable suspension] [albumin-bound]); 20. Nivolumab (OPDIVO® injection, for IV use); 21. Omega-3-acid ethyl esters (Lovaza capsules, for oral use); and 22. stereotactic body radiotherapy (SBRT).

More specifically, an exemplary treatment protocol for HNSCC will typically include the following steps, phases, compounds and compositions:

Tumors will be assessed at screening, and tumor response will be assessed every 8 weeks during the induction phase, and every 3 months during the maintenance phase by computed tomography (CT), magnetic resonance imaging (MM), or positron emission tomography (PET)-CT of target and non-target lesions in accordance with Response Evaluation Criteria in Solid Tumors (RECIST) Version 1.1 and immune-related response criteria (irRC).

Prospective Tumor Molecular Profiling: Prospective tumor molecular profiling will be conducted to inform HER2 expression and Ras mutational status and will be used to determine whether ETBX-021 and GI-4000 will be administered. All subjects will receive ETBX-011, ETBX-051, ETBX-061, GI-6207, and GI-6300 regardless of their tumor molecular profile. Prospective tumor molecular profiling will be performed on FFPE tumor tissue and whole blood (subject-matched normal comparator against the tumor tissue) collected at screening. Subjects will receive ETBX-021 if their tumor overexpresses HER2 (>750 attomole/µg of tumor tissue, as determined by quantitative proteomics with mass spectrometry). Subjects will receive GI-4000 if their tumor is positive for specific Ras mutations, as determined by whole genome sequencing. As noted above, GI-4000 is 4 separate products from the GI-4000 series (GI-4014, GI-4015, GI-4016, and GI-4020); each of these expresses a combination of mutated Ras oncoproteins. The specific Ras mutation will determine which GI-4000 product will be used for treatment (GI-4014 for G12V, GI-4015 for G12C, GI-4016 for G12D, GI-4020 for G12R or Q61H, and GI-4014, GI-4015, or GI-4016 for Q61L or Q61R).

Induction Phase: The induction phase will comprise repeated 2-week cycles for a maximum treatment period of 1 year. The treatment regimen of omega-3-acid ethyl esters, cyclophosphamide, cisplatin, 5 FU/leucovorin, nab-paclitaxel, bevacizumab, ALT-803, haNK cells, Ad5-based vaccines (ETBX-011, ETBX-021, ETBX-051, and ETBX-061), yeast-based vaccines (GI-4000, GI-6207, and GI-6301), nivolumab or avelumab, fulvestrant, cetuximab, and radiation therapy will be repeated every 2 weeks. Concurrent SBRT will be given during the first four 2-week cycles. Radiation will be administered to all feasible tumor sites using SBRT. Specifically, an exemplary induction phase of the treatment will be conducted in accordance with the following dosing regimen:

Daily:
Omega-3-acid ethyl esters (by mouth [PO] BID [3×1 g capsules and 2×1 g capsules])
Day 1, every 2 weeks:
Bevacizumab (5 mg/kg IV)
Day 1, every 4 weeks (every other treatment cycle):
Fulvestrant (500 mg IM)
Days 1-5 and 8-12, every 2 weeks:
Cyclophosphamide (50 mg PO twice a day [BID]).
Days 1, 3, 5, 8, 10 and 12, every 2 weeks:
5-FU (400 mg/m2 continuous IV infusion over 24 hours)
Leucovorin (20 mg/m2 IV bolus)

Day 1 and 8, every 2 weeks:
Nab-paclitaxel (100 mg IV)
Cisplatin (40 mg/m2 IV)
Day 5, 19, 33 (every 2 weeks for 3 doses then every 8 weeks thereafter):
  ETBX-011, ETBX-021, ETBX-051, ETBX-061 ($5\times10^{11}$ virus particles [VP]/vaccine/dose subcutaneously [SC])
  GI-4000, GI-6207, GI-6301, (40 yeast units [YU]/vaccine/dose SC), 2 hours after administration of the Ad5-based vaccines Prospective tumor molecular profiling will determine whether ETBX-021 and GI-4000 will be administered, as described above.

Day 8, every week:
Cetuximab (250 mg IV)
Day 8, every 2 weeks:
Nivolumab (3 mg/kg IV over 1 hour) or avelumab (10 mg/kg IV over 1 hour).
Day 8, 22, 36, 50 (every 2 weeks for 4 doses):
SBRT (not to exceed 8 Gy, exact dose to be determined by the radiation oncologist)
Day 9, every 2 weeks:
ALT-803 (10 m/kg SC 30 minutes prior to aNK infusion)
Day 9 and 11, every 2 weeks:
haNK ($2\times10^9$ cells/dose IV)

Maintenance Phase:
The duration of the maintenance phase will be up to 1 year following completion of the last treatment in the induction phase. The maintenance phase will comprise repeated 2-week cycles. The treatment regimen of omega-3-acid ethyl esters, cyclophosphamide, capecitabine, nab-paclitaxel, bevacizumab, ALT-803, haNK cells, Ad5-based vaccines (ETBX-011, ETBX-021, ETBX-051, and ETBX-061), yeast-based vaccines (GI-4000, GI-6207, and GI-6301), nivolumab or avelumab, fulvestrant, and cetuximab will be repeated every 2 weeks.

The maintenance phase of the treatment will be conducted in accordance with the following dosing regimen:
Daily:
Omega-3-acid ethyl esters (by mouth [PO] BID [$3\times1$ g capsules and $2\times1$ g capsules])
Day 1, every 2 weeks:
Bevacizumab (5 mg/kg IV)
Nab-paclitaxel (100 mg IV)
Nivolumab (3 mg/kg IV over 1 hour) or avelumab (10 mg/kg IV over 1 hour).
Cetuximab (250 mg IV)
Day 1, every 4 weeks (every other treatment cycle):
Fulvestrant (500 mg IM)
Days 1-5 and 8-12, every 2 weeks:
Capecitabine (650 mg/m2 PO BID)
Cyclophosphamide (50 mg PO BID)
Day 2, every 2 weeks:
ALT-803 (10 μg/kg SC) (30 minutes prior to aNK infusion)
haNK ($2\times10^9$ cells/dose IV)
Day 5, every 8 weeks thereafter:
ETBX-011, ETBX-021, ETBX-051, ETBX-061 ($5\times10^{11}$ VP/vaccine/dose SC)
GI-4000, GI-6207, GI-6301 (40 YU/vaccine/dose SC), 2 hours after administration of Ad-5 based vaccines.

Figure 8:
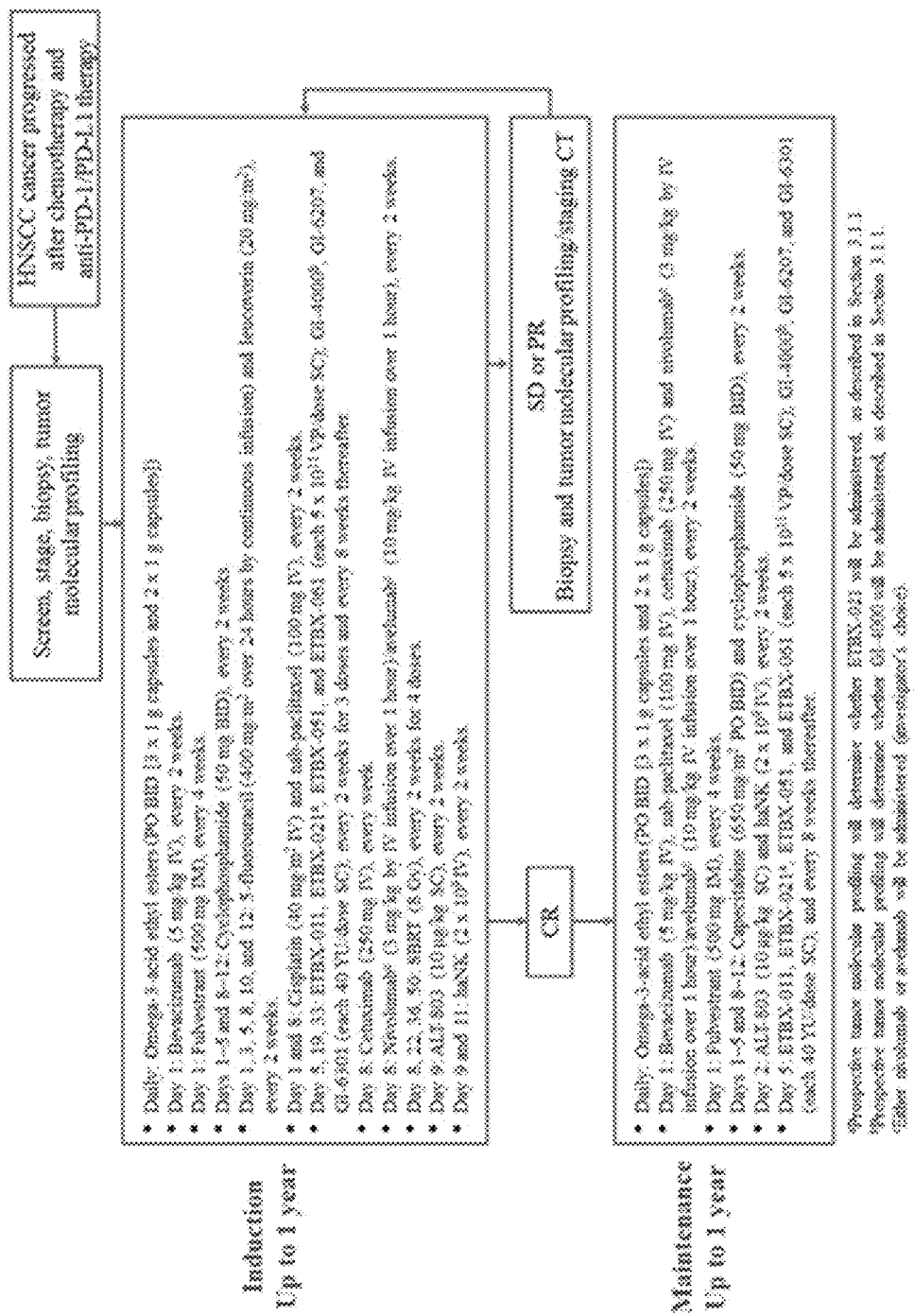
FIG. 8 is a schematic illustration of a treatment regimen for HNSCC according to the inventive subject matter.

Prospective tumor molecular profiling will determine whether ETBX-021 and GI-4000 will be administered, as described above. FIG. 8 schematically illustrates the exemplary treatment protocol.

Tumor Molecular Profiling: Genomic sequencing of tumor cells from tissue relative to non-tumor cells from whole blood will be conducted to identify tumor-specific genomic variances that may contribute to disease progression and/or response to treatment. RNA sequencing will be conducted to provide expression data and give relevance to DNA mutations. Quantitative proteomics analysis will be conducted to determine the absolute amounts of specific proteins, to confirm expression of genes that are correlative of disease progression and/or response, and to determine cutoff values for response. All genomic, transcriptomic, and proteomic molecular analyses will be exploratory, except for the prospective tumor molecular analysis of HER2 expression by quantitative proteomics and analysis of Ras mutational status by genomic sequencing to determine whether ETBX-021 and GI-4000 will be administered.

Follow-up Analyses/Sample Collection and Analysis: Tumor molecular profiling will be performed on FFPE tumor tissue and whole blood (subject-matched normal comparator against the tumor tissue) by next-generation sequencing and mass spectrometry-based quantitative proteomics. Tumor tissue and whole blood samples will be collected and shipped in accordance with the instruction cards included in the Tissue Specimen Kit and Blood Specimen Kit. The specimen requirements and procedural instructions for sample collection are described in the NantOmics Sample Collection Manual. An FFPE tumor tissue specimen is required for the extraction of tumor DNA, tumor RNA, and tumor protein. A whole blood sample is required for the extraction of subject normal DNA. Tumor tissue and whole blood will be processed in CLIA-certified and CAP-accredited clinical laboratories.

Exploratory Immunology Analysis: One aim of immunotherapy treatment is to generate antigen-specific antitumor immune responses. Exploratory immunology analysis will be used to provide a preliminary assessment of immune responses induced by the treatments. Blood samples for immune analysis will be collected from subjects at screening and every month in the induction phase and every 2 months in the maintenance phase during routine blood draws. PBMCs isolated by Ficoll-Hypaque density gradient separation will be analyzed for antigen-specific immune responses using ELISpot assays for IFN-γ or granzyme B secretion after exposure to the following tumor-associated antigen peptides: CEA, Brachyury, and MUC1, and if ETBX-021 and GI-4000 are administered, HER2 and mutant Ras, respectively. Flow cytometry will be utilized to assess T-cell responses using intracellular cytokine staining assay for IFN-γ or TNF-α expression after exposure to the tumor-associated antigen peptides. Flow cytometry analysis for the expression of CD107a on cells will be utilized to test for degranulating cells such as CD8+ T cells and NK cells. PBMCs will be stimulated in vitro with overlapping 15-mer peptide pools encoding the tumor-associated antigens mentioned above. Control peptide pools will involve the use of irrelevant antigen peptide pools as a negative control and CEFT peptide mix as a positive control. CEFT is a mixture of peptides of CMV, Epstein-Barr virus, influenza, and tetanus toxin. Post-stimulation analyses of CD4+ and CD8+ T cells will involve the production of IFN-γ, TNF-α, and CD107a expression. Sera will be analyzed for antibodies directed to the aforementioned tumor-associated antigens, neutralizing antibody titer to adenovirus (serotype 5), and for potential antibody development against the IL-15N72D:IL15RαSu/IgG1 Fc complex.

Circulating Tumor DNA and RNA Assays: Tumors evolve during therapy, and drug-resistant cells emerge, which are difficult to detect and may cause the tumor to become resistant to the initial treatment. Blood-based testing for ctDNA and ctRNA can track the emergence of drug-resistant tumor cells and can identify new drug targets and treatment options for patients. Whole blood will be collected at screening and every month in the induction phase and every 2 months in the maintenance phase during routine blood draws for the analysis of ctDNA and ctRNA. Expression levels of specific tumor- and immune-related analytes in ctDNA and ctRNA will be measured by qPCR and analyzed for correlations with subject outcomes.

Merkel Cell Carcinoma:

Skin cancer is the most common malignancy diagnosed in the United States, with more than 2 million Americans diagnosed annually. Merkel cell carcinoma (MCC) is a rare and aggressive type of skin cancer that was thought to arise from Merkel cells located between the dermal and epidermal layers of the skin. Approximately 1,500 new cases were expected in 2007 in the US. MCC is more common in whites, individuals >65 years old, men, and subjects with acquired (e.g., HIV infection) or iatrogenic immune suppression (e.g., due to treatment of autoimmune diseases). Ultraviolet exposure is an independent risk factor for the disease and may contribute to the rising incidence of MCC.

loco-regional disease. Some studies have demonstrated high objective antitumor responses (>50%) using cytotoxic chemotherapy (etoposide-carboplatin and cyclophosphamide-doxorubicin-vincristine-prednisone have been the most frequently used) in subjects with metastatic MCC. However, these responses are rarely durable, and are associated with a median OS of 9 months. Moreover, high rates of chemotoxic death were associated with first-line treatments. At present, limited data exist to guide treatment decisions regarding chemotherapy and radiotherapy, and often decisions are made based on comorbidities and consideration of AEs. For subjects with metastatic MCC, limited treatment options and limited efficacy of available therapies emphasize the need for additional therapeutic options.

In general, the overall goals of the Merkel Cell Carcinoma vaccine treatment are to maximize ICD and augment and maintain the innate and adaptive immune responses against cancer cells. The rationale for the selection of agents is summarized in Table 2 in which 5-FU is 5-fluorouracil; haNK is high-affinity activated natural killer; ICD is immunogenic cell death; SBRT is stereotactic body radiation therapy, and TME is tumor microenvironment.

| Agent | Mitigating Immunosuppression in the TME | Inducing and Coordinating ICD Signals | Conditioning Dendritic and T Cells | Enhancing Innate Immune Responses | Maintaining Immune Responses |
|---|---|---|---|---|---|
| ALT-803 | | | | X | X |
| Avelumab | | | | | X |
| Bevacizumab | X | X | | | |
| Capecitabine | X | X | | | |
| Cisplatin | | X | | | |
| Cyclophosphamide | X | X | | | |
| ETBX-051 | | | X | | |
| ETBX-061 | | | X | | |
| 5-FU | X | X | | | |
| GI-6301 | | | X | | |
| haNK cells | | | | X | |
| Nab-paclitaxel | X | X | | | |
| Omega-3-acid ethyl esters | | X | | | |
| SBRT | | X | | X | |

MCC that is confined to the skin has a good prognosis and can often be cured by surgery alone. The 5 year OS rate for subjects presenting with local disease is 66% for tumors <2 cm and 51% for tumors >2 cm. Metastatic MCC has a much poorer prognosis, with 5-year OS of 39% for subjects with regional lymph node involvement and 18% for those with metastases to distant organs. Advanced disease stage, location in the perineum or lower extremities, male gender, advanced age (>60 years old), immunosuppression, comorbid factors, high mitotic rate, and angiolymphatic invasion are associated with poor prognosis. Surgical resection is the cornerstone of therapy for MCC, with the goal of establishing clear surgical margins by wide local excision. Adjuvant radiation therapy to the primary tumor bed in subjects with stage I/II MCC has been shown to improve OS, however, neither systemic chemotherapy nor radiation therapy in subjects with stage III disease improves OS, although some studies suggest chemotherapy may increase survival in subjects with advanced MCC.

Figure 9:
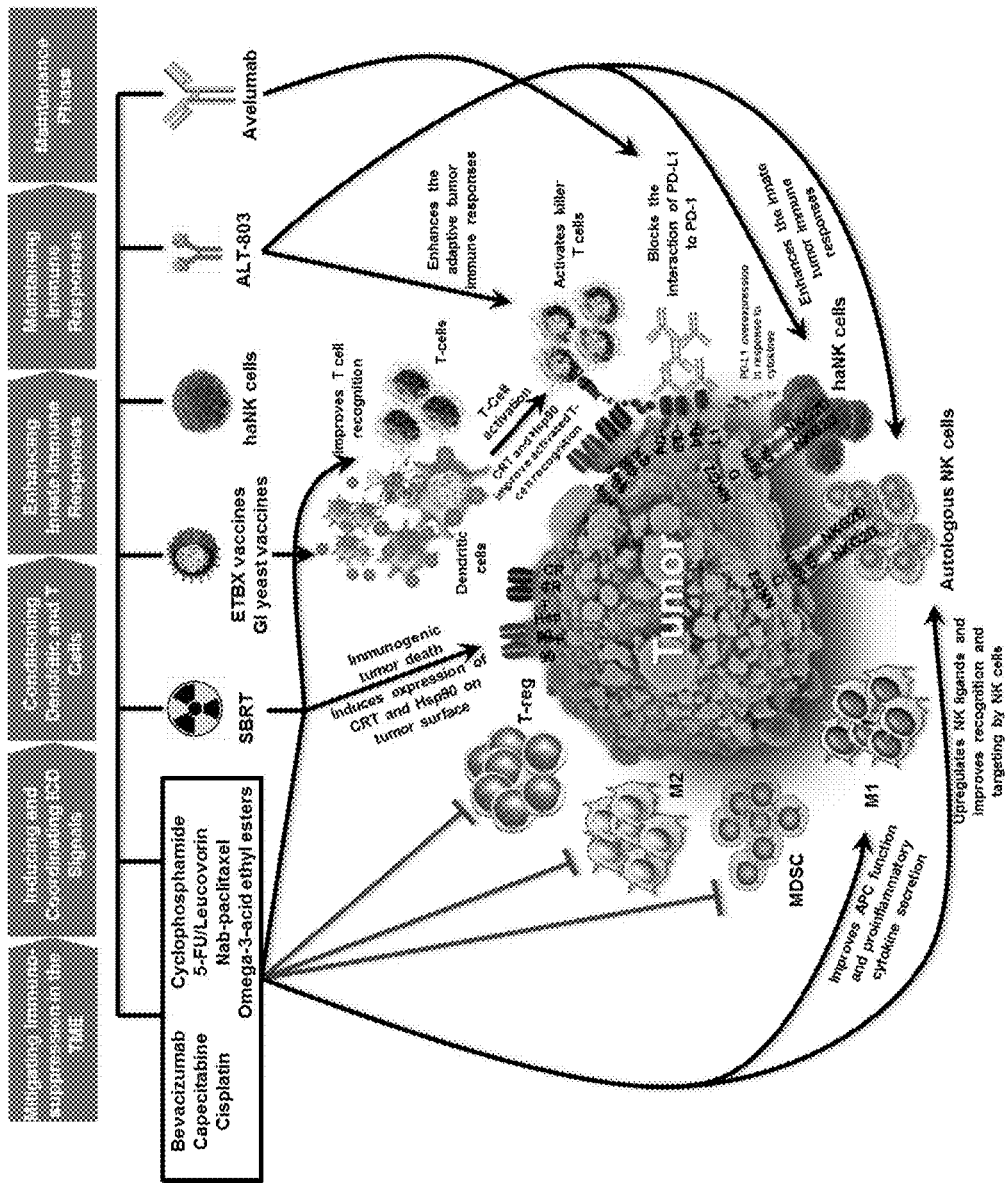
FIG. 9 is a schematic illustration of mechanism(s) by which each agent is thought to impact the immune system, consequently leading to immunogenic cell death of the tumor in the treatment of MCC.

Cytotoxic chemotherapy is often used to treat metastatic MCC. A minority of subjects treated with chemotherapy respond well to treatment, but responses are usually transient and rarely lead to significant increases in survival time. Adjuvant treatment with etoposide and carboplatin has not been associated with OS benefit for subjects with advanced FIG. 9 exemplarily and schematically depicts the mechanism(s) by which each agent impacts the immune system, consequently leading to ICD. By combining agents that simultaneously (or sequentially) target distinct but complementary mechanisms that enable tumor growth, the treatment regimen aims to maximize anticancer activity and prolong the duration of response to treatment.

To that end, contemplated MCC treatments combine LDMC, bevacizumab, a cancer vaccine, low-dose radiation therapy, an IL-15 superagonist, NK cell therapy, and a checkpoint inhibitor. Such treatment is thought to maximize ICD and augment and maintain the innate and adaptive immune responses against cancer cells. More specifically, the treatment regimen is set up to interrupt the escape phase of immunoediting by: (a) Mitigating immunosuppression in the TME. LDMC will be used to reduce the density of Tregs, MDSCs, and M2 macrophages contributing to immunosuppression in the TME. Bevacizumab will be used to cause morphological changes in the TME to promote lymphocyte trafficking; (b) Inducing and coordinating ICD signals. LDMC and low-dose radiation therapy will be used to increase the antigenicity of tumor cells. Bevacizumab will be used to alter the TME, which allows for more efficient antigen-specific T-cell responses and makes tumor cells more susceptible to ICD. Omega-3-acid ethyl esters enhances ICD without increasing toxicity; (c) Conditioning dendritic and T cells. A cancer vaccine and an IL-15 superagonist will be used to enhance tumor-specific cytotoxic T-cell responses; (d) Enhancing innate immune responses. NK cell therapy will be used to augment the innate immune system. An IL-15 superagonist will be used to enhance the activity of endogenous and introduced NK cells. Hypofractionated-dose radiation therapy will be used to upregulate tumor cell NK ligands to enhance tumor cytotoxicity of NK cells; and (e) Maintaining immune responses. A checkpoint inhibitor will be used to promote long-term anticancer immune responses.

Figure 10:
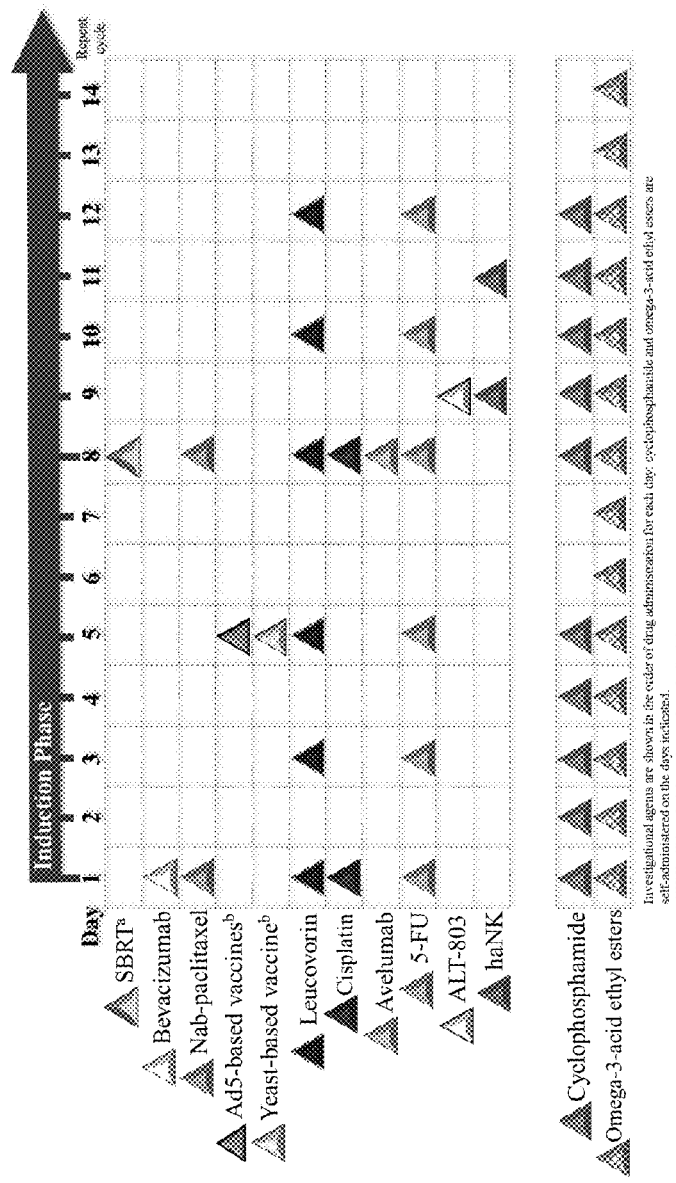
FIG. 10 is a flow chart for administration of various pharmaceutical compositions during the induction phase in the treatment of MCC.
Figure 11:
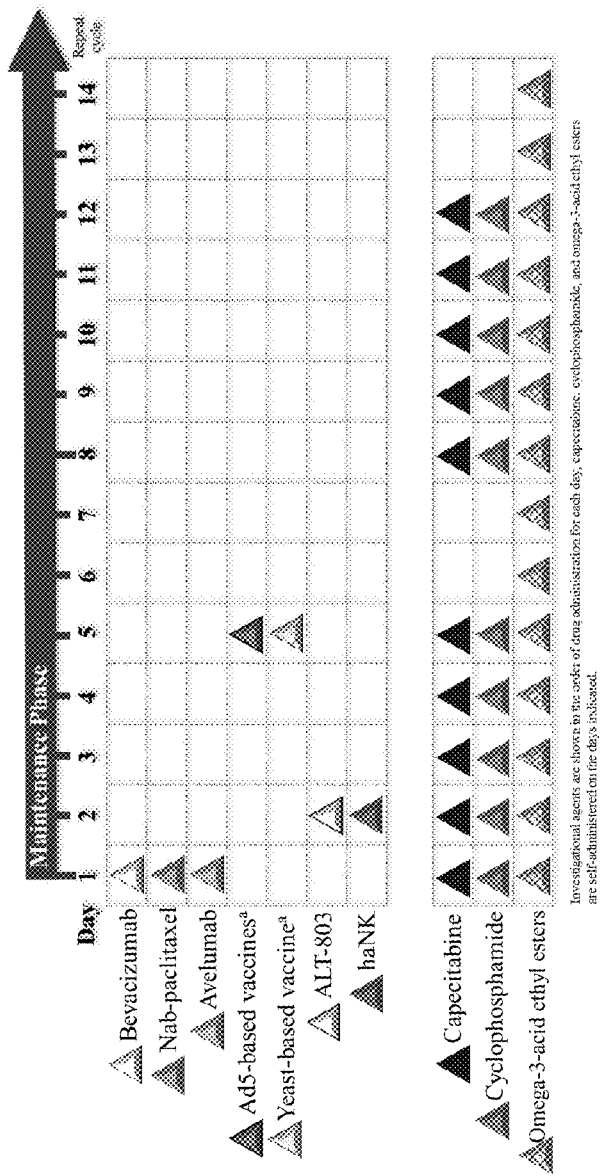
FIG. 11 is a flow chart for administration of various pharmaceutical compositions during the maintenance phase in the treatment of MCC.

The MCC vaccine treatment will be conducted in 2 phases: an induction phase and a maintenance phase. The purpose of the induction phase is to stimulate immune responses against tumor cells and mitigate immunosuppression in the TME. The purpose of the maintenance phase is to sustain ongoing immune system activity against tumor cells, creating durable treatment responses. Exemplary use and timing of of administration of contemplated compounds and compositions for the induction phase and the maintenance phase are shown in FIG. 10 and FIG. 11, respectively. Therefore, the following agents and compositions are preferably used for the induction and maintenance phases:

1. ALT-803, recombinant human super agonist interleukin-15 (IL-15) complex (also known as IL 15N72D1L-15RαSu/IgG1 Fc complex); 2. Avelumab (BAVENCIO® injection, for IV use); 3. Bevacizumab (AVASTIN® solution for IV infusion); 4. Capecitabine (XELODA® tablets, for oral use); 5. Cisplatin (CISplatin injection); 6. Cyclophosphamide (CYCLOPHOSPHAMIDE Capsules, for oral use); 7. ETBX-051 (Ad5 [E1-, E2b-]-Brachyury); 8. ETBX-061 (Ad5 [E1-, E2b-]-MUC1); 9. 5-FU (Fluorouracil Injection, for IV use only); 10. GI-6301 (Brachyury yeast vaccine); 11. haNK™, NK-92 [CD16.158V, ER IL-2], Suspension for Intravenous Infusion (haNK™ for Infusion); 12. Leucovorin (LEUCOVORIN Calcium for Injection, for IV or IM use); 13. Nab-paclitaxel (ABRAXANE® for Injectable Suspension [paclitaxel protein-bound particles for injectable suspension] [albumin-bound]); 14. Omega-3-acid ethyl esters (Lovaza capsules, for oral use); and 15. SBRT.

More specifically, an exemplary treatment protocol for MCC will typically include the following steps, phases, compounds and compositions:

Tumors will be assessed at screening, and tumor response will be assessed every 8 weeks during the induction phase and every 12 weeks during the maintenance phase by computed tomography (CT), magnetic resonance imaging (MM), or positron emission tomography-computed tomography (PET CT) of target and non-target lesions in accordance with Response Evaluation Criteria in Solid Tumors (RECIST) Version 1.1 and immune-related response criteria (irRC).

Tumor biopsies and exploratory tumor molecular profiling will be conducted at screening, at the end of the initial induction phase (8 weeks after the start of treatment), and during potential prolonged induction and maintenance phases (depending on response). Separate blood tubes will be collected every month in the induction phase and every 2 months in the maintenance phase during routine blood draws for exploratory immunology and ctDNA/ctRNA analyses.

Induction Phase: The induction phase will comprise of repeated 2 week cycles. The treatment regimen of omega-3-acid ethyl esters, cyclophosphamide, cisplatin, 5 FU/leucovorin, nab-paclitaxel, bevacizumab, ALT-803, haNK cells, Ad5-based vaccines (ETBX-051 and ETBX-061), GI-6301 yeast vaccine and avelumab will be repeated every 2 weeks. Concurrent SBRT will be given during the first four 2-week cycles. Radiation will be administered to all feasible tumor sites using SBRT. Contemplated techniques include linear-accelerator based therapies (3D and intensity-modulated radiation therapy [IMRT]). Specifically, the induction phase of the treatment will be conducted in accordance with the following dosing regimen:

Day 1, daily:
Omega-3-acid ethyl esters (5×1 g capsules by mouth [PO])
Day 1, every 2 weeks:
Bevacizumab (5 mg/kg IV)
Days 1-5 and 8-12, every 2 weeks:
Cyclophosphamide (50 mg PO twice a day [BID]).
Days 1, 3, 5, 8, 10 and 12, every 2 weeks:
5-FU (400 mg/m2 as a continuous IV infusion over 24 hours)
Leucovorin (20 mg/m2 IV bolus)
Day 1 and 8, every 2 weeks:
Nab-paclitaxel (100 mg IV)
Cisplatin (40 mg/m2 IV)
Day 5, 19, 33 (every 2 weeks for 3 doses then every 8 weeks thereafter):
ETBX-051, ETBX-061 ($5 \times 10^{11}$ virus particles [VP]/vaccine/dose subcutaneously [SC])
GI-6301 (40 yeast units [YU]/dose SC), 2 hours after administration of Ad5-based vaccines
Day 8, every 2 weeks:
Avelumab (10 mg/kg IV over 1 h)
Day 8, 22, 36, 50 (every 2 weeks for 4 doses):
SBRT (not to exceed 8 Gy, exact dose to be determined by the radiation oncologist)
Day 9, every 2 weeks:
ALT-803 (10 m/kg SC 30 minutes prior to haNK infusion)
Day 9 and 11, every 2 weeks:
haNK ($2 \times 10^9$ cells/dose IV)

Figure 12:
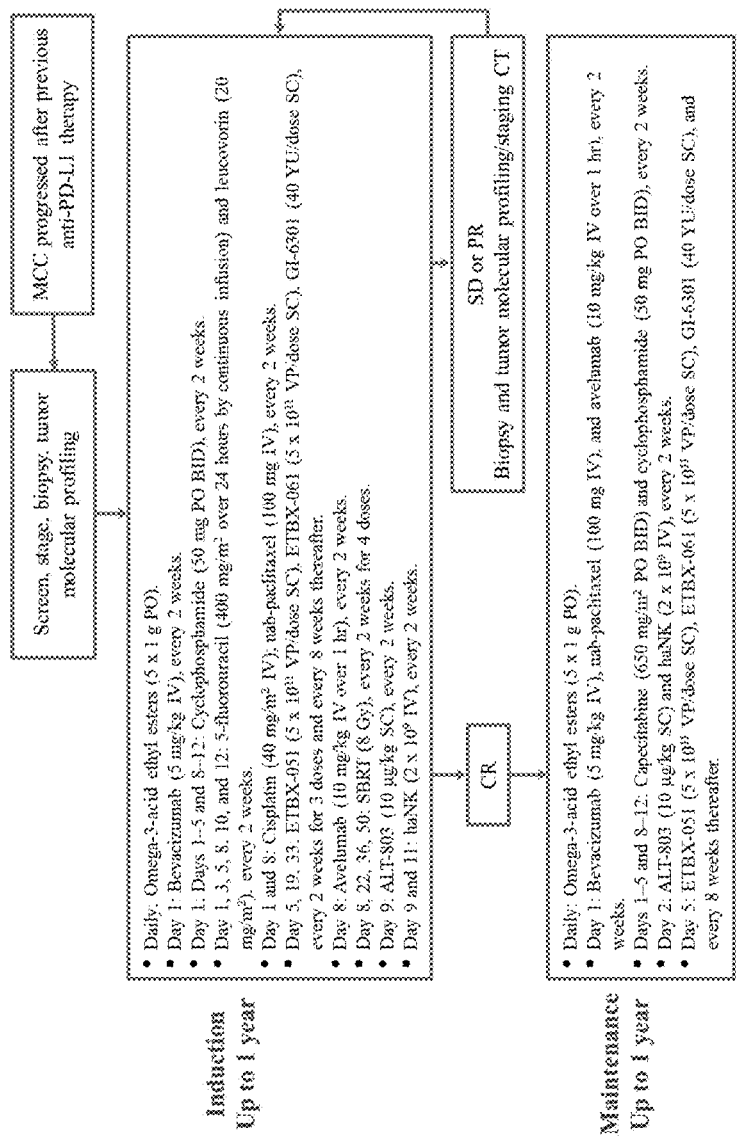
FIG. 12 is a schematic illustration of a treatment regimen for MCC according to the inventive subject matter.

Maintenance Phase: The maintenance phase of the treatment will be conducted in accordance with the following dosing regimen:

Day 1, daily:
Omega-3-acid ethyl esters (5×1 g capsules PO)
Day 1, every 2 weeks:
Bevacizumab (5 mg/kg IV)
Nab-paclitaxel (100 mg IV)
Avelumab (10 mg/kg IV over 1 hour)
Days 1-5 and 8-12, every 2 weeks:
Cyclophosphamide (50 mg PO BID)
Capecitabine (650 mg/m2 PO BID)
Day 2, every 2 weeks:
ALT-803 (10 µg/kg SC) (30 minutes prior to haNK infusion)
haNK ($2 \times 10^9$ cells/dose IV)
Day 5, every 8 weeks thereafter:
ETBX-051, ETBX-061 ($5 \times 10^{11}$ VP/vaccine/dose SC)
GI-6301 (40 YU/dose SC), 2 hours after administration of Ad5-based vaccines FIG. 12 schematically illustrates the exemplary treatment protocol.

Tumor molecular profiling before, during, and after treatment will be performed on FFPE tumor tissue and whole blood (subject-matched normal comparator against tumor tissue) by next-generation sequencing and mass spectrometry-based quantitative proteomics.

Follow-up analyses/Sample collection and Analysis: Most typically, an FFPE tumor tissue specimen is required for the extraction of tumor DNA, tumor RNA, and tumor protein, and a whole blood sample is required for the extraction of subject normal DNA. Tumor tissue and whole blood will be processed in CLIA-certified and CAP-accredited clinical laboratories.

Exploratory Immunology Analysis: One aim of immunotherapy treatment is to generate antigen-specific antitumor immune responses. Exploratory immunology analysis will be used to provide a preliminary assessment of immune responses induced by the treatments. Blood samples for immune analysis will be collected from subjects at screening/baseline and every month in the induction phase and every 2 months in the maintenance phase during routine blood draws. A sample of 10.0 mL is required at the blood draw. PBMCs isolated by Ficoll-Hypaque density gradient separation will be analyzed for antigen-specific immune responses using ELISpot assays for IFN-γ or granzyme B secretion after exposure to Brachyury and MUC1 peptides. Flow cytometry will be utilized to assess T cell responses using intracellular cytokine staining assay for IFN-γ or TNF-α expression after exposure to Brachyury and MUC1 peptides. Flow cytometry analysis for the expression of CD107a on cells will be utilized to test for degranulating cells such as CD8+ T cells and NK cells (Kannan 1996). PBMCs will be stimulated in vitro with overlapping 15-mer peptide pools encoding Brachyury and MUC1. Control peptide pools will involve the use of irrelevant antigen peptide pools as a negative control and CEFT peptide mix as a positive control. CEFT is a mixture of peptides of cytomegalovirus, EBV, influenza, and tetanus toxin. Post-stimulation analyses of CD4 and CD8 T cells will involve the production of IFN-γ, TNF-α, and CD107a expression. Sera will be analyzed for Brachyury- and MUC1 directed antibodies, neutralizing antibody titer to adenovirus (serotype 5), and for potential antibody development against the IL-15N72D1L-15RαSu/IgG1 Fc complex.

Circulating Tumor DNA and RNA Assays: Tumors evolve during therapy, and drug-resistant cells emerge, which are difficult to detect and may cause the tumor to become resistant to the initial treatment. Blood-based testing for ctDNA and ctRNA can track the emergence of drug-resistant tumor cells and can identify new drug targets and treatment options for patients. Whole blood will be collected at screening/baseline and every month in the induction phase and every 2 months in the maintenance phase during routine blood draws for the analysis of ctDNA and ctRNA; a sample of 20.0 mL is required at the blood draw. Whole blood will be drawn into Cell-Free DNA BCT® tubes or Cell-Free RNA BCT® tubes containing DNA or RNA stabilizers, respectively. Expression levels of specific tumor- and immune-related analytes in ctDNA and ctRNA will be measured by qPCR and analyzed for correlations with subject outcomes.

Melanoma:

Skin cancer is the most common malignancy diagnosed in the US, with more than 2 million Americans diagnosed annually. Three main types of skin cancer exist: basal cell carcinoma, squamous cell carcinoma (SCC), collectively referred to as non-melanoma skin cancer, and melanoma. Melanoma is a malignant tumor of melanocytes and accounts for only about 1% of skin cancers, but the vast majority of skin cancer deaths. An estimated 87,110 new melanoma cases will be diagnosed in the US in 2017 with an estimated 9,730 deaths.

Melanoma incidence is rising rapidly in the US, and incidence rates have doubled from 1982 to 2011. More than 90% of melanoma cases have been attributed to excessive UV exposure, and increasing incidence rates are thought to reflect rising cumulative UV exposure. In addition to sun exposure, risk factors for developing melanoma include skin pigmentation, with lighter skin conferring higher risk. Melanoma is 20 times more common in whites than in African-Americans. A positive family history of melanoma, and the presence of some rare genetic mutations are also associated with higher risk for the disease.

Treatment for early-stage melanoma is largely effective, and for patients with localized disease, 5-year survival rates exceed 90%. Treatment options for early-stage melanoma focus on excision of the tumor while achieving positive tumor margins. However, for patients with metastatic or recurrent disease, prognoses are much poorer, and 5-year survival rates have historically been less than 10%, and median OS less than 1 year.

Treatment options for unresectable late-stage, and recurrent melanoma include intralesional therapy, immunotherapy, signal transduction inhibitors, chemotherapy, and palliative local therapy. New immunotherapies have offered novel treatment options for patients with advanced stage melanoma, and treatment with these agents has resulted in durable responses in a subset of patients. Immunotherapies currently approved for treatment of advanced melanoma include interleukin-2 (IL-2) and the checkpoint inhibitors ipilimumab, nivolumab, and pembrolizumab. A retrospective analysis of 8 studies of subjects with metastatic melanoma treated with high-dose IL-2 showed an overall ORR of 16%. Of the subjects who responded, 28% remained progression free at a median follow-up of 62 months. However, the high toxicities associated with IL-2, including capillary leak syndrome, limit its widespread use. In randomized trials, two approaches in particular, checkpoint inhibition and inhibition of the mitogen-activated protein kinase (MAPK) signal transduction pathway, have demonstrated improvement in OS when compared to dacarbazine monotherapy, which has long been the SoC for advanced melanoma. In clinical trials, treatment with dacarbazine has resulted in ORRs of 10-20%, but has not been associated with improvements in OS.

Signal transduction inhibitors that target the MAPK pathway, specifically, V-raf murine sarcoma viral oncogene homolog B1 (BRAF) and mitogen-activated ERK-(extracellular signal-regulated kinase) activating kinase (MEK) have also been investigated as treatment in patients with unresectable or advanced disease. BRAF gene mutations are the most frequent mutations in cutaneous melanoma. Approximately 40% to 60% of malignant melanomas harbor a single nucleotide mutation in BRAF; the most commonly found is a valine to glutamic acid substitution at position 600 (BRAF V600E). Vemurafenib, a selective BRAF V600E kinase inhibitor, has demonstrated improvement in both PFS and OS in patients with advanced disease, although its indication is limited to patients that have the BRAF V600E mutation as detected by an FDA-approved test. Dabrafenib is another selective inhibitor of BRAF that has resulted in improvement in PFS when compared to dacarbazine. The MEK inhibitors, trametinib and cobimetinib, have also been approved for treatment of patients with unresectable or metastatic melanoma. Monotherapy treatment with trametinib showed an improvement in PFS compared to the chemotherapy group (either dacarbazine or paclitaxel). Similarly, cobimetinib in combination with vemurafenib showed a significant increase in PFS over vemurafenib treatment alone.

Although treatment options for unresectable late-stage and recurrent melanoma have increased, neither checkpoint inhibition nor MAPK pathway inhibition appear to be curative when used as monotherapy.

In general, the overall goals of the melanoma Vaccine treatment are to maximize ICD and augment and maintain the innate and adaptive immune responses against cancer cells. The rationale for the selection of agents included in contemplated treatments is summarized in Table 3 in which a) denotes either avelumab or nivolumab will be administered; b) denotes Capecitabine is metabolized to 5-FU; and c) denotes that Leucovorin potentiates the activity of 5-FU.

Figure 14:
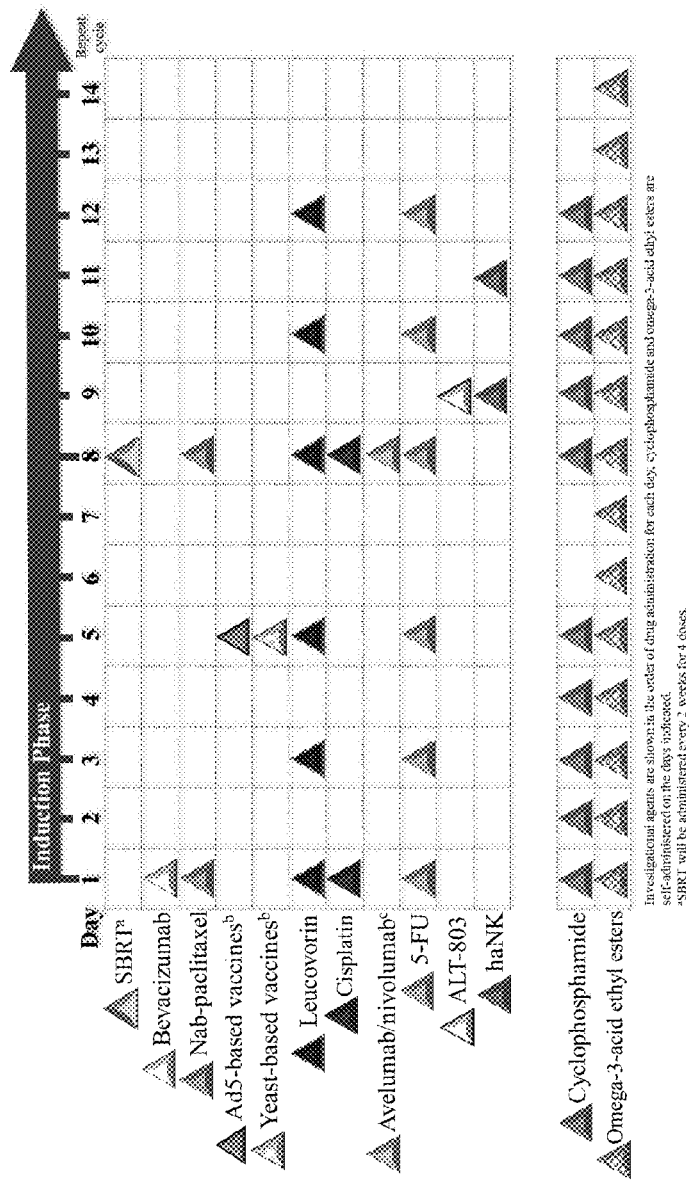
FIG. 14 is a flow chart for administration of various pharmaceutical compositions during the induction phase in the treatment of melanoma.
Figure 15:
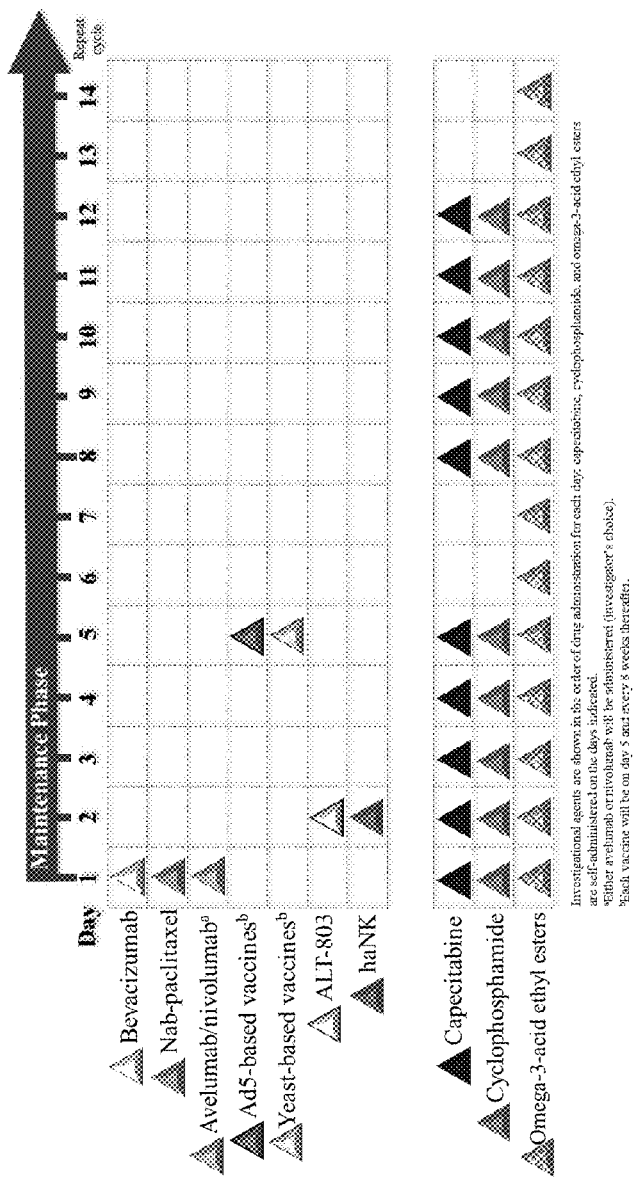
FIG. 15 is a flow chart for administration of various pharmaceutical compositions during the maintenance phase in the treatment of melanoma.

The melanoma vaccine treatment will be conducted in 2 phases: an induction phase and a maintenance phase. The purpose of the induction phase is to stimulate immune responses against tumor cells and mitigate immunosuppression in the TME. The purpose of the maintenance phase is to sustain ongoing immune system activity against tumor cells, creating durable treatment responses. Exemplary use and timing of administration of contemplated compounds and compositions for the induction phase and the maintenance phase are shown in FIG. 14 and FIG. 15, respectively.

| Agent | Mitigating Immunosuppression in the TME | Inducing and Coordinating ICD Signals | Conditioning Dendritic and T Cells | Enhancing Innate Immune Responses | Maintaining Immune Responses |
|---|---|---|---|---|---|
| ALT-803 | | | X | X | |
| Avelumab/nivolumab[i] | | | | | X |
| Bevacizumab | X | X | | | |
| Capecitabine[ii] | X | X | | | |
| Cisplatin | | X | | | |
| Cyclophosphamide | X | X | | | |
| ETBX-011 | | | X | | |
| ETBX-051 | | | X | | |
| ETBX-061 | | | X | | |
| 5-FU/leucovorin[iii] | X | X | | | |
| GI-6207 | | | X | | |
| GI-6301 | | | X | | |
| haNK cells | | | | X | |
| Nab-paclitaxel | X | X | | | |
| Omega-3-acid ethyl esters | | X | | | |
| SBRT | | X | | X | |

Figure 13:
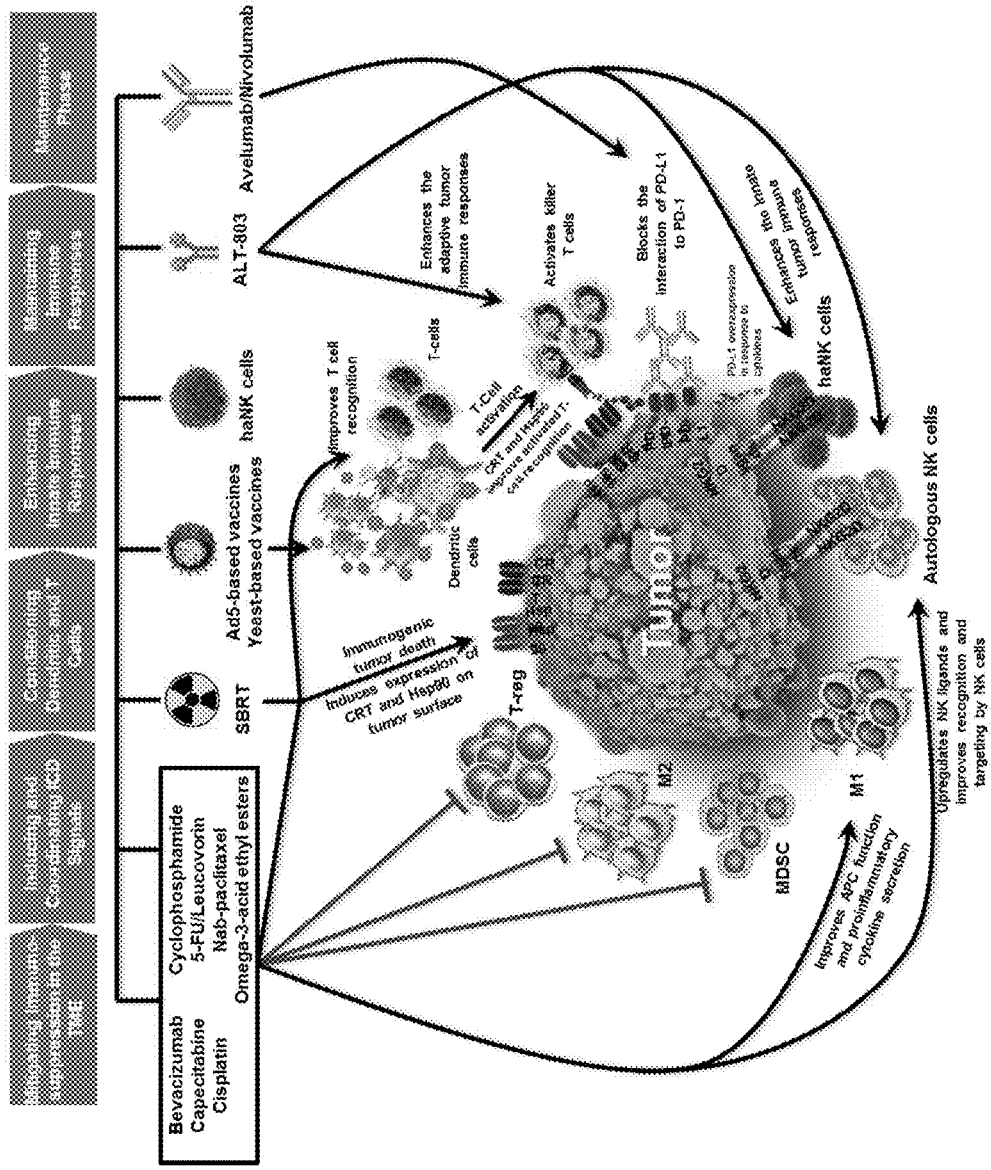
FIG. 13 is a schematic illustration of mechanism(s) by which each agent is thought to impact the immune system, consequently leading to immunogenic cell death of the tumor in the treatment of melanoma.

FIG. 13 schematically and exemplarily depicts the mechanism(s) by which each agent impacts the immune system, consequently leading to ICD. By combining agents that simultaneously target distinct but complementary mechanisms that enable tumor growth, the treatment regimen aims to maximize anticancer activity and prolong the duration of response to treatment.

To that end, contemplated melanoma treatments combine LDMC, bevacizumab, a cancer vaccine, low-dose radiation therapy, an IL-15 superagonist, NK cell therapy, and a checkpoint inhibitor. The overall goals of the treatment regimen are to maximize ICD and augment and maintain the innate and adaptive immune responses against cancer cells. More specifically, the treatment is designed to interrupt the escape phase of immunoediting by: (a) Mitigating immunosuppression in the TME. LDMC will be used to reduce the density of Tregs, MDSCs, and M2 macrophages contributing to immunosuppression in the TME. Bevacizumab will be used to cause morphological changes in the TME to promote lymphocyte trafficking; (b) Inducing and coordinating ICD signals. LDMC and low-dose radiation therapy will be used to increase the antigenicity of tumor cells. Bevacizumab will be used to alter the TME, which allows for more efficient antigen-specific T-cell responses and makes tumor cells more susceptible to ICD. Omega-3-acid ethyl esters enhances ICD without increasing toxicity; (c) Conditioning dendritic and T cells. A cancer vaccine and an IL-15 superagonist will be used to enhance tumor-specific cytotoxic T-cell responses; (d) Enhancing innate immune responses. NK cell therapy will be used to augment the innate immune system. An IL-15 superagonist will be used to enhance the activity of endogenous and introduced NK cells. Hypofractionated-dose radiation therapy will be used to upregulate tumor cell NK ligands to enhance tumor cytotoxicity of NK cells; and (e) Maintaining immune responses. A checkpoint inhibitor will be used to promote long-term anticancer immune responses.

Therefore, the following agents and compositions are preferably used for the induction and maintenance phases:

1. ALT-803, recombinant human super agonist interleukin-15 (IL-15) complex (also known as IL 15N72D1L-15RαSu/IgG1 Fc complex); 2. Avelumab (BAVENCIO® injection, for IV use); 3. Bevacizumab (AVASTIN® solution for IV infusion); 4. Capecitabine (XELODA® tablets, for oral use); 5. Cisplatin (Cis-platin injection); 6. Cyclophosphamide (CYCLOPHOSPHAMIDE Capsules, for oral use); 7. ETBX-011 (Ad5 [E1-, E2b-]-CEA); 8. ETBX-051 (Ad5 [E1-, E2b-]-Brachyury); 9. ETBX-061 (Ad5 [E1-, E2b-]-MUC1); 10. 5-FU (Fluorouracil Injection, for IV use only); 11. GI-6207 (CEA yeast vaccine); 12. GI-6301 (Brachyury yeast vaccine); 13. haNK™, NK-92 [CD16.158V, ER IL-2], Suspension for Intravenous Infusion (haNK™ for Infusion); 14. Leucovorin (LEUCOVORIN Calcium for Injection, for IV or IM use); 15. Nab-paclitaxel (ABRAXANE® for Injectable Suspension [paclitaxel protein-bound particles for injectable suspension] [albumin-bound]); 16. Nivolumab (OPDIVO® injection, for IV use); 17. Omega-3-acid ethyl esters (Lovaza capsules, for oral use); 18. SBRT.

More specifically, an exemplary treatment protocol for melanoma will typically include the following steps, phases, compounds, and compositions:

Tumor biopsies and exploratory tumor molecular profiling will be conducted at screening, at the end of the initial induction phase (8 weeks after the start of treatment), and during potential prolonged induction and maintenance phases (depending on response). Separate blood tubes will be collected every month in the induction phase and every 2 months in the maintenance phase during routine blood draws for exploratory immunology and ctDNA/ctRNA analyses.

Tumors will be assessed at screening, and tumor response will be assessed every 8 weeks during the induction phase and every 12 weeks during the maintenance phase by computed tomography (CT), magnetic resonance imaging (MM), or positron emission tomography-computed tomography (PET CT) of target and non-target lesions in accordance with Response Evaluation Criteria in Solid Tumors (RECIST) Version 1.1 and immune-related response criteria (irRC).

Induction Phase: The induction phase will comprise repeated 2 week cycles. The treatment regimen of ALT-803, Ad5-based vaccines (ETBX-011, ETBX-051, and ETBX-061), yeast-based vaccines (GI-6207 and GI-6301), haNK cells, avelumab or nivolumab, bevacizumab, cisplatin, cyclophosphamide, 5 FU/leucovorin, nab-paclitaxel, and omega-3-acid ethyl esters will be repeated every 2 weeks. Concurrent SBRT will be given during the first four 2-week cycles. Radiation will be administered to all feasible tumor sites using SBRT Specifically, an exemplary induction phase of melanoma treatment will be conducted in accordance with the following dosing regimen:

Daily:
Omega-3-acid ethyl esters (by mouth [PO] twice a day [BID] [3×1 g capsules and 2×1 g capsules])
Day 1, every 2 weeks:
Bevacizumab (5 mg/kg IV)
Days 1-5 and 8-12, every 2 weeks:
Cyclophosphamide (50 mg PO BID).
Days 1, 3, 5, 8, 10 and 12, every 2 weeks:
5-FU (400 mg/m2 as a continuous IV infusion over 24 hours)
Leucovorin (20 mg/m2 IV bolus)
Day 1 and 8, every 2 weeks:
Nab-paclitaxel (100 mg IV)
Cisplatin (40 mg/m2 IV)
Day 5, 19, 33 (every 2 weeks for 3 doses then every 8 weeks thereafter):
ETBX-011, ETBX-051, ETBX-061 ($5×10^{11}$ virus particles [VP]/vaccine/dose subcutaneously [SC])
GI-6207, GI-6301 (40 yeast units [YU]/vaccine/dose SC), 2 hours after administration of Ad5-based vaccines
Day 8, every 2 weeks:
Avelumab (10 mg/kg IV over 1 h) or nivolumab (3 mg/kg IV over 1 h).
Day 8, 22, 36, 50 (every 2 weeks for 4 doses):
SBRT (not to exceed 8 Gy, exact dose to be determined by the radiation oncologist)
Day 9, every 2 weeks:
ALT-803 (10 µg/kg SC 30 minutes prior to haNK infusion)
Day 9 and 11, every 2 weeks:
haNK ($2×10^9$ cells/dose IV)
Maintenance Phase: The duration of the maintenance phase will be up to one year following completion of the last treatment in the induction phase. The maintenance phase will comprise repeated 2-week cycles. The treatment regimen of ALT-803, Ad5 based vaccines (ETBX-011, ETBX 051, and ETBX 061), yeast-based vaccines (GI-6207 and GI-6301), haNK cells, avelumab or nivolumab, bevacizumab, capecitabine, cyclophosphamide, nab-paclitaxel, and omega-3-acid ethyl esters will be repeated every 2 weeks.

The maintenance phase of the treatment will be conducted in accordance with the following dosing regimen:
Daily:
Omega-3-acid ethyl esters (PO BID [3×1 g capsules and 2×1 g capsules])
Day 1, every 2 weeks:
Bevacizumab (5 mg/kg IV)
Nab-paclitaxel (100 mg IV)
Avelumab (10 mg/kg IV over 1 h) or nivolumab (3 mg/kg IV over 1 hour).
Days 1-5 and 8-12, every 2 weeks:
Cyclophosphamide (50 mg PO BID)
Capecitabine (650 mg/m2 PO BID)
Day 2, every 2 weeks:
ALT-803 (10 µg/kg SC 30 minutes prior to haNK infusion)
haNK ($2×10^9$ cells/dose IV)
Day 5, every 8 weeks thereafter:
ETBX-011, ETBX-051, ETBX-061 ($5×10^{11}$ VP/vaccine/dose SC)
GI-6301 (40 YU/dose SC), 2 hours after administration of Ad5-based vaccines.

Figure 16:
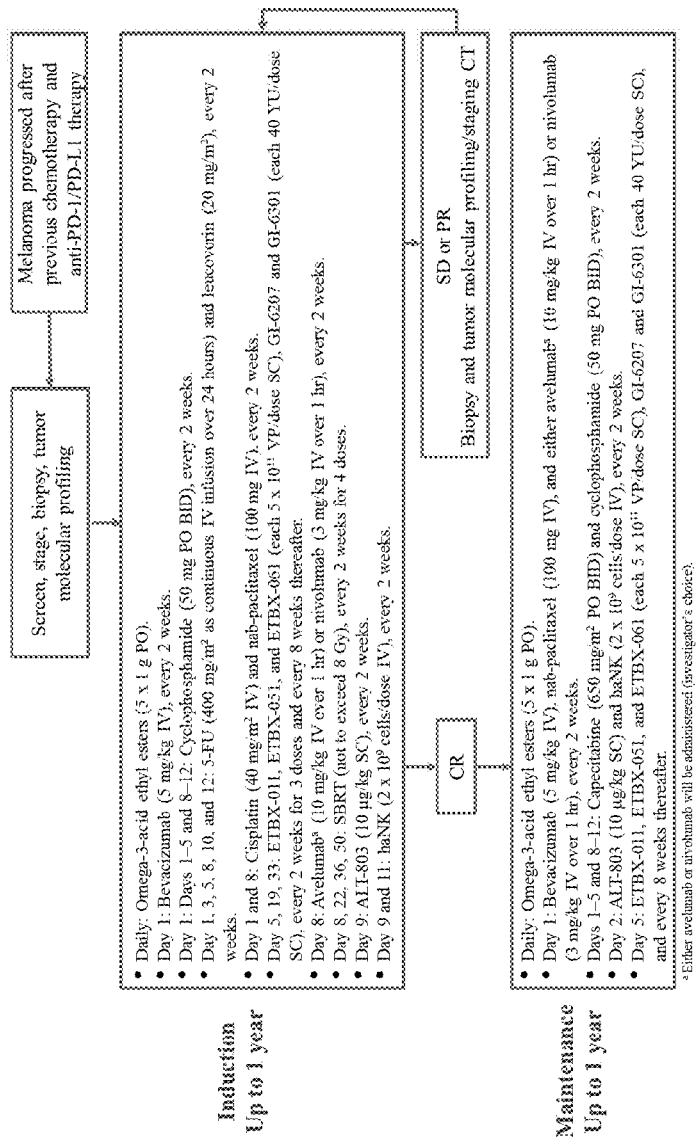
FIG. 16 is a schematic illustration of a treatment regimen for melanoma according to the inventive subject matter.

FIG. 16 schematically illustrates the exemplary treatment protocol.

Tumor Molecular Profiling: Genomic sequencing of tumor cells from tissue relative to non-tumor cells from whole blood will be conducted to identify tumor-specific genomic variances that may contribute to disease progression and/or response to treatment. RNA sequencing will be conducted to provide expression data and give relevance to DNA mutations. Quantitative proteomics analysis will be conducted to determine the absolute amounts of specific proteins, to confirm expression of genes that are correlative of disease progression and/or response, and to determine cutoff values for response.

Follow-up Analyses/Sample Collection and Analysis: Tumor molecular profiling will be performed on FFPE tumor tissue and whole blood (subject-matched normal comparator against the tumor tissue) by next-generation sequencing and mass spectrometry-based quantitative proteomics. Collection of tumor tissue and whole blood at screening and at the end of the initial induction phase (8 weeks after the start of treatment) is contemplated.

Tumor tissue and whole blood samples will be collected and shipped in accordance with the instruction cards included in the Tissue Specimen Kit and Blood Specimen Kit. An FFPE tumor tissue specimen is required for the extraction of tumor DNA, tumor RNA, and tumor protein. A whole blood sample is required for the extraction of subject normal DNA. Tumor tissue and whole blood will be processed in CLIA-certified and CAP-accredited clinical laboratories.

Exploratory Immunology Analysis: One aim of immunotherapy treatment is to generate antigen-specific antitumor immune responses. Exploratory immunology analysis will be used to provide a preliminary assessment of immune responses induced by the treatments. Blood samples for immune analysis will be collected from subjects at screening and every month in the induction phase and every 2 months in the maintenance phase during routine blood draws. A sample of 10.0 mL is required at the blood draw. PBMCs isolated by Ficoll-Hypaque density gradient separation will be analyzed for antigen-specific immune responses using ELISpot assays for IFN-γ or granzyme B secretion after exposure to CEA, Brachyury, and MUC1 peptides. Flow cytometry will be utilized to assess T cell responses using intracellular cytokine staining assay for IFN-γ or TNF-α expression after exposure to CEA, Brachyury, and MUC1 peptides. Flow cytometry analysis for the expression of CD107a on cells will be utilized to test for degranulating cells such as CD8+ T cells and NK cells (Kannan 1996). PBMCs will be stimulated in vitro with overlapping 15-mer peptide pools encoding CEA, Brachyury, and MUC1. Control peptide pools will involve the use of irrelevant antigen peptide pools as a negative control and CEFT peptide mix as a positive control. CEFT is a mixture of peptides of cytomegalovirus, EBV, influenza, and tetanus toxin. Post-stimulation analyses of CD4 and CD8 T cells will involve the production of IFN-γ, TNF-α, and CD107a expression. Sera will be analyzed for CEA-, Brachyury-, and MUC1 directed antibodies, neutralizing antibody titer to adenovirus (serotype 5), and for potential antibody development against the IL-15N72D1L-15RαSu/IgG1 Fc complex.

Circulating Tumor DNA and RNA Assays: Tumors evolve during therapy, and drug-resistant cells emerge, which are difficult to detect and may cause the tumor to become resistant to the initial treatment. Blood-based testing for ctDNA and ctRNA can track the emergence of drug-resistant tumor cells and can identify new drug targets and treatment options for patients. Whole blood will be collected at screening and every month in the induction phase and every 2 months in the maintenance phase during routine blood draws for the analysis of ctDNA and ctRNA. Expression levels of specific tumor- and immune-related analytes in ctDNA and ctRNA will be measured by qPCR and analyzed for correlations with subject outcomes.

Non-Hodgkin Lymphoma:

NHL is a highly prevalent disease in the US with a projected 72,240 new cases diagnosed in 2017, which accounts for approximately 4% of all cancers. This disease is the ninth-leading cause of cancer-related deaths with an estimate of 20,140 deaths in 2017. NHL can be classified as B-cell lymphomas or T-cell lymphomas. About 85% of NHL cases in the US are B-cell lymphomas. B-cell lymphomas comprise various subtypes, including diffuse large B-cell lymphoma (DLBCL), follicular lymphoma, small lymphocytic lymphoma, mantle cell lymphoma, marginal zone lymphomas, Burkitt lymphoma, and lymphoplasmacytic lymphoma. Of the B-cell lymphomas, DLBCL is the most common and is typically an aggressive disease. Follicular lymphoma, small lymphocytic lymphoma, marginal zone lymphoma, and lymphoplasmacytic lymphoma tend to be indolent diseases. Less than 15% of NHL cases in the US are T-cell lymphomas. Similar to B-cell lymphomas, there are many subtypes of T-cell lymphomas, which include precursor T-lymphoblastic lymphoma and peripheral T-cell lymphomas. Patients with NHL typically present with advanced stage (III/IV) disease, and many are initially asymptomatic.

Treatment of NHL varies based on the type and extent of disease and includes chemotherapy, immunotherapy, targeted therapy, radiation therapy, and stem cell transplant. Standard first-line therapy of CD20-positive NHL involves treatment with the anti-CD20 antibody rituximab either alone or in combination with chemotherapy, such as cyclophosphamide, doxorubicin, vincristine, and prednisone (R-CHOP); bendamustine (R-bendamustine), and cyclophosphamide, vincristine, and prednisone (R-CVP). Patients who relapsed after treatment with rituximab are categorized as rituximab refractory (RR) or rituximab sensitive (RS). Patients are considered RR if they progress while receiving rituximab or within 6 months of their last rituximab treatment. Patients are considered RS if they responded to prior rituximab containing regimens and relapse more than 6 months from their last dose of rituximab. For RS patients, approximately 40% of patients will respond to retreatment with rituximab. Clinical trial-based response and survival data for RR patients retreated with rituximab alone has not been reported, but reasonable estimates are a low response rate to single agent rituximab (<5%) retreatment.

Though most patients initially respond to treatment, many patients will eventually relapse and require further treatment. Furthermore, some patients do not respond to initial therapy. More effective treatments are still needed for CD20-positive NHL.

In general, the overall goals of the NHL vaccine treatment are to maximize ICD and augment and maintain the innate and adaptive immune responses against cancer cells. The rationale for the selection of agents is summarized in Table 4 in which (a) Capecitabine is metabolized to 5-FU; and (b) Leucovorin potentiates the activity of 5-FU.

| Agent | Mitigating Immunosuppression in the TME | Inducing and Coordinating ICD Signals | Conditioning Dendritic and T Cells | Enhancing Innate Immune Responses | Maintaining Immune Responses |
|---|---|---|---|---|---|
| ALT-803 | | | | X | X |
| Avelumab | | | | | X |
| Bevacizumab | X | X | | | |
| Capecitabine[i] | X | X | | | |
| Cyclophosphamide | X | X | | | |
| ETBX-061 | | | X | | |
| 5-FU/leucovorin[ii] | X | X | | | |
| haNK cells | | | | X | |
| Nab-paclitaxel | X | X | | | |
| Omega-3-acid ethyl esters | | X | | | |
| Oxaliplatin | | X | | | |
| Rituximab | | | | X | |
| SBRT | | X | | X | |

Figure 17:
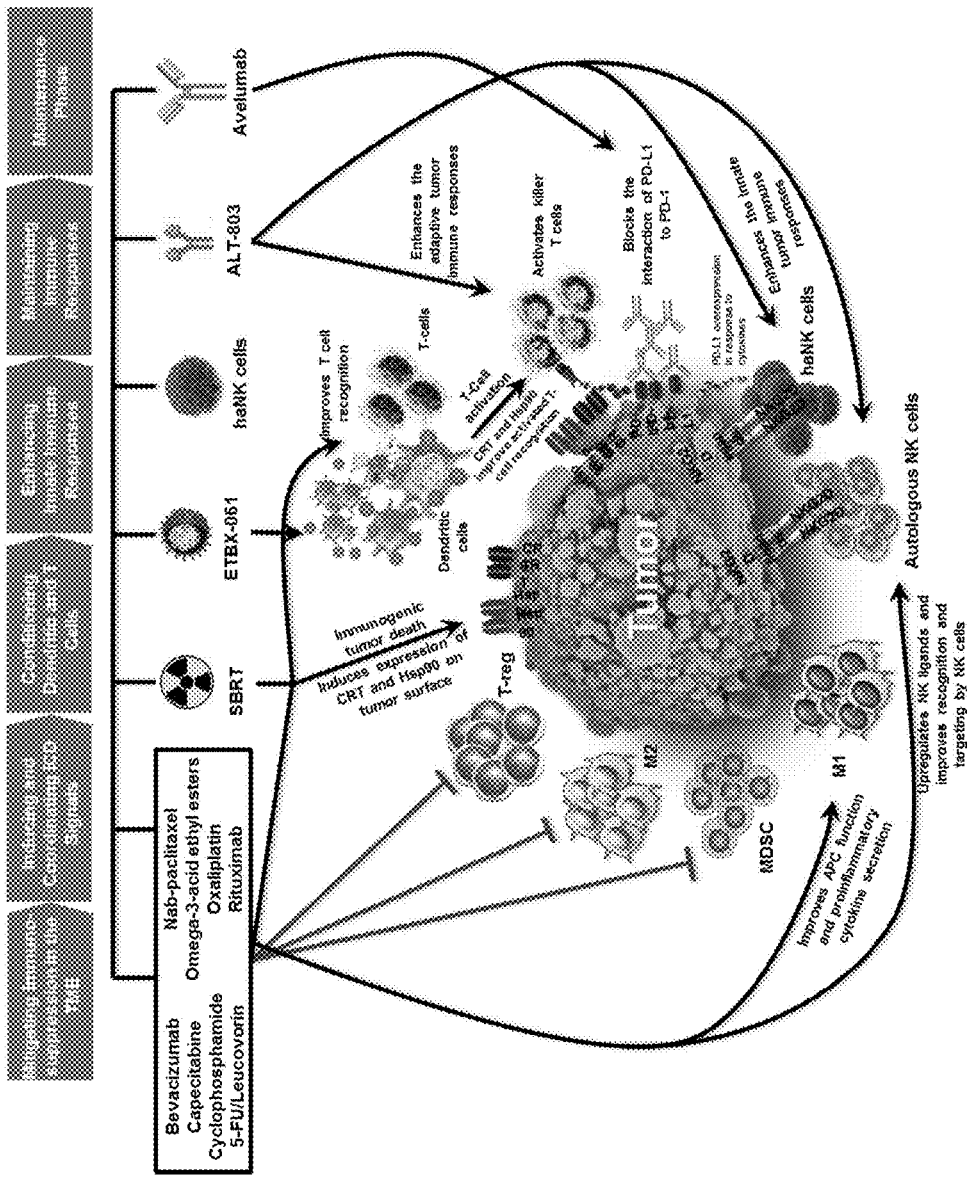
FIG. 17 is a schematic illustration of mechanism(s) by which each agent is thought to impact the immune system, consequently leading to immunogenic cell death of the tumor in the treatment of NHL.

FIG. 17 exemplarily and schematically depicts the mechanism(s) by which each agent impacts the immune system, consequently leading to ICD. By combining agents that simultaneously (or sequentially) target distinct but complementary mechanisms that enable tumor growth, the treatment regimen aims to maximize anticancer activity and prolong the duration of response to treatment.

To that end, contemplated NHL treatments combine LDMC, rituximab, bevacizumab, a cancer vaccine, low-dose radiation therapy, an IL-15 superagonist, NK cell therapy, and a checkpoint inhibitor. The overall goals of the treatment regimen are to maximize ICD and augment and maintain the innate and adaptive immune responses against cancer cells. Specifically, the treatment is designed to interrupt the escape phase of immunoediting by: (a) Mitigating immunosuppression in the TME. LDMC will be used to reduce the density of Tregs, MDSCs, and M2 macrophages contributing to immunosuppression in the TME. Bevacizumab will be used to cause morphological changes in the TME to promote lymphocyte trafficking; (b) Inducing and coordinating ICD signals. LDMC and low-dose radiation therapy will be used to increase the antigenicity of tumor cells. Bevacizumab will be used to alter the TME, which allows for more efficient antigen-specific T-cell responses and makes tumor cells more susceptible to ICD. Omega-3-acid ethyl esters enhance ICD without increasing toxicity; (c) Conditioning dendritic and T cells. A cancer vaccine and an IL-15 superagonist will be used to enhance tumor-specific cytotoxic T-cell responses; (d) Enhancing innate immune responses. NK cell therapy will be used to augment the innate immune system. An IL-15 superagonist will be used to enhance the activity of endogenous and introduced NK cells. Hypofractionated-dose radiation therapy will be used to upregulate tumor cell NK ligands to enhance tumor cytotoxicity of NK cells; and (e) Maintaining immune responses. A checkpoint inhibitor will be used to promote long-term anticancer immune responses.

Figure 18:
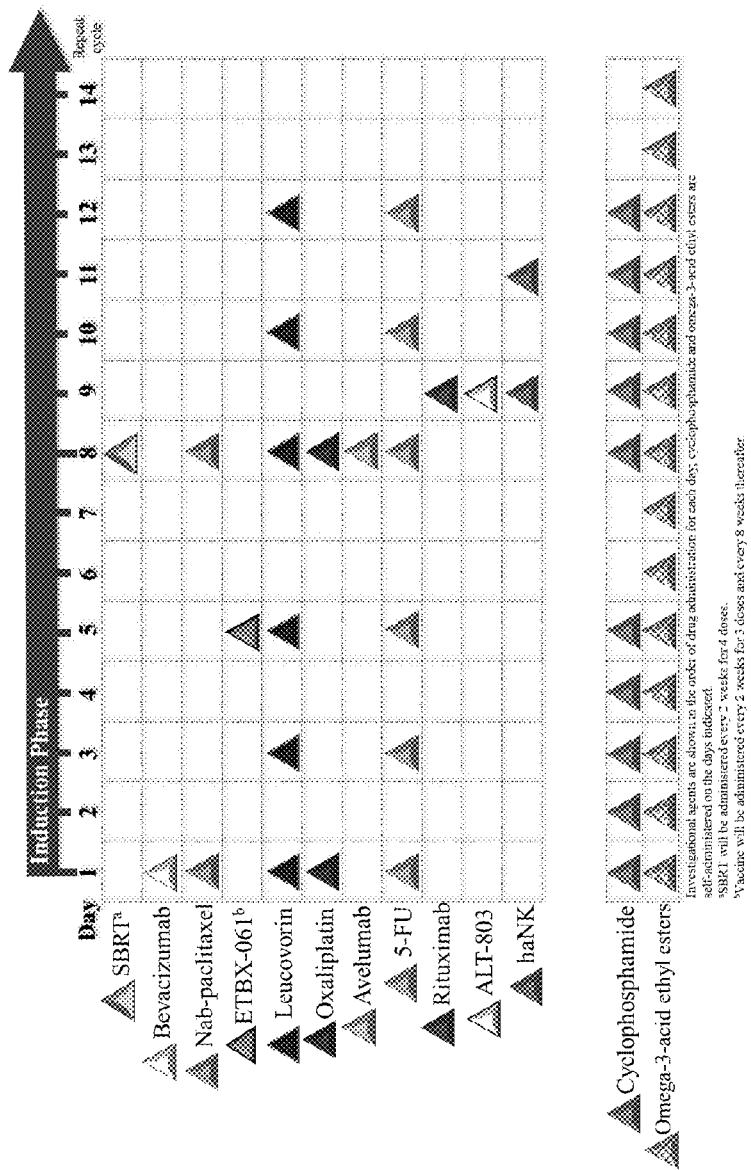
FIG. 18 is a flow chart for administration of various pharmaceutical compositions during the induction phase in the treatment of NHL.
Figure 19:
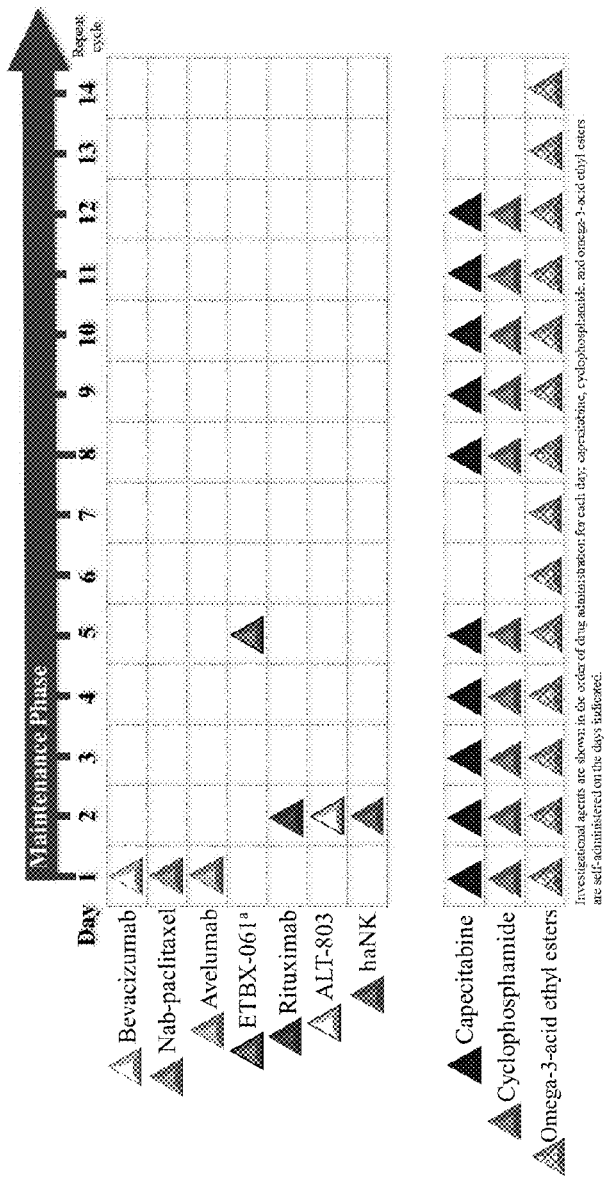
FIG. 19 is a flow chart for administration of various pharmaceutical compositions during the maintenance phase in the treatment of NHL.

The NHL vaccine treatment will be conducted in 2 phases: an induction phase and a maintenance phase. The purpose of the induction phase is to stimulate immune responses against tumor cells and mitigate immunosuppression in the TME. The purpose of the maintenance phase is to sustain ongoing immune system activity against tumor cells, creating durable treatment responses. Exemplary use and timing of administration of contemplated compounds and compositions for the induction phase and the maintenance phase are shown in FIG. 18 and FIG. 19, respectively. Therefore, the following agents and compositions are preferably used for the induction and maintenance phases:

1. ALT-803, recombinant human super agonist interleukin-15 (IL-15) complex (also known as IL 15N72D1L-15RαSu/IgG1 Fc complex); 2. Avelumab (BAVENCIO® injection, for IV use); 3. Bevacizumab (AVASTIN® solution for IV infusion); 4. Capecitabine (XELODA® tablets, for oral use); 5. Cyclophosphamide (CYCLOPHOSPHAMIDE Capsules, for oral use); 6. ETBX-061 (Ad5 [E1-, E2b-]-MUC1); 7. 5-FU (Fluorouracil Injection, for IV use only); 8. haNK™, NK-92 [CD16.158V, ER IL-2], Suspension for Intravenous Infusion (haNK™ for Infusion); 9. Leucovorin (LEUCOVORIN Calcium for Injection, for IV or IM use); 10. Nab-paclitaxel (ABRAXANE® for Injectable Suspension [paclitaxel protein-bound particles for injectable suspension] [albumin-bound]); 11. Omega-3-acid ethyl esters (Lovaza capsules, for oral use); 12. Oxaliplatin (ELOXATIN® injection for IV use); 13. Rituximab (RITUXAN® injection, for IV use); 14. SBRT.

More specifically, an exemplary treatment protocol for NHL will typically include the following steps, phases, compounds, and compositions:

Tumor biopsies and exploratory tumor molecular profiling will be conducted at screening, at the end of the initial induction phase (8 weeks after the start of treatment), and during potential prolonged induction and maintenance phases (depending on response). Separate blood tubes will be collected every month in the induction phase and every 2 months in the maintenance phase during routine blood draws for exploratory immunology and ctDNA/ctRNA analyses.

Tumors will be assessed at screening, and tumor response will be assessed every 8 weeks during the induction phase and every 12 weeks during the maintenance phase by computed tomography (CT), magnetic resonance imaging (MM), or positron emission tomography-computed tomography (PET CT) of target and non-target lesions in accordance with Response Evaluation Criteria in Solid Tumors (RECIST) Version 1.1 and immune-related response criteria (irRC).

Induction Phase: The induction phase will comprise repeated 2 week cycles. The treatment regimen of ALT-803, an Ad5-based vaccine (ETBX-061), haNK cells, avelumab, bevacizumab, cyclophosphamide, 5 FU/leucovorin, nab-paclitaxel, omega-3-acid ethyl esters, oxaliplatin, and rituximab will be repeated every 2 weeks. Concurrent SBRT will be given during the first four 2-week cycles. Radiation will be administered to all feasible tumor sites using SBRT.

The induction phase of the treatment will be conducted in accordance with the following dosing regimen:
Daily:
  Omega-3-acid ethyl esters (by mouth [PO] twice a day [BID] [3×1 g capsules and 2×1 g capsules])
Day 1, every 2 weeks:
  Bevacizumab (5 mg/kg IV)
Days 1-5 and 8-12, every 2 weeks:
  Cyclophosphamide (50 mg PO BID).
Days 1, 3, 5, 8, 10 and 12, every 2 weeks:
  5-FU (400 mg/m2 as a continuous IV infusion over 24 hours)
  Leucovorin (20 mg/m2 IV bolus)
Day 1 and 8, every 2 weeks:
  Nab-paclitaxel (100 mg IV)
  Oxaliplatin (40 mg/m2 IV)
Day 5, 19, 33 (every 2 weeks for 3 doses then every 8 weeks thereafter):
  ETBX-061 ($5×10^{11}$ virus particles [VP]/dose subcutaneously [SC])
Day 8, every 2 weeks:
  Avelumab (10 mg/kg IV over 1 h)
Day 8, 22, 36, 50 (every 2 weeks for 4 doses):
  SBRT (not to exceed 8 Gy, exact dose to be determined by the radiation oncologist)
Day 9, every 2 weeks:
  Rituximab (375 mg/m2 IV)
  ALT-803 (10 µg/kg SC 30 minutes prior to haNK infusion)
Day 9 and 11, every 2 weeks:
  haNK ($2×10^9$ cells/dose IV)
Maintenance Phase The duration of the maintenance phase will be up to 1 year following completion of the last treatment in the induction phase. The maintenance phase will comprise repeated 2-week cycles. The treatment regimen of ALT-803, an Ad5 based vaccine (ETBX 061), haNK cells, avelumab, bevacizumab, capecitabine, cyclophosphamide, nab-paclitaxel, omega-3-acid ethyl esters, and rituximab will be repeated every 2 weeks.

The maintenance phase of the treatment will be conducted in accordance with the following dosing regimen:
Daily:
  Omega-3-acid ethyl esters (PO BID [3×1 g capsules and 2×1 g capsules])
Day 1, every 2 weeks:
  Bevacizumab (5 mg/kg IV)
  Nab-paclitaxel (100 mg IV)
  Avelumab (10 mg/kg IV over 1 h)
Days 1-5 and 8-12, every 2 weeks:
  Cyclophosphamide (50 mg PO BID)
  Capecitabine (650 mg/m2 PO BID)
Day 2, every 2 weeks:
  Rituximab (375 mg/m2 IV)
  ALT-803 (10 µg/kg SC 30 minutes prior to haNK infusion)
  haNK ($2×10^9$ cells/dose IV)
Day 5, every 8 weeks thereafter:
  ETBX-061 ($5×10^{11}$ VP/dose SC)

Figure 20:
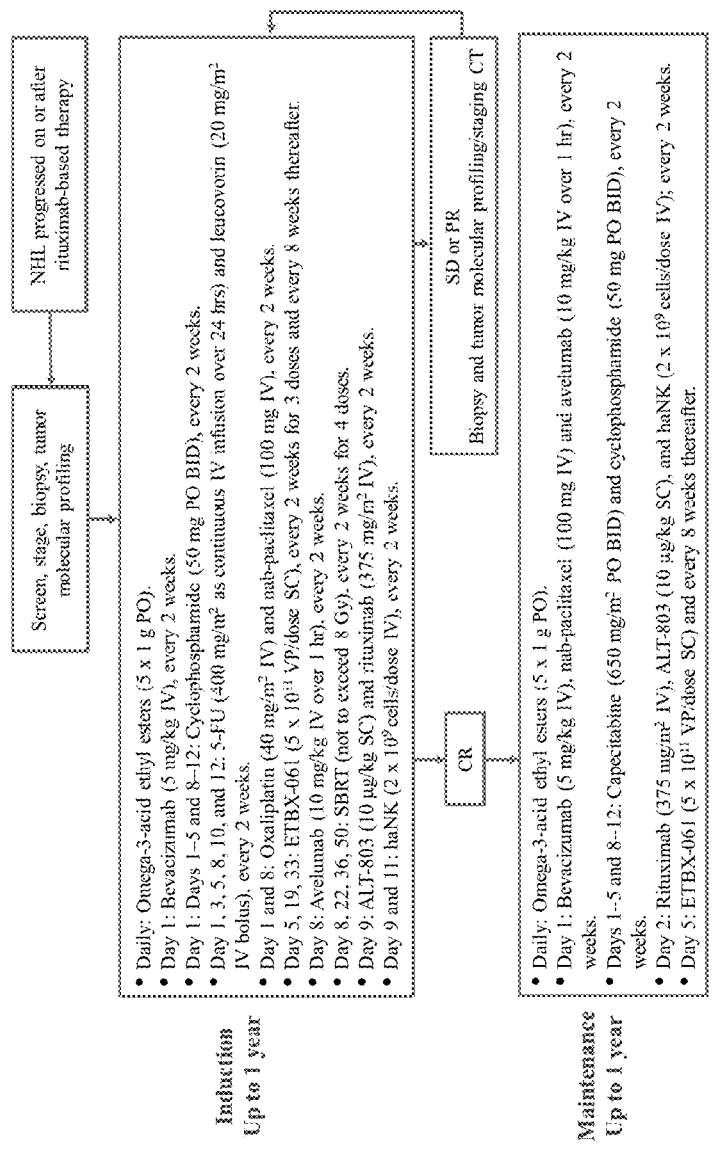
FIG. 20 is a schematic illustration of a treatment regimen for NHL according to the inventive subject matter.

FIG. 20 schematically illustrates the exemplary treatment method.

Tumor Molecular Profiling: Genomic sequencing of tumor cells from tissue relative to non-tumor cells from whole blood will be conducted to identify tumor-specific genomic variances that may contribute to disease progression and/or response to treatment. RNA sequencing will be conducted to provide expression data and give relevance to DNA mutations. Quantitative proteomics analysis will be conducted to determine the absolute amounts of specific proteins, to confirm expression of genes that are correlative of disease progression and/or response, and to determine cutoff values for response. All genomic, transcriptomic, and proteomic molecular analyses will be exploratory. Tumor molecular profiling will be performed on FFPE tumor tissue and whole blood (subject-matched normal comparator against the tumor tissue) by next-generation sequencing and mass spectrometry-based quantitative proteomics. Collection of tumor tissue and whole blood at screening and at the end of the initial induction phase (8 weeks after the start of treatment) is contemplated for this treatment.

Follow-up analyses/Sample collection and Analysis: Tumor tissue and whole blood samples will be collected and shipped in accordance with the instruction cards included in the Tissue Specimen Kit and Blood Specimen Kit. An FFPE tumor tissue specimen is typically required for the extraction of tumor DNA, tumor RNA, and tumor protein. A whole blood sample is typically required for the extraction of subject normal DNA. Tumor tissue and whole blood will be processed in CLIA-certified and CAP-accredited clinical laboratories.

Exploratory immunological analyses: One aim of immunotherapy treatment is to generate antigen-specific antitumor immune responses. Exploratory immunology analysis will be used to provide a preliminary assessment of immune responses induced by the the treatments. Blood samples for immune analysis will be collected from subjects at screening and every month in the induction phase and every 2 months in the maintenance phase during routine blood draws. PBMCs isolated by Ficoll-Hypaque density gradient separation will be analyzed for antigen-specific immune responses using ELISpot assays for IFN-γ or granzyme B secretion after exposure to MUC1. Flow cytometry will be utilized to assess T-cell responses using intracellular cytokine staining assay for IFN-γ or TNF-α expression after exposure to the tumor-associated antigen peptide, MUC1. Flow cytometry analysis for the expression of CD107a on cells will be utilized to test for degranulating cells such as CD8+ T cells and NK cells. PBMCs will be stimulated in vitro with overlapping 15-mer peptide pools encoding MUC1. Control peptide pools will involve the use of irrelevant antigen peptide pools as a negative control and CEFT peptide mix as a positive control. CEFT is a mixture of peptides of cytomegalovirus, EBV, influenza, and tetanus toxin. Post-stimulation analyses of CD4 and CD8 T cells will involve the production of IFN-γ, TNF-α, and CD107a expression. Sera will be analyzed for antibodies directed to MUC1, neutralizing antibody titer to adenovirus (serotype 5), and for potential antibody development against the IL-15N72D:IL-15RαSu/IgG1 Fc complex.

Circulating Tumor DNA and RNA Assays: Tumors evolve during therapy, and drug-resistant cells emerge, which are difficult to detect and may cause the tumor to become resistant to the initial treatment. Blood-based testing for ctDNA and ctRNA can track the emergence of drug-resistant tumor cells and can identify new drug targets and treatment options for patients. Whole blood will be collected at screening and every month in the induction phase and every 2 months in the maintenance phase during routine blood draws for the analysis of ctDNA and ctRNA. Expression levels of specific tumor- and immune-related analytes in ctDNA and ctRNA will be measured by qPCR and analyzed for correlations with subject outcomes.

Non-Small Cell Lung Cancer:

Lung cancer is the leading cause of cancer worldwide and is responsible for roughly 1 in 5 cancer deaths, totaling approximately 1.59 million annual deaths. The primary risk factor for all types of lung cancer is smoking, and roughly 85-90% of lung cancer cases can be attributed to this cause. Smoking cessation efforts have led to declining rates of lung cancer in the US over the last 25 years. Nonetheless, lung cancer continues to impose a tremendous health burden. In the US, an estimated 224,000 new cases of lung cancer where diagnosed in 2016, and roughly 158,000 deaths attributable to lung cancers occurred.

Lung cancers can be histologically classified into small cell lung cancer and NSCLC. NSCLC is an umbrella category, encompassing any lung cancer that is not small cell lung cancer, which is thought to arise from neuroendocrine cells in the lung. NSCLC comprises roughly 85% of lung cancers, and the most common types of NSCLC include squamous cell carcinoma, adenocarcinoma, and large cell carcinoma.

For patients with early stage, localized, and resectable disease, surgical approaches provide the best prognosis. Standard of care (SoC) surgical approaches have been reported to result in 5-year disease-free progression rates of roughly 70% in patients with stage 1 NSCLC. However, this applies to only a small minority of patients, as 70% of newly diagnosed lung cancer patients present with advanced stage disease, and most of these patients have metastatic disease. Surgery is not recommended for most patients with stage 3 or 4 NSCLC.

In general, the overall goals of the NSCLC vaccine treatment presented herein are to maximize ICD and augment and maintain the innate and adaptive immune responses against cancer cells. The rationale for the selection of agents included in this treatment is summarized in Table 5 in which (i) denotes tumor molecular profiling will determine whether ETBX-021 will be administered; (ii) denotes tumor molecular profiling will determine whether GI-4000 will be administered; (iii) denotes capecitabine is metabolized to 5-FU; (iv) denotes cisplatin will be administered to subjects with the squamous cell carcinoma subtype. Oxaliplatin will be administered to subjects with the adenocarcinoma subtype; (v) denotes Leucovorin potentiates the activity of 5-FU, and (vi) denotes that either nivolumab or avelumab will be administered.

| Agent | Mitigating Immunosuppression in the TME | Inducing and Coordinating ICD Signals | Conditioning Dendritic and T Cells | Enhancing Innate Immune Responses | Maintaining Immune Responses |
|---|---|---|---|---|---|
| Non-Marketed products | | | | | |
| ALT-803 | | | | X | X |
| ETBX-011 | | | | X | |
| ETBX-021[i] | | | | X | |

| Agent | Mitigating Immunosuppression in the TME | Inducing and Coordinating ICD Signals | Conditioning Dendritic and T Cells | Enhancing Innate Immune Responses | Maintaining Immune Responses |
|---|---|---|---|---|---|
| ETBX-051 | | | X | | |
| ETBX-061 | | | X | | |
| GI-4000[ii] | | | X | | |
| GI-6207 | | | X | | |
| GI-6301 | | | X | | |
| haNK cells | | | | X | |
| Approved products | | | | | |
| Bevacizumab | X | X | | | |
| Capecitabine[iii] | X | X | | | |
| Cisplatin/oxaliplatin[iv] | | X | | | |
| Cyclophosphamide | X | X | | | |
| 5-FU/leucovorin[v] | X | X | | | |
| Fulvestrant | | | X | | |
| Nab-paclitaxel | X | X | | | |
| Nivolumab/avelumab[vi] | | | | | X |
| Omega-3-acid ethyl esters | | X | | | |
| SBRT | | X | | X | |

Figure 21:
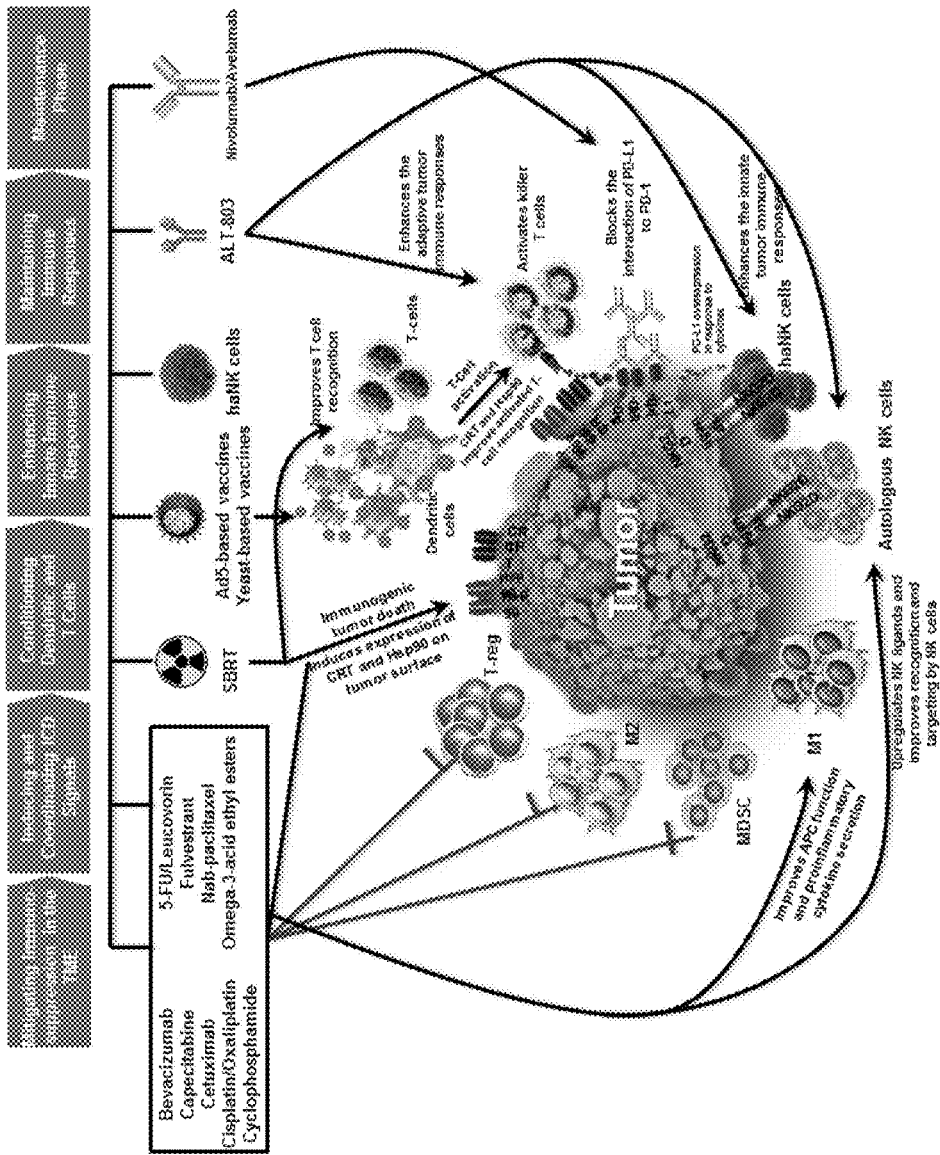
FIG. 21 is a schematic illustration of mechanism(s) by which each agent is thought to impact the immune system, consequently leading to immunogenic cell death of the tumor phase in the treatment of NSCLC.

FIG. 21 depicts the mechanism(s) by which each agent impacts the immune system, consequently leading to ICD. By combining agents that simultaneously target distinct but complementary mechanisms that enable tumor growth, the treatment regimen aims to maximize anticancer activity and prolong the duration of response to treatment.

To that end, contemplated NSCLC treatments combine LDMC, bevacizumab, cancer vaccines, low-dose radiation therapy, an IL-15 superagonist, NK cell therapy, and a checkpoint inhibitor. The overall goals of the treatment regimen are to maximize ICD and augment and maintain the innate and adaptive immune responses against cancer cells. Specifically, the treatment is set up to interrupt the escape phase of immunoediting by: (a) Mitigating immunosuppression in the TME. LDMC will be used to reduce the density of Tregs, MDSCs, and M2 macrophages contributing to immunosuppression in the TME. Bevacizumab will be used to cause morphological changes in the TME to promote lymphocyte trafficking; (b) Inducing and coordinating ICD signals. LDMC and low-dose radiation therapy will be used to increase the antigenicity of tumor cells. Bevacizumab will be used to alter the TME, which allows for more efficient antigen-specific T-cell responses and makes tumor cells more susceptible to ICD. Fulvestrant will be used to enhance ADCC and cytotoxic T-cell activity. Omega-3-acid ethyl esters enhances ICD without increasing toxicity; (c) Conditioning dendritic and T cells. A cancer vaccine and an IL-15 superagonist will be used to enhance tumor-specific cytotoxic T-cell responses; (d) Enhancing innate immune responses. NK cell therapy will be used to augment the innate immune system. An IL-15 superagonist will be used to enhance the activity of endogenous and introduced NK cells. Hypofractionated low-dose radiation therapy will be used to upregulate tumor cell NK ligands to enhance tumor cytotoxicity of NK cells; and (e) Maintaining immune responses. A checkpoint inhibitor will be used to promote long-term anticancer immune responses.

Figure 22:
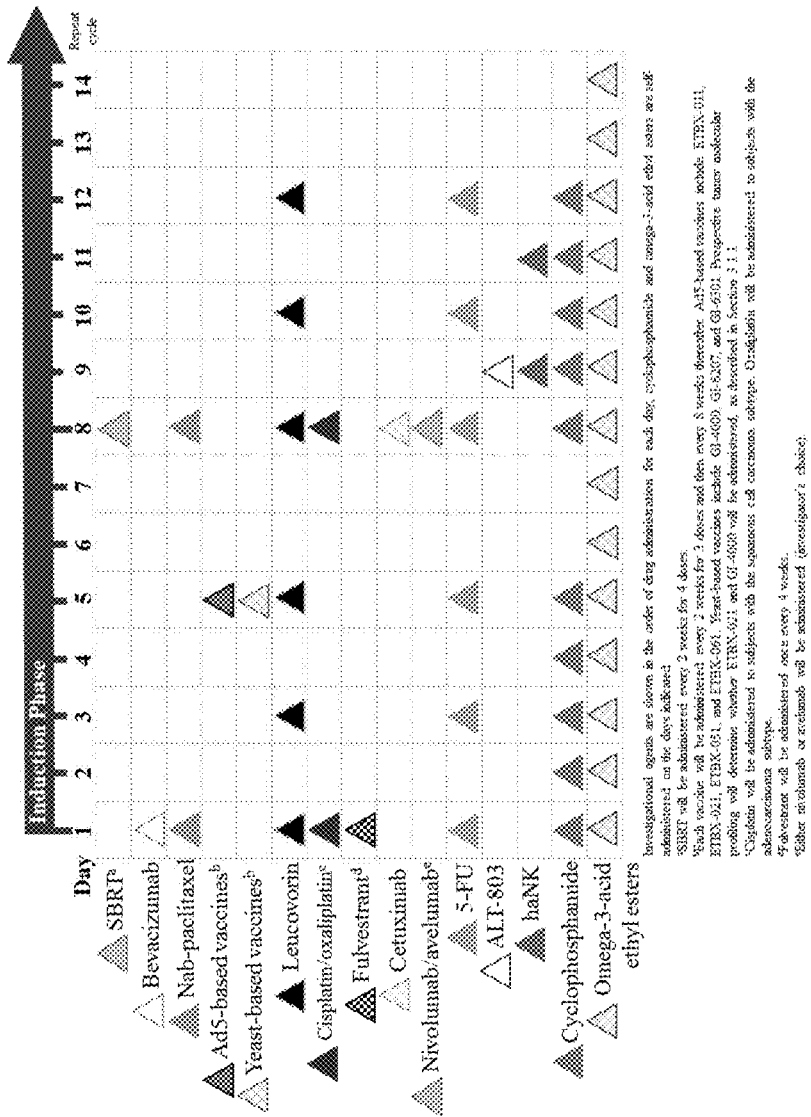
FIG. 22 is a flow chart for administration of various pharmaceutical compositions during the induction phase in the treatment of NSCLC.
Figure 23:
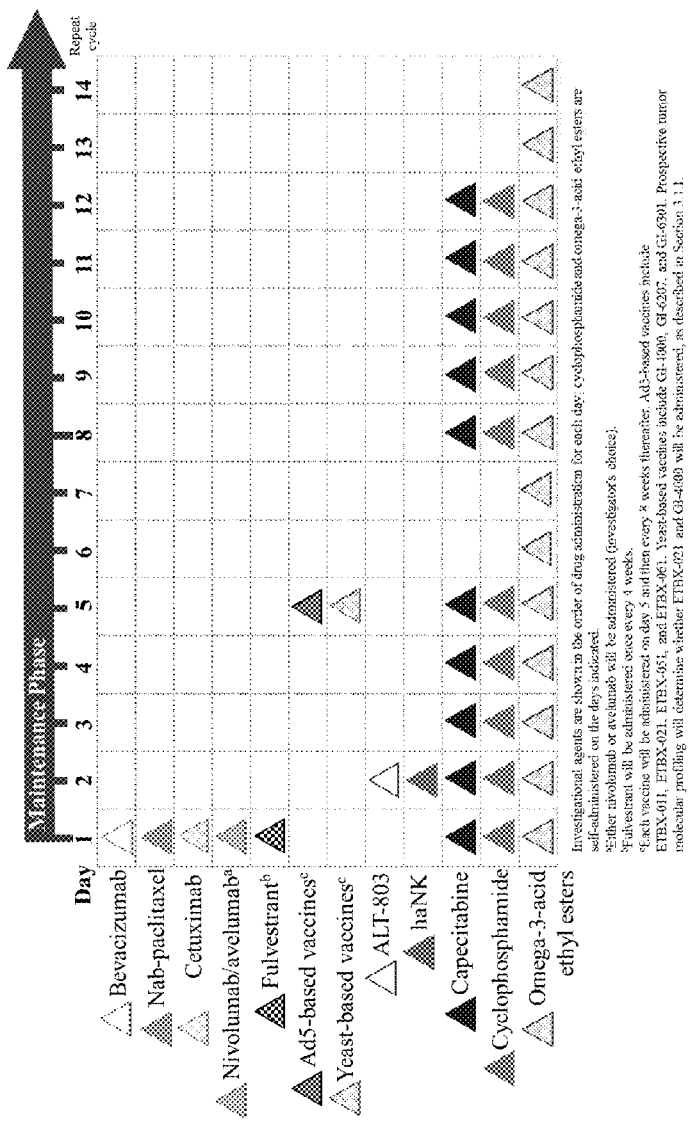
FIG. 23 is a flow chart for administration of various pharmaceutical compositions during the maintenance phase in the treatment of NSCLC.

The NSCLC vaccine treatment will be conducted in 2 phases: an induction phase and a maintenance phase. The purpose of the induction phase is to stimulate immune responses against tumor cells and mitigate immunosuppression in the TME. The purpose of the maintenance phase is to sustain ongoing immune system activity against tumor cells, creating durable treatment responses. Exemplary use and timing of administration of contemplated compounds and compositions for the induction phase and the maintenance phase are shown in FIG. 22 and FIG. 23, respectively. Therefore, the following agents and compositions are preferably used for the induction and maintenance phases:

1. ALT-803, recombinant human super agonist IL-15 complex (also known as IL 15N72D1L-15RαSu/IgG1 Fc complex); 2. ETBX-011 (Ad5 [E1-, E2b-]-CEA); 3. ETBX-021 (Ad5 [E1-, E2b-]-HER2); 4. ETBX-051 (Ad5 [E1-, E2b-]-Brachyury); 5. ETBX-061 (Ad5 [E1-, E2b-]-MUC1); 6. GI-4000 (Ras yeast vaccine); 7. GI-6207 (CEA yeast vaccine); 8. GI-6301 (Brachyury yeast vaccine); 9. haNK™, NK-92 [CD16.158V, ER IL-2], Suspension for IV Infusion (haNK™ for Infusion); 10. Avelumab (BAVENCIO® injection, for IV use); 11. Bevacizumab (AVASTIN® solution for IV infusion); 12. Capecitabine (XELODA® tablets, for oral use); 13. Cisplatin (CISplatin injection); 14. Cyclophosphamide (CYCLOPHOSPHAMIDE Capsules, for oral use); 15. 5-FU (Fluorouracil Injection, for IV use only); 16. Fulvestrant (FASLODEX® for injection); 17. Leucovorin (LEUCOVORIN Calcium for Injection, for IV or IM use); 18. Nab-paclitaxel (ABRAXANE® for Injectable Suspension [paclitaxel protein-bound particles for injectable suspension] [albumin-bound]); 19. Nivolumab (OPDIVO® injection, for IV use); 20. Omega-3-acid ethyl esters (Lovaza capsules, for oral use); 21. Oxaliplatin (ELOXATIN® injection for IV use); and 22. SBRT.

More specifically, an exemplary treatment protocol for NSCLC will typically include the following steps, phases, compounds, and compositions:

Tumors will be assessed at screening, and tumor response will be assessed every 8 weeks during the induction phase and every 12 weeks during the maintenance phase by computed tomography (CT), magnetic resonance imaging (MM), or positron emission tomography (PET)-CT of target and non-target lesions in accordance with Response Evaluation Criteria in Solid Tumors (RECIST) Version 1.1 and immune-related response criteria (irRC).

Prospective Tumor Molecular Profiling: Prospective tumor molecular profiling will be conducted to inform HER2 expression and Ras mutational status and will be used to determine whether ETBX-021 and GI-4000 will be administered. All subjects will receive ETBX-011, ETBX-051, ETBX-061, GI-6207, and GI-6300 regardless of their tumor molecular profile. Prospective tumor molecular profiling will be performed on FFPE tumor tissue and whole blood (subject-matched normal comparator against the tumor tissue) collected at screening.

Subjects will receive ETBX-021 if their tumor overexpresses HER2 (>750 attomole/μg of tumor tissue, as determined by quantitative proteomics with mass spectrometry). Subjects will receive GI-4000 if their tumor is positive for specific Ras mutations, as determined by whole genome sequencing. GI-4000 is 4 separate products from the GI-4000 series (GI-4014, GI-4015, GI-4016, and GI-4020); each of these expresses a combination of mutated Ras oncoproteins. The specific Ras mutation will determine which GI-4000 product will be used for treatment (GI-4014 for G12V, GI-4015 for G12C, GI-4016 for G12D, GI-4020 for G12R or Q61H, and GI-4014, GI-4015, or GI-4016 for Q61L or Q61R).

Induction Phase: The induction phase will comprise repeated 2-week cycles for a maximum treatment period of 1 year. The treatment regimen of omega-3-acid ethyl esters, cyclophosphamide, cisplatin or oxaliplatin, 5 FU/leucovorin, nab-paclitaxel, bevacizumab, ALT-803, haNK cells, Ad5-based vaccines (ETBX-011, ETBX-021, ETBX-051, and ETBX-061), yeast-based vaccines (GI-4000, GI-6207, and GI-6301), nivolumab or avelumab, fulvestrant, and radiation therapy will be repeated every 2 weeks. Concurrent SBRT will be given during the first four 2-week cycles. Radiation will be administered to all feasible tumor sites using SBRT. An exemplary induction phase of NSCLC treatment will be conducted in accordance with the following dosing regimen:

Daily:
Omega-3-acid ethyl esters (by mouth [PO] BID [3×1 g capsules and 2×1 g capsules])
Day 1, every 2 weeks:
Bevacizumab (5 mg/kg IV)
Day 1, every 4 weeks (every other treatment cycle):
Fulvestrant (500 mg IM)
Days 1-5 and 8-12, every 2 weeks:
Cyclophosphamide (50 mg PO twice a day [BID]).
Days 1, 3, 5, 8, 10 and 12, every 2 weeks:
5-FU (400 mg/m2 continuous IV infusion over 24 hours)
Leucovorin (20 mg/m2 IV bolus)
Day 1 and 8, every 2 weeks:
Nab-paclitaxel (100 mg IV)
Cisplatin (40 mg/m2 IV) or oxaliplatin (40 mg/m2 IV)
Cisplatin will be administered to subjects with the squamous cell carcinoma subtype. Oxaliplatin will be administered to subjects with the adenocarcinoma subtype.
Day 5, 19, 33 (every 2 weeks for 3 doses then every 8 weeks thereafter):
ETBX-011, ETBX-021, ETBX-051, ETBX-061 ($5\times10^{11}$ virus particles [VP]/vaccine/dose subcutaneously [SC])
GI-4000, GI-6207, GI-6301, (40 yeast units [YU]/vaccine/dose SC), 2 hours after administration of the Ad5-based vaccines
Prospective tumor molecular profiling will determine whether ETBX-021 and GI-4000 will be administered, as described above.
Day 8, every 2 weeks:
Nivolumab (3 mg/kg IV over 1 hour) or avelumab (10 mg/kg IV over 1 hour)
Day 8, 22, 36, 50 (every 2 weeks for 4 doses):
SBRT (not to exceed 8 Gy, exact dose to be determined by the radiation oncologist)
Day 9, every 2 weeks:
ALT-803 (10 μg/kg SC 30 minutes prior to haNK infusion)
Day 9 and 11, every 2 weeks:
haNK ($2\times10^9$ cells/dose IV)

Maintenance Phase: The duration of the maintenance phase will be up to 1 year following completion of the last treatment in the induction phase. The maintenance phase will comprise repeated 2-week cycles. The treatment regimen of omega-3-acid ethyl esters, cyclophosphamide, capecitabine, nab-paclitaxel, bevacizumab, ALT-803, haNK cells, Ad5-based vaccines (ETBX-011, ETBX-021, ETBX-051, and ETBX-061), yeast-based vaccines (GI-4000, GI-6207, and GI-6301), nivolumab or avelumab, and fulvestrant will be repeated every 2 weeks. An exemplary maintenance phase of the treatment will be conducted in accordance with the following dosing regimen:

Daily:
Omega-3-acid ethyl esters (PO BID [3×1 g capsules and 2×1 g capsules])
Day 1, every 2 weeks:
Bevacizumab (5 mg/kg IV)
Nab-paclitaxel (100 mg IV)
Nivolumab (3 mg/kg IV over 1 hour) or avelumab (10 mg/kg IV over 1 hour)
Day 1, every 4 weeks (every other treatment cycle):
Fulvestrant (500 mg IM)
Days 1-5 and 8-12, every 2 weeks:
Capecitabine (650 mg/m2 PO BID)
Cyclophosphamide (50 mg PO BID)
Day 2, every 2 weeks:
ALT-803 (10 μg/kg SC) (30 minutes prior to haNK infusion)
haNK ($2\times10^9$ cells/dose IV)
Day 5, every 8 weeks thereafter:
ETBX-011, ETBX-021, ETBX-051, ETBX-061 ($5\times10^{11}$ VP/vaccine/dose SC)
GI-4000, GI-6207, GI-6301 (40 YU/vaccine/dose SC), 2 hours after administration of the Ad5 based vaccines.

Figure 24:
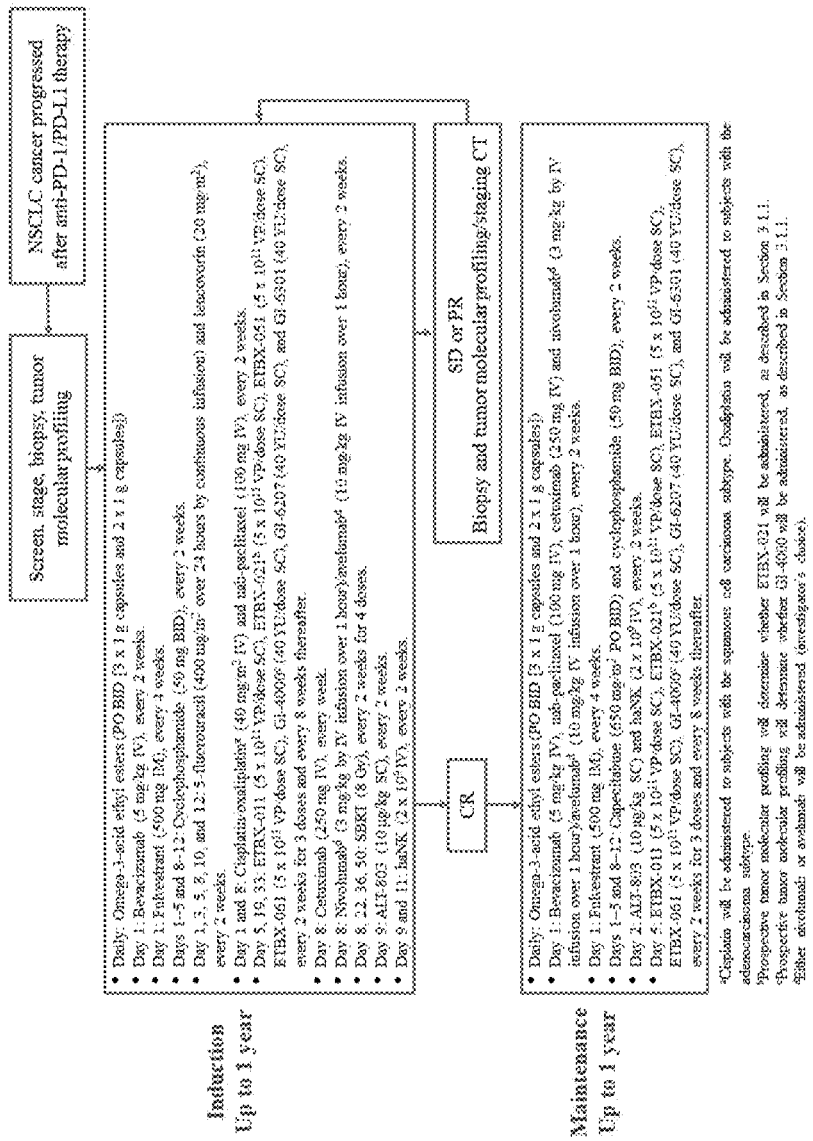
FIG. 24 is a schematic illustration of a treatment regimen for NSCLC according to the inventive subject matter.

Prospective molecular profiling will determine whether ETBX-021 and GI-6207 will be administered, as described above. FIG. 24 schematically illustrates the exemplary treatment protocol.

Tumor Molecular Profiling: Genomic sequencing of tumor cells from tissue relative to non-tumor cells from whole blood will be conducted to identify tumor-specific genomic variances that may contribute to disease progression and/or response to treatment. RNA sequencing will be conducted to provide expression data and give relevance to DNA mutations. Quantitative proteomics analysis will be conducted to determine the absolute amounts of specific proteins, to confirm expression of genes that are correlative of disease progression and/or response, and to determine cutoff values for response. All genomic, transcriptomic, and proteomic molecular analyses will be exploratory, except for the prospective tumor molecular analysis of HER2 expression by quantitative proteomics and analysis of Ras mutational status by genomic sequencing to determine whether ETBX-021 and GI-4000 will be administered.

Follow-up analyses/Sample Collection and Analysis: Tumor molecular profiling will be performed on FFPE tumor tissue and whole blood (subject-matched normal comparator against the tumor tissue) by next-generation sequencing and mass spectrometry-based quantitative proteomics. Collection of tumor tissue and whole blood at screening and at the end of the initial induction phase (8 weeks after the start of treatment) is contemplated for this treatment. An FFPE tumor tissue specimen is typically required for the extraction of tumor DNA, tumor RNA, and tumor protein. A whole blood sample is typically required for the extraction of subject normal DNA. Tumor tissue and whole blood will be processed in CLIA-certified and CAP-accredited clinical laboratories.

Blood samples for immune analysis will be collected from subjects at screening and every month in the induction phase and every 2 months in the maintenance phase during routine blood draws. PBMCs isolated by Ficoll-Hypaque density gradient separation will be analyzed for antigen-specific immune responses using ELISpot assays for IFN-γ or granzyme B secretion after exposure to the following tumor-associated antigen peptides: CEA, Brachyury, and MUC1, and if ETBX-021 and GI-4000 are administered, HER2 and mutant Ras, respectively. Flow cytometry will be utilized to assess T-cell responses using intracellular cytokine staining assay for IFN-γ or TNF-α expression after exposure to the tumor-associated antigen peptides. Flow cytometry analysis for the expression of CD107a on cells will be utilized to test for degranulating cells such as CD8+ T cells and NK cells. PBMCs will be stimulated in vitro with overlapping 15-mer peptide pools encoding the tumor-associated antigens mentioned above. Control peptide pools will involve the use of irrelevant antigen peptide pools as a negative control and CEFT peptide mix as a positive control. CEFT is a mixture of peptides of CMV, Epstein-Barr virus, influenza, and tetanus toxin. Post-stimulation analyses of CD4+ and CD8+ T cells will involve the production of IFN-γ, TNF-α, and CD107a expression. Sera will be analyzed for antibodies directed to the aforementioned tumor-associated antigens, neutralizing antibody titer to adenovirus (serotype 5), and for potential antibody development against the IL-15N72DIL-15RαSu/IgG1 Fc complex.

Circulating Tumor DNA and RNA Assays: Tumors evolve during therapy, and drug-resistant cells emerge, which are difficult to detect and may cause the tumor to become resistant to the initial treatment. Blood-based testing for ctDNA and ctRNA can track the emergence of drug-resistant tumor cells and can identify new drug targets and treatment options for patients. Whole blood will be collected at screening and every month in the induction phase and every 2 months in the maintenance phase during routine blood draws for the analysis of ctDNA and ctRNA. Expression levels of specific tumor- and immune-related analytes in ctDNA and ctRNA will be measured by qPCR and analyzed for correlations with subject outcomes.

Pancreatic Cancer:

Pancreatic cancer is projected to be the second leading cause of cancer-related death in the US, with an estimated 43,090 deaths from the disease and an estimated 53,670 new cases expected in 2017. It is the 12$^{th}$ most common cancer worldwide, with around 338,000 new cases diagnosed in 2012 (2% of the total). The prognosis is poor, and as a result, pancreatic cancer is the 7$^{th}$ most common cause of cancer death worldwide, with more than 330,000 deaths from pancreatic cancer in 2012 (4% of the total).

The pancreas is composed of 2 main cell types, exocrine and endocrine. Exocrine cells produce digestive enzymes, while the endocrine cells of the islets of Langerhans produce the hormones insulin and glucagon. Endocrine tumors typically have a better prognosis but only account for 6% of the pancreatic cancer that develops. Exocrine tumors, on the other hand, are rarely curable and are by far the most common type of pancreatic cancer, with adenocarcinoma accounting for about 94% of cancers of the exocrine pancreas. Incidence rates for pancreatic cancer have increased by approximately 1% per year from 2004 to 2013 in white individuals, but have remained the same for black individuals.

The prognosis for patients with pancreatic adenocarcinoma is very poor, with an overall median survival of 5 to 8 months; fewer than 5% of patients live for more than 5 years. Surgical resection of the pancreatic cancer and subsequent adjuvant chemotherapy is the main treatment option required to achieve long-term survival. It can be achieved in about 15% to 20% of newly diagnosed patients; however, recurrence is common, even in cases where optimal resection is achieved. For the majority of the patients who present with more advanced disease, treatment typically comprises chemotherapy alone or supportive care for metastatic patients, and chemotherapy with or without radiation for those with locally advanced disease. The prognosis for these patients is even less promising, with a 5-year survival of 2%.

A majority of patients with pancreatic cancer present with advanced disease. Survival rates for this group are remarkably low, with just 2% of patients with metastatic disease surviving 5 years from the time of diagnosis. A small group of patients (9%) are diagnosed with localized resectable disease; however, even for this group, 5-year survival rates are poor, at just over 25%. Standard of care treatment for patients with pancreatic cancer is treatment with FOLFIRINOX, which improves OS and PFS over monotherapy with gemcitabine; however, FOLFIRINOX is available only to patients in relatively good health (ECOG 0 or 1), and prognosis for patients receiving treatment remains grim, with median PFS of 6.4 months and median OS of 11.1 months (Conroy 2011). Novel treatment options that can produce long-lasting, durable responses in a substantial fraction of patients are clearly needed for patients with pancreatic cancer.

In general, the overall goals of the PANC vaccine treatment presented herein are to maximize immunological cell death (ICD) while maintaining and augmenting patients' antitumor adaptive and innate response to cancers. The rationale for the selection of agents included in the treatment is summarized in Table 6.

| Agent | Overcoming Suppressive TME | Induction and Coordination of Immunogenic Signals | Dendritic and T cell Conditioning | Enhancing NK Cell Responses | Maintenance of the Immune Response |
|---|---|---|---|---|---|
| Cyclophosphamide | X | | | | |
| Oxaliplatin | | X | | | |
| 5-FU/capecitabine | X | | | | |
| Nab-paclitaxel | X | X | | | |
| Bevacizumab | X | X | | | |
| Avelumab | | | | | X |

-continued

| Agent | Overcoming Suppressive TME | Induction and Coordination of Immunogenic Signals | Dendritic and T cell Conditioning | Enhancing NK Cell Responses | Maintenance of the Immune Response |
|---|---|---|---|---|---|
| Radiation therapy | | X | | | |
| ALT-803 | | | X | X | |
| aNK for Infusion | | | | X | |
| Ad5 vaccine | | | X | | |
| GI-4000 RAS vaccine | | | X | | |

Figure 25:
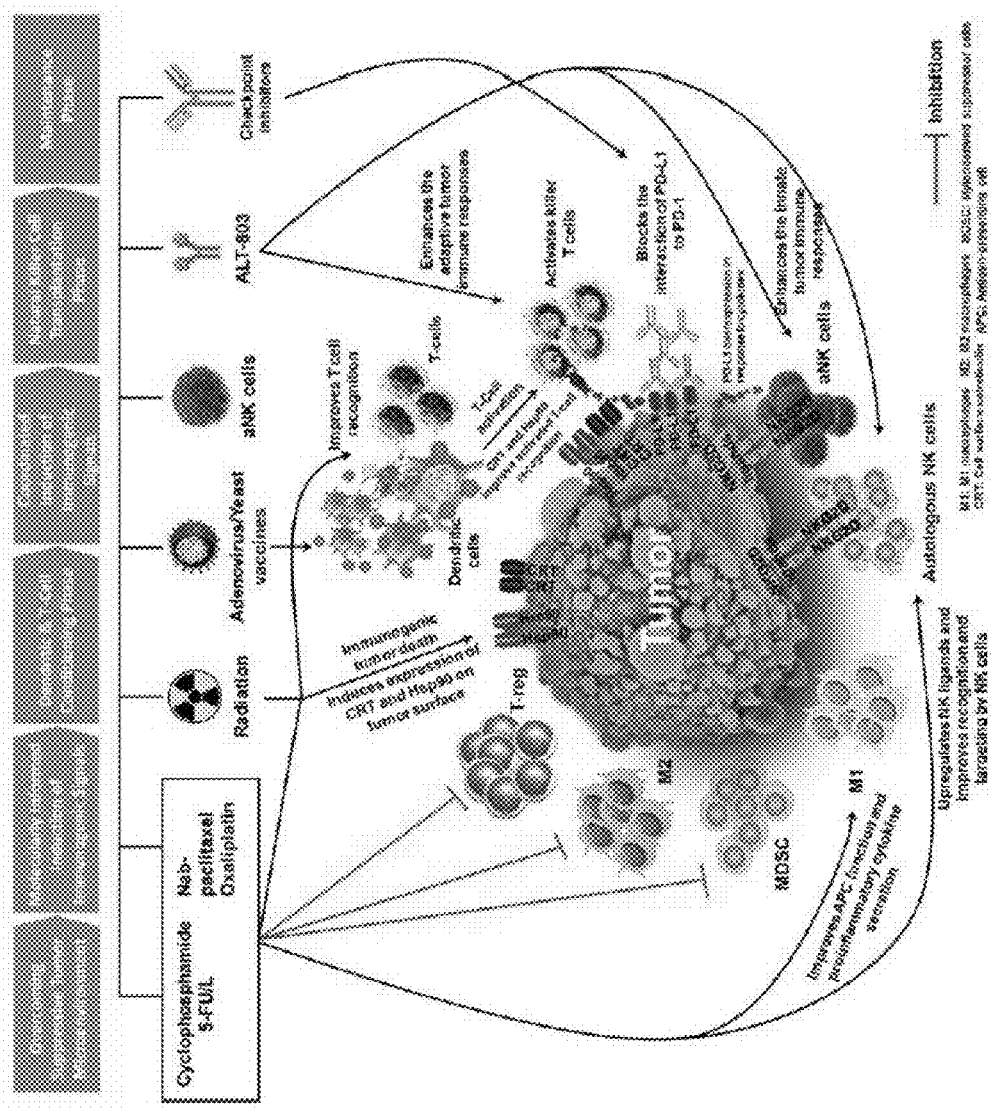
FIG. 25 is a schematic illustration of mechanism(s) by which each agent is thought to impact the immune system, consequently leading to immunogenic cell death of the tumor in the treatment of PANC.

FIG. 25 depicts the mechanism(s) by which each agent impacts the immune system, consequently leading to ICD. By combining agents that simultaneously target distinct but complementary mechanisms that enable tumor growth, the treatment regimen aims to maximize anticancer activity and prolong the duration of response to treatment.

To that end, contemplated PANC treatments are set up to achieve the specific and complementary aims of: 1) overcoming the suppressive TME; 2) molecularly-informed induction of immunogenic signals; 3) dendritic and T cell conditioning; 4) NK cell transplant; and 5) maintenance of the immune response and induction of durable long-term remission through administration of LDMC.

Figure 26:
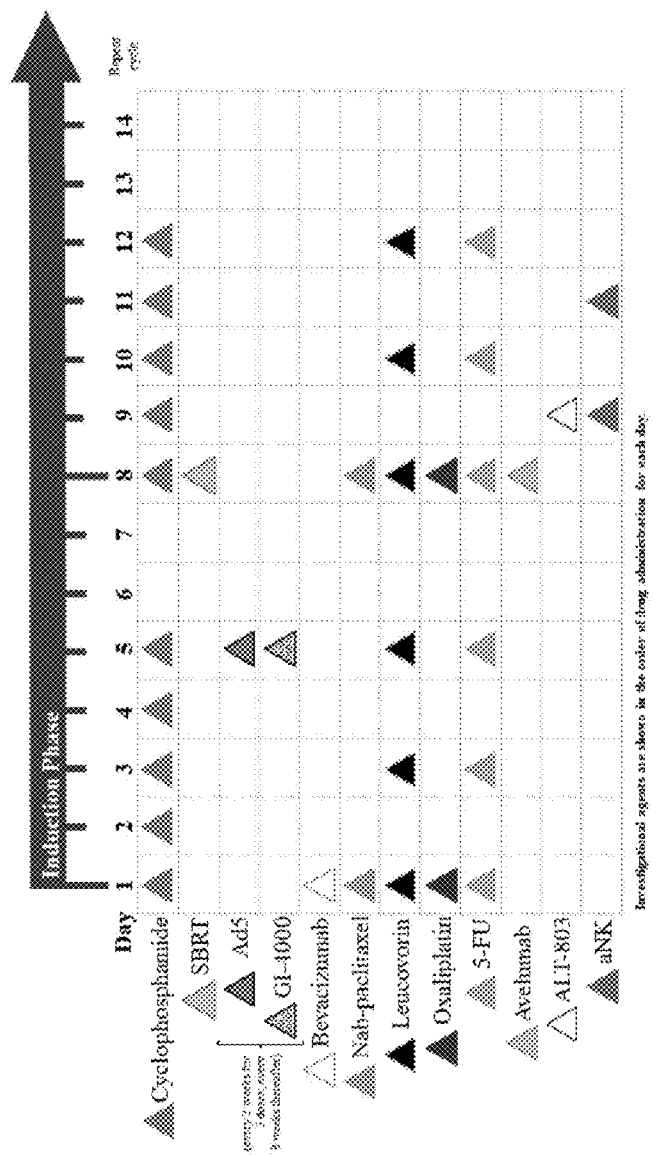
FIG. 26 is a flow chart for administration of various pharmaceutical compositions during the induction phase in the treatment of PANC.
Figure 27:
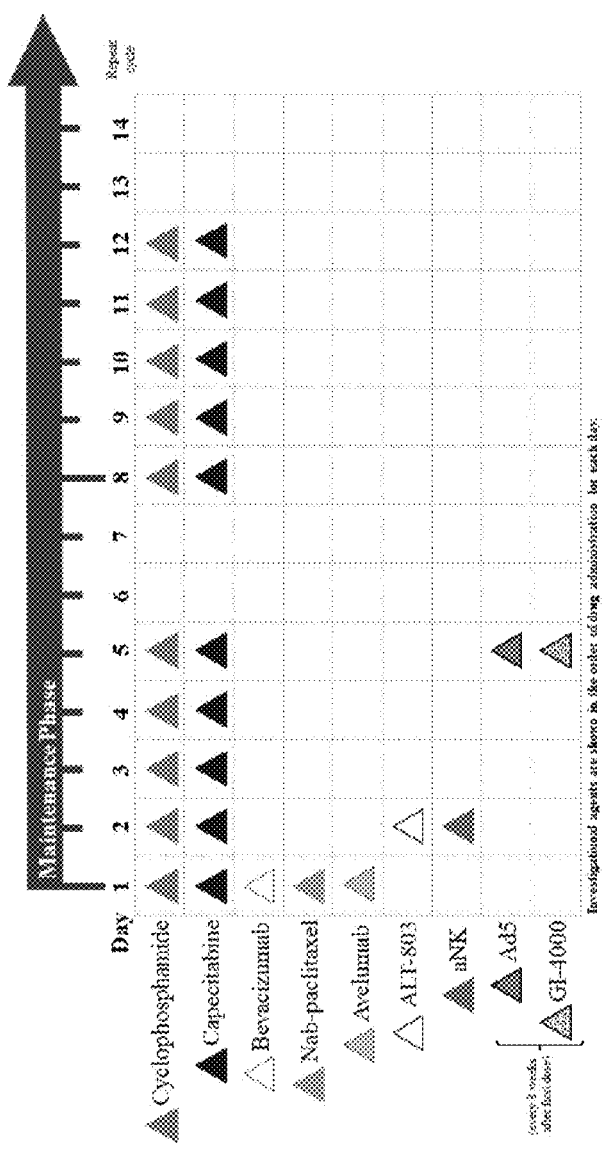
FIG. 27 is a flow chart for administration of various pharmaceutical compositions during the maintenance phase in the treatment of PANC.

The PANC vaccine treatment will be conducted in 2 phases: an induction phase and a maintenance phase. The purpose of the induction phase is to stimulate immune responses against tumor cells and mitigate immunosuppression in the TME. The purpose of the maintenance phase is to sustain ongoing immune system activity against tumor cells, creating durable treatment responses. Exemplary use and timing of administration of contemplated compounds and compositions for the induction phase and the maintenance phase are shown in FIG. 26 and FIG. 27, respectively. Therefore, the following agents and compositions are preferably used for the induction and maintenance phases:

1. CYCLOPHOSPHAMIDE tablets, for oral use; 2. ELOXATIN® (oxaliplatin for injection, USP); 3. XELODA (capecitabine) tablets, for oral use; 4. Fluorouracil Injection, for intravenous use; 5. LEUCOVORIN Calcium for Injection, for IV or IM use; 6. ABRAXANE® (nab-paclitaxel); 7. AVASTIN (bevacizumab); 8. ALT-803, recombinant human super agonist interleukin-15 (IL-15) complex (also known as IL 15N72D1L-15RαSu/IgG1 Fc complex); 9. aNK™, NK-92 [CD16.158V, ER IL-2] (high-affinity activated natural killer cell line, [aNK™ for Infusion]); 10. ETBX-011: Ad5 [E1-, E2b-]-CEA (carcinoembryonic antigen); 11. Avelumab, a human anti-PD-L1 IgG1 monoclonal antibody; 12. GI-4000, a vaccine derived from recombinant Saccharomyces cerevisiae yeast expressing mutant Ras proteins.

More specifically, an exemplary treatment protocol for PANC will typically include the following steps, phases, compounds, and compositions:

Tumor biopsies and tumor molecular profiling will be conducted at screening and at the end of the initial induction (8 weeks) and during a potential prolonged induction phase (depending on response). In addition, during routine weekly blood draws, a separate blood tube will be collected to analyze blood for changes in circulating RNA. Tumors will be assessed at screening, and tumor response will be assessed every 8 weeks during the induction phase, and every 3 months during the maintenance phase by computed tomography (CT), magnetic resonance imaging (MM), or positron emission tomography (PET) of target and non-target lesions according to Response Evaluation Criteria in Solid Tumors (RECIST) Version 1.1 and immune-related response criteria (irRC).

Induction Phase: The induction phase will comprise repeated 2 week cycles of low-dose radiation and metronomic chemotherapy. The treatment regimen of cyclophosphamide, oxaliplatin, 5-FU/leucovorin, nab-paclitaxel, bevacizumab, ALT-803, aNK, vaccines (Ad5 and GI-4000), and avelumab will be repeated every 2 weeks. Concurrent stereotactic body radiotherapy (SBRT) will be given during the first four 2-week cycles. Radiation will be administered to all feasible tumor sites using SBRT. Techniques contemplated include linear-accelerator based therapies (3D and intensity-modulated radiation therapy [IMRT]) and gamma and cyber knife.

The induction treatment will continue until the subject experiences PD or unacceptable toxicity (not correctable with dose reduction). Subjects that have a CR in the induction phase will enter the maintenance phase of the treatment. Response assessments using CT/MRI evaluated according to RECIST Version 1.1 and irRC will be performed every 8 weeks during the induction phase.

Days 1-5 and 8-12, every 2 weeks:
Cyclophosphamide (50 mg twice a day [BID]).
Day 1 and 8, every 2 weeks:
Oxaliplatin (40 mg/m2 IV)
Nab-paclitaxel (125 mg IV)
Day 1 every 2 weeks:
Bevacizumab (5 mg/kg IV)
Days 1, 3, 5, 8, 10 and 12, every 2 weeks:
5-fluorouracil (400 mg/m2 over 24 hours as a continuous infusion)
Leucovorin (20 mg/m2 IV bolus)
Day 8, 22, 36, 50 (every 2 weeks for 4 doses):
SBRT (8 Gy)
Day 9, every 2 weeks:
ALT-803 (10 µg/kg subcutaneously [SC] 30 minutes prior to aNK infusion)
Day 9 and 11, every 2 weeks:
aNK ($2 \times 10^9$ cells/dose IV)
Day 5, 19, 33 (every 2 weeks for 3 doses then every 8 weeks thereafter):
Ad5 [E1-, E2b-]-CEA ($5 \times 10^{11}$ VP/dose SC)
GI-4000 (40 yeast units [YU] SC; use dependent on genomic sequencing indicating required KRAS mutations)
Day 8, every 2 weeks:
Avelumab (10 mg/kg IV over 1 h)

Maintenance Phase: The duration of the maintenance phase will be 1 year following completion of the last treatment in the induction phase. Treatment will continue throughout the maintenance phase unless the subject experiences PD or unacceptable toxicity. Response assessments using CT/MRI evaluated according to RECIST Version 1.1 and irRC will be performed every 3 months during the maintenance phase.

Days 1-5 and 8-12, every 2 weeks:
Cyclophosphamide (50 mg BID)
Capecitabine (650 mg/m2 PO BID)
Day 1, every 2 weeks:
Nab-paclitaxel (125 mg IV)
Bevacizumab (5 mg/kg IV)
Avelumab (10 mg/kg IV over 1 h)
Day 2, every 2 weeks:
ALT-803 (10 µg/kg SC) (30 minutes prior to aNK infusion)
aNK ($2\times10^9$ cells/dose IV)
Day 5, every 8 weeks thereafter:
Ad5 [E1-, E2b-]-CEA ($5\times10^{11}$ VP/dose SC)
GI-4000 (40 YU SC)

Figure 28:
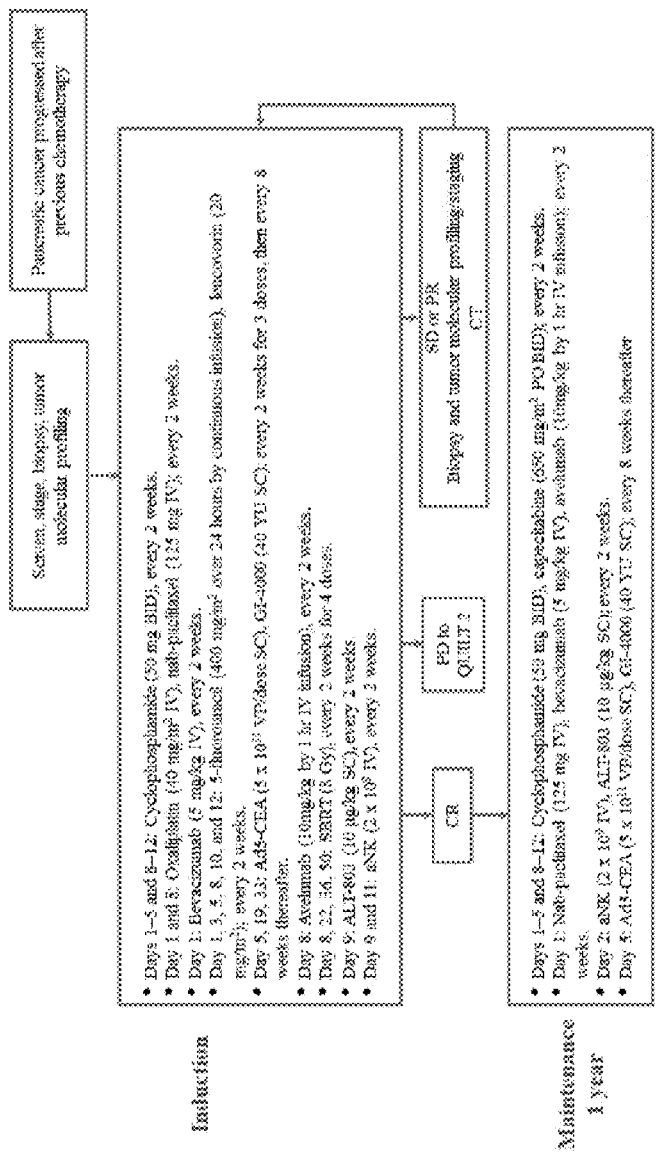
FIG. 28 is a schematic illustration of a treatment regimen for PANC according to the inventive subject matter.

FIG. 28 schematically illustrates the exemplary treatment protocol.

Follow-up analyses/sample collection and analysis: Exploratory genomics, transcriptomics, circulating RNA and proteomics molecular profiling will be performed on FFPE tumor tissue and whole blood (subject matched normal comparator against the tumor tissue) by next-generation sequencing and mass spectrometry-based quantitative proteomics. During the induction phase, blood samples will be collected on a weekly basis for molecular profiling. During the maintenance phase, blood samples will be collected on a monthly basis for molecular profiling; a sample of 22.5 mL is required at each blood draw.

Sample Collection and Analysis for cell free DNA and cell free RNA: The specimens are 10 mL of whole blood drawn into Cell-free RNA BCT® tubes or Cell-free DNA BCT® tubes containing RNA or DNA stabilizers, respectively. CtRNA is stable in whole blood in the Cell-free RNA BCT tubes for 7 days; ctDNA is stable in whole blood in the Cell-free DNA BCT Tubes for 14 days. These nucleic acid stabilizers allow time for shipping of patient samples without degradation of ctRNA or ctDNA. Whole blood in 10 mL tubes is centrifuged to fractionate plasma at 1600 rcf for 20 minutes. The plasma is separated and centrifuged at 16,000 rcf for 10 minutes to remove cell debris. CtDNA and ctRNA were extracted from 2 mL of plasma with a proprietary in-house developed protocol using Qiagen reagents. The protocol was designed to remove potential contaminating blood cells, other impurities and maintain stability of the nucleic acids during the extraction. All nucleic acids are kept in bar-coded matrix storage tubes. DNA is stored at −4° C. and RNA is stored at −80° C. or reverse-transcribed to complementary DNA (cDNA) and cDNA is stored at −4° C.

Expression of PD-L1 is measured by quantitative real-time PCR of ct-cDNA using primers specific for this gene. Amplification is performed in a 10 µL reaction mix containing 2 µL cDNA, the primer and probe. (3-actin is used as an internal control for the input level of ct-cDNA. A standard curve of samples with known concentrations of PD-L1 is run on each PCR plate as well as positive and negative controls for each gene. Test samples are identified by scanning the 2D barcode on the matrix tubes containing the nucleic acids. Delta Ct (dCT) is calculated from the Ct value of PD-L1 subtracted by the Ct value of β-actin. Relative expression of patient specimens is calculated using a standard curve of delta Cts of serial dilutions of Universal Human Reference RNA set at a gene expression value of 10 (when the delta CTs are plotted against the log concentration of PD-L1). The PD-L1 levels will be analyzed with the primary and secondary outcomes to identify statistically and clinically significant correlations.

Immunology Analysis: Blood samples for immune analysis will be collected from subjects prior to their first treatment and again at Day 1 of each treatment cycle and at the end of the treatment. Pre- and post-therapy PBMCs, isolated by Ficoll-Hypaque density gradient separation, will be analyzed for antigen-specific immune responses using ELISpot assays for IFN-γ or granzyme B secretion after exposure to CEA peptides. Flow cytometry will be utilized to assess T cell responses using intracellular cytokine staining assay for IFN-γ or TNF-α expression after exposure to CEA peptides. Flow cytometry analysis for the expression of CD107a on cells will be utilized to test for degranulating cells such as CD8+ T cells and NK cells. PBMCs will be stimulated in vitro with overlapping 15-mer peptide pools encoding the tumor-associated antigen CEA. Control peptide pools will involve the use of irrelevant antigen peptide pools as a negative control and CEFT peptide mix as a positive control. CEFT is a mixture of peptides of CMV, Epstein-Barr virus, influenza, and tetanus toxin. Post-stimulation analyses of CD4 and CD8 T cells will involve the production of IFN-γ, TNF-α, and CD107a expression. Sera will be analyzed pre- and post-therapy for CEA directed antibody, neutralizing antibody titer to adenovirus (serotype 5), and for potential antibody development against the IL-15N72D1L-15RαSu/IgG1 Fc complex.

Soft Tissue Sarcoma:

Soft-tissue sarcomas are relatively uncommon cancers. They account for less than 1% of all new cancer cases each year. This may be because cells in soft tissue, in contrast to tissues that more commonly give rise to malignancies, are not continuously dividing cells.

In 2006, about 9,500 new cases were diagnosed in the United States. Soft-tissue sarcomas are more commonly found in older patients (>50 years old) although in children and adolescents under age 20, certain histologies are common (rhabdomyosarcoma, synovial sarcoma).

In general, the overall goals of the soft tissue sarcoma vaccine treatment are to maximize ICD and augment and maintain the innate and adaptive immune responses against cancer cells. Similar to the treatment compounds and compositions above, the following agents and compositions are preferably used for the induction and maintenance phases:

1. CYCLOPHOSPHAMIDE tablets, for oral use; 2. Trabectedin for intravenous use; 3. AVASTIN (bevacizumab) solution for IV infusion; 4. Avelumab, a human anti-PD-L1 IgG1 monoclonal antibody; 5. ABRAXANE® (nab-paclitaxel) for injectable suspension; 6. Doxorunicin; 7. ALT-803, recombinant human super agonist interleukin-15 (IL-15) complex (also known as IL 15N72D1L-15RαSu/IgG1 Fc complex); 8. HaNK™, NK-92 (activated natural killer cell line, aNK™ for infusion; 9. Ad5 [E1-, E2b-]-MUC1; 10. Ad5 [E1-, E2b-]-Brachyury; and 11. GI 6301—Yeast Brachyury.

More specifically, an exemplary treatment protocol for soft tissue sarcoma will typically include the following steps, phases, compounds, and compositions:

Tumor biopsies and tumor molecular profiling will be conducted at screening and at the end of the initial induction (8 weeks) and during a potential prolonged induction phase (depending on response). In addition, during routine weekly blood draws, a separate blood tube will be collected to analyze blood for changes in circulating RNA. Tumors will be assessed at screening, and tumor response will be assessed every 8 weeks during the induction phase, and every 3 months during the maintenance phase by computed tomography (CT), magnetic resonance imaging (MM), or positron emission tomography (PET) of target and non-target lesions according to Response Evaluation Criteria in Solid Tumors (RECIST) Version 1.1 and immune-related response criteria (irRC).

Induction Phase: The induction phase will comprise repeated 2 week cycles of low-dose radiation and metronomic chemotherapy. The treatment regimen of cyclophosphamide, doxorubicin, nab-paclitaxel, bevacizumab, trabectedin, ALT-803, HaNK, avelumab, vaccine, and radiation therapy will be repeated every 2 weeks. Concurrent stereotactic body radiotherapy (SBRT) will be given during the first four 2-week cycles. Radiation will be administered to all feasible tumor sites using SBRT. Techniques contemplated include linear-accelerator based therapies (3D and intensity-modulated radiation therapy [IMRT]).

The induction treatment will continue until the subject experiences PD or unacceptable toxicity (not correctable with dose reduction). Subjects that have a CR in the induction phase will enter the maintenance phase of the treatment. Response assessments using CT/MRI will be performed every 8 weeks during the induction phase and will be evaluated according to RECIST Version 1.1 and irRC.

Days 1-5 (weekly):
Cyclophosphamide 50 mg twice a day (BID)
Day 1 (weekly):
Doxorubicin 20 mg/m2 IV
Day 1 (every 2 weeks):
Bevacizumab 5 mg/kg IV
Days 1 (weekly):
Trabectedin 0.5 mg/kg IV
nab-paclitaxel 100 mg IV
Day 8, 22, 36, 50 (every other week for 4 doses):
SBRT 8 Gy
Day 9 (every 2 weeks):
ALT-803 10 µg/kg SC
Day 9 and 11 (every 2 weeks):
HaNK 2×10$^9$ cells/dose IV
Day 5, 19, 33 (every 2 weeks for 3 doses then every 8 weeks thereafter):
Ad5 [E1-, E2b-]-MUC1 Ad5 [E1-, E2b-]-Brachyury 5×10" VP/dose SC
GI-6301 Yeast Brachyury 40 YU SC
Day 8 (every 2 weeks):
Avelumab 10 mg/kg by 1 h IV Maintenance Phase: The duration of the maintenance phase will be 1 year following completion of the last treatment in the induction phase. Treatment will continue throughout the maintenance phase unless the subject experiences PD or unacceptable toxicity. Response assessments using CT/MRI evaluated according to RECIST Version 1.1 and irRC will be performed every 3 months during the maintenance phase.

Days 1-5 (weekly):
Cyclophosphamide 50 mg twice a day (BID)
Day 1 (every 2 weeks):
nab-paclitaxel 100 mg IV
Avelumab 10 mg/kg IV
Bevacizumab 5 mg/kg IV
Trabectedin 0.5 mg/kg IV
Day 2 (every 2 weeks):
HaNK 2×10$^9$ cells/dose IV
ALT-803 10 µg/kg SC
Day 5 (every 8 weeks thereafter):
Ad5 [E1-, E2b-]-MUC1 Ad5 [E1-, E2b-]-Brachyury 5×10" VP/dose SC
GI-6301 Yeast Brachyury 40 YU SC In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Furthermore, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used herein, the term "treat", "treating" or "treatment" of any disease or disorder refers, in one embodiment, to the administration of one or more compounds or compositions for the purpose of ameliorating the disease or disorder (e.g., slowing or arresting or reducing the development of the disease or at least one of the clinical symptoms thereof). In another embodiment "treat", "treating", or "treatment" refers to the administration of one or more compounds or compositions for the purpose of alleviating or ameliorating at least one physical parameter including those which may not be discernible by the patient. In yet another embodiment, "treat", "treating", or "treatment" refers to the administration of one or more compounds or compositions for the purpose of modulating the disease or disorder, either symptomatically, (e.g., stabilization of a discernible symptom), physiologically, (e.g., breaking the escape phase of cancer immunoediting, induction of an elimination phase of cancer immunoediting, reinstatement of equilibrium phase of cancer immunoediting), or both. In yet another embodiment, "treat", "treating", or "treatment" refers to the administration of one or more compounds or compositions for the purpose of preventing or delaying the onset or development or progression of the disease or disorder. The terms "treat", "treating", and "treatment" may result, for example in the case of cancer in the stabilization of the disease, partial, or complete response. However, and especially where the cancer is treatment resistant, the terms "treat", "treating", and "treatment" do not imply a cure or even partial cure. As also used herein, the term "patient" refers to a human (including adults and children) or other mammal that is diagnosed or suspected to have a disease, and especially cancer.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating cancer in a patient in need thereof, the method comprising:
   administering to the patient a sequence of therapeutics,
   wherein the sequence comprises a platinum chemotherapeutic, Nab-paclitaxel, haNK cells, an antibody for binding PD-L1, and IL-15 or IL-15N72D;
   wherein the therapeutics are administered in cycles; and
   wherein within the cycle the platinum chemotherapeutic and Nab-paclitaxel are administered before the haNK cells, PD-L1 antibody, and IL-15 or IL-15N72D.

2. The method of claim 1, wherein the PD-L1 antibody is avelumab.

3. The method of claim 1, wherein the IL-15N72D is ALT-803.

4. The method of claim 1, wherein the platinum chemotherapeutic is administered on day 1 of the cycle.

5. The method of claim 4, wherein the Nab-paclitaxel is administered on days 1 and 15 of the cycle.

6. The method of claim 5, wherein the haNK cells are administered on day 9 of the cycle.

7. The method of claim 6, wherein the platinum chemotherapeutic, the PD-L1 antibody, the haNK cells, and the Nab-paclitaxel are administered intravenously (IV), and wherein the ALT-803 is administered subcutaneously.

8. The method of claim 7, wherein the platinum chemotherapeutic is cisplatin.

9. The method of claim 8, wherein the cisplatin dose comprises 125 mg.

10. The method of claim 9, wherein the haNK dose comprises $2 \times 10^9$ cells.

11. The method of claim 10, wherein the antibody dose comprises 10 mg/kg.

12. The method of claim 11, wherein the ALT-803 dose comprises 10 µg/kg.

13. The method of claim 12, wherein the sequence further comprises 5-fluorouracil (5-FU).

14. The method of claim 13, wherein the 5-FU dose comprises 400 mg/m², administered by continuous IV infusion over at least 24 hours.

15. The method of claim 14, wherein the sequence further comprises doxorubicin.

16. The method of claim 15, wherein the doxorubicin dose comprises 20 mg/m².

17. The method of claim 16, wherein the sequence further comprises bevacizumab.

18. The method of claim 17, wherein the bevacizumab dose comprises 5 mg/kg.

19. The method of claim 18, wherein the doxorubicin and bevacizumab are administered IV.

20. The method of claim 1, wherein the cycles are weekly, every two weeks, or every three weeks.

* * * * *